(12) United States Patent
Tidwell et al.

(10) Patent No.: US 10,399,966 B2
(45) Date of Patent: Sep. 3, 2019

(54) COMPOUNDS FOR TREATMENT OF TRYPANOSOMES AND NEUROLOGICAL PATHOGENS AND USES THEREOF

(71) Applicants: The University of North Carolina at Chapel Hill, Chapel Hill, NC (US); University of Washington, Seattle, WA (US)

(72) Inventors: Richard Ray Tidwell, Pittsboro, NC (US); Donald Alan Patrick, Apex, NC (US); Frederick S. Buckner, Seattle, WA (US); Michael H. Gelb, Seattle, WA (US); John R. Gillespie, Seattle, WA (US); Daniel Gedder Silva, Itutinga (BR)

(73) Assignees: University of Washington, Seattle, WA (US); The University of North Carolina at Chapel Hill, Chapel Hill, NC (US); Daniel Gedder Silva, Itutinga, Minas Gerais (BR)

( * ) Notice: Subject to any disclaimer, the term of this patent is extended or adjusted under 35 U.S.C. 154(b) by 0 days.

(21) Appl. No.: 16/071,048

(22) PCT Filed: Jan. 20, 2017

(86) PCT No.: PCT/US2017/014256
§ 371 (c)(1),
(2) Date: Jul. 18, 2018

(87) PCT Pub. No.: WO2017/127627
PCT Pub. Date: Jul. 27, 2017

(65) Prior Publication Data
US 2019/0031649 A1    Jan. 31, 2019

Related U.S. Application Data

(60) Provisional application No. 62/281,475, filed on Jan. 21, 2016.

(51) Int. Cl.
*C07D 417/12* (2006.01)
*A61P 31/00* (2006.01)

(52) U.S. Cl.
CPC .......... *C07D 417/12* (2013.01); *A61P 31/00* (2018.01)

(58) Field of Classification Search
CPC .............................. C07D 417/12; A61P 31/00
See application file for complete search history.

(56) References Cited

U.S. PATENT DOCUMENTS

| 3,337,552 A | 8/1967 | Hirt |
| 2005/0165068 A1 | 7/2005 | Lepape |
| 2009/0163545 A1 | 6/2009 | Goldfarb |
| 2016/0243140 A1 | 8/2016 | Balzarini et al. |
| 2016/0303129 A1 | 10/2016 | Biggart et al. |

FOREIGN PATENT DOCUMENTS

| GB | 1 421 619 A | 1/1976 | |
| WO | 97/07795 A2 | 3/1997 | |
| WO | 2006/066913 A2 | 6/2006 | |
| WO | WO-2006066913 A2 * | 6/2006 | .......... C07D 471/04 |
| WO | 2009/019504 A1 | 2/2009 | |
| WO | 2011/097607 A1 | 8/2011 | |
| WO | 2016/132134 A1 | 8/2016 | |
| WO | 2016/193111 A1 | 12/2016 | |
| WO | 2017/127627 A1 | 7/2017 | |

OTHER PUBLICATIONS

Chibale, K., et al., "Antiprotozoal and Cytotoxicity Evaluation of Sulfonamide and Urea Analogues of Quinacrine," Bioorganic & Medicinal Chemistry Letters 11(19):2655-2657, Oct. 2001.
International Search Report dated Apr. 27, 2017, issued in corresponding International Application No. PCT/US2017/014256, filed Jan. 20, 2017, 5 pages.
Katritzky, A.R., et al., "QSAR Modeling of the Antifungal Activity Against Candida albicans for a Diverse Set of Organic Compounds," Bioorganic & Medicinal Chemistry 16(14):7055-7069, Jul. 2008.
Kulkarni, R.G., et al., "Synthesis, p38 Kinase Inhibitory and Anti-inflammatory Activity of New Substituted Benzimidazole Derivatives," Medicinal Chemistry 9(1):91-99, Feb. 2013.
Lebedeva, M.N., et al., "Dependence of Acute Toxicity on Structure in Series of 2-Substituted Benzimidazoles," Meditsinskaia Parazitologiia i Parazitarnye Bolezni 44(3):316-322, 1975.
Melandri, M., "Reductive Cleavage of 2,6-diacyldiamino-2-butoxy-3,5'-azopyridines," Annali Di Chimica 50:125-133, 1960.
Patrick, D.A., et al., "Synthesis of Novel Amide and Urea Derivatives of Thiazol-2-ethylamines and Their Activity Against Trypanosoma brucei rhodesiense," Bioorganic & Medicinal Chemistry 24(11):2451-2465, Jun. 2016. (Author Manuscript provided, PMCID: PMC4862372, available in PMC Jun. 1, 2017, 35 pages.).
Verma, R.P., and C. Hansch, "A Comparison Between Two Polarizability Parameters in Chemical-Biological Interactions," Bioorganic & Medicinal Chemistry 13(7):2355-2372, Apr. 2005.
Written Opinion of the International Searching authority dated Apr. 17, 2017, issued in corresponding International Application No. PCT/US2017/014256, filed Jan. 20, 2017, 7 pages.

* cited by examiner

*Primary Examiner* — Golam M Shameem
(74) *Attorney, Agent, or Firm* — Christensen O'Connor Johnson Kindness PLLC

(57) ABSTRACT

The present invention relates to novel compounds that cross the blood-brain barrier and are effective inhibitors of neurological pathogens such as trypanosomes. The invention further relates to the use of these compounds for treating disorders related to trypanosomes and neurological pathogens.

10 Claims, 3 Drawing Sheets

COMPOUNDS FOR TREATMENT OF TRYPANOSOMES AND NEUROLOGICAL PATHOGENS AND USES THEREOF

STATEMENT OF PRIORITY

This application claims the benefit of U.S. Provisional Application Ser. No. 62/281,475, filed Jan. 21, 2016, the entire contents of which are incorporated by reference herein.

STATEMENT OF GOVERNMENT SUPPORT

This invention was made with government support under Grant No. 5RO1AI106850-02 awarded by National Institutes of Health. The United States Government has certain rights to this invention.

FIELD OF THE INVENTION

The present invention relates to novel compounds that cross the blood-brain barrier and are effective inhibitors of neurological pathogens such as trypanosomes. The invention further relates to the use of these compounds for treating disorders related to trypanosomes and neurological pathogens.

BACKGROUND OF THE INVENTION

Human African trypanosomiasis (HAT) occurs in 36 nations of sub-Saharan Africa. In 2015 the World Health Organization (WHO) estimated 20,000 actual cases with 65 million people at risk. Transmitted by tsetse flies, the disease is due to a chronic infection of *Trypanosoma brucei gambiense* (in western and central Africa, over 98% of reported cases) or an acute infection of *Trypanosoma brucei rhodesiense* (in southern and eastern Africa). The *T. b. gambiense* infection is characterized by a slow progression from early (hemolymphatic) stage—where many patients are asymptomatic—to late stage disease, after the parasites have entered the central nervous system (CNS). The *T. b. rhodesiense* infection is characterized by earlier onset of symptoms and a more rapid progression from early to late stage. In either case, late stage HAT is always fatal if untreated (who.int/mediacentre/factsheets/fs259/en/).

The need for new anti-HAT drugs continues to persist, as current drugs are few, antiquated, toxic, prone to resistance, and require parenteral administration. Treatments for *T. b. rhodesiense* infections are limited to suramin (a polysulfonated naphthylurea) for early stage and melarsoprol (an organoarsenical) for late stage disease. Treatments for *T. b. gambiense* infections include pentamidine (an aromatic diamidine) for early stage and melarsoprol, eflornithine, or nitifurtimox-eflornithine combination therapy (NECT) for late stage disease (who.int/mediacentre/factsheets/fs259/en/; Astelbauer et al., *Int. J. Antimicrob. Agents* 38:118 (2011); Burri, *Parasitology* 137:1987 (2010)).

There is need for compounds that are orally available, cross the blood brain barrier, and are effective against trypanosomes and other neurological pathogens.

SUMMARY OF THE INVENTION

The present invention relates to novel compounds that are orally available and cross the blood brain barrier (BBB), and are potent inhibitors of trypanosomes. The compounds effective for treatment of trypanosome infections and trypanosome-related diseases in both the peripheral and central nervous system (CNS) stages. The compounds may also be useful for the treatment of other neurological pathogens due to their ability to accumulate in the CNS.

Accordingly, one aspect of the invention relates to invention relates to a compound of formula I:

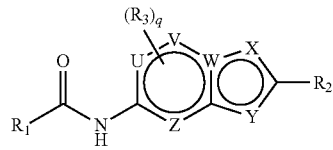

wherein:

X is S, O, or NH;

V is N or CH;

W is N or CH;

Y is N or CH;

Z is N or CH;

$R_1$ is a $C_{4-6}$ cycloalkyl, heterocycloalkyl, aryl, or heteroaryl, unsubstituted or substituted with one or more $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group;

$R_2$ is a $C_{5-7}$ cycloalkyl, heterocycloalkyl, aryl, or heteroaryl, unsubstituted or substituted with one or more $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group;

$R_3$ is a $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group; and q is an integer from 0-3;

or a pharmaceutically acceptable salt, prodrug, or optical isomer thereof.

Another aspect of the invention relates to a compound of formula II:

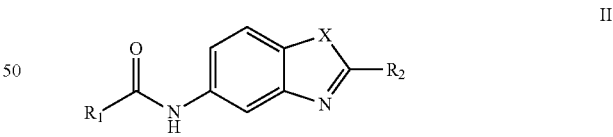

wherein:

X is S, O, or NH;

$R_1$ is a $C_{4-6}$ cycloalkyl, heterocycloalkyl, aryl, or heteroaryl, unsubstituted or substituted with one or more $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group; and $R_2$ is a $C_{5-7}$ cycloalkyl, heterocycloalkyl, aryl, or heteroaryl, unsubstituted or substituted with one or more $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group;

or a pharmaceutically acceptable salt, prodrug, or optical isomer thereof.

A further aspect of the invention relates to a compound of formula III:

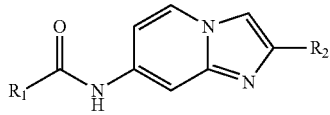

III wherein:
$R_1$ is a $C_{4-6}$ cycloalkyl, heterocycloalkyl, aryl, or heteroaryl, unsubstituted or substituted with one or more $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group; and
$R_2$ is a $C_{5-7}$ cycloalkyl, heterocycloalkyl, aryl, or heteroaryl, unsubstituted or substituted with one or more $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group;
or a pharmaceutically acceptable salt, prodrug, or optical isomer thereof.

The invention further relates to a pharmaceutical composition comprising a compound of the invention and a pharmaceutically acceptable carrier.

The invention additionally relates to a kit comprising a compound of the invention.

The invention also relates to a method of treating or preventing a disorder caused by a trypanosome in a subject in need thereof, comprising delivering to the subject a therapeutically effective amount of a compound or pharmaceutical composition of the invention, thereby treating or preventing the disorder.

The invention further relates to a method of treating or preventing a disorder caused by a neurological pathogen in a subject in need thereof, comprising delivering to the subject a therapeutically effective amount of a compound or pharmaceutical composition of the invention, thereby treating or preventing the disorder.

The invention also relates to the use of a compound of the invention for treating or preventing a disorder caused by a trypanosome or treating or preventing a disorder caused by a neurological pathogen.

The present invention is explained in greater detail in the drawings herein and the specification set forth below.

DETAILED DESCRIPTION OF THE INVENTION

Figure 1:
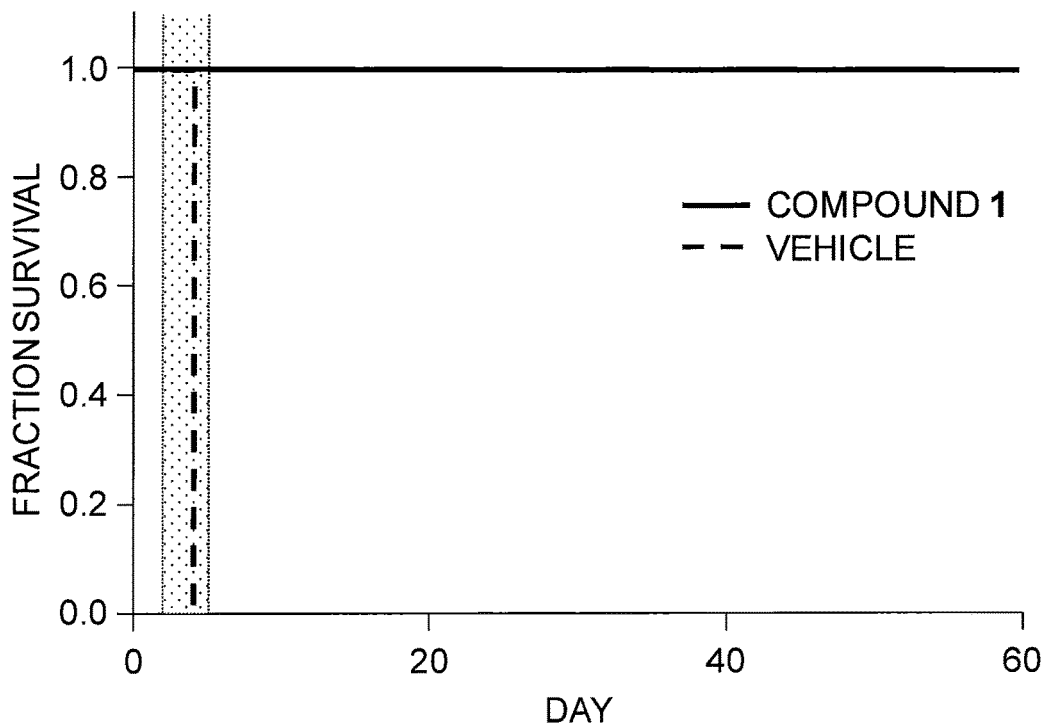
FIG. 1 shows mouse efficacy model of acute T. brucei infection. All mice were infected with T. b. rhodesiense STIB900 on day 0. Groups of five mice were treated with compound 1 (50 mg/kg by oral gavage b.i.d.) or vehicle from day 2-5 (gray-shaded area.) Mice were monitored for parasitemia in tail blood samples through day 60 post-infection.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

All publications, patent applications, patents, and other references mentioned herein are incorporated by reference herein in their entirety.

Definitions

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, etc., as would be well known in the art.

The terms "prevent," "preventing," and "prevention" refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

The term "therapeutically effective amount" or "effective amount," as used herein, refers to that amount of a composition, compound, or agent of this invention that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, a therapeutically effective amount or effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science;* 21$^{st}$ ed. 2005). Exemplary pharmaceutically acceptable carriers for the compositions of this invention include, but are not limited to, sterile pyrogen-free water and sterile pyrogen-free physiological saline solution.

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

The term "neurological pathogen," as used herein, refers to an organism, e.g., a parasite or bacterium, that is present in the central nervous system of a subject at some point after initial contact of the pathogen with the subject.

The term "disorder caused by a neurological pathogen," as used herein, refers to any disorder that occurs when a subject is infected with a neurological pathogen.

The term "disorder caused by a trypanosome," as used herein, refers to any disorder that occurs when a subject is infected with a trypanosome.

The term "alkyl" denotes a straight or branched hydrocarbon chain containing 1-12 carbon atoms, e.g., 1-6 carbon atoms. Examples of alkyl group include methyl, ethyl, propyl, isopropyl, butyl, isobutyl, tert-butyl, and the like.

The term "alkoxy" denotes an oxygen linked to an alkyl as defined above.

The terms "halo" and "halogen" refer to any radical of fluorine, chlorine, bromine or iodine.

The terms "ring" and "ring system" refer to a ring comprising the delineated number of atoms, said atoms being carbon or, where indicated, a heteroatom such as nitrogen, oxygen or sulfur. The ring itself, as well as any substituents thereon, can be attached at any atom that allows a stable compound to be formed.

The term "cycloalkyl" refers to a 4-8 membered monocyclic ring system wherein 0, 1, 2, 3, or 4 atoms of each ring can be substituted by a substituent. Examples of cycloalkyl groups include cyclobutyl, cyclopentyl, cyclohexyl, cycloheptyl, cyclooctyl and the like.

The term "heterocycloalkyl" refers to a 4-8 membered monocyclic ring system comprising 1-3 heteroatoms, said heteroatoms selected from O, N, or S, wherein 0, 1, 2, 3, or 4 atoms of each ring can be substituted by a substituent. Examples of heterocycloalkyl groups include pyrrolidinyl, pyrazolidinyl, imidazolidinyl, piperidinyl, piperazinyl, morpholinyl, and the like.

The term "aryl" refers to an aromatic 5-8 membered monocyclic or 8-12 membered bicyclic ring system wherein 0, 1, 2, 3, or 4 atoms of each ring can be substituted by a substituent. Examples of aryl groups include phenyl, naphthyl and the like.

The term "heteroaryl" refers to an aromatic 5-8 membered monocyclic or 8-12 membered bicyclic ring system comprising 1-3 heteroatoms if monocyclic or 1-6 heteroatoms if bicyclic, said heteroatoms selected from O, N, or S, wherein 0, 1, 2, 3, or 4 atoms of each ring can be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, oxazolyl, and the like.

Suitable substituents for cycloalkyl, heterocycloalkyl, aryl, and heteroaryl groups include cyclyl groups, heterocyclyl groups; aryl groups, heteroaryl groups, amino groups, alkylamino groups, amido groups, nitro groups, cyano groups, azide groups, hydroxy groups, alkyl groups, haloalkyl groups, alkoxy groups, acyloxy groups, thioalkoxy groups, acyl thioalkoxy groups, halogen groups, sulfonate groups, sulfonamide groups, ester groups, carboxylic acids, oxygen (e.g., a carbonyl group), and sulfur (e.g., a thiocarbonyl group). Substituents also include any chemical functional group that imparts improved water-solubility to the molecule (e.g., carboxylic acid, carboxylic ester, carboxamido, morpholino, piperazinyl, imidazolyl, thiomorpholino, or tetrazolyl groups; both unsubstituted and substituted).

One aspect of the invention relates to a compound of formula I:

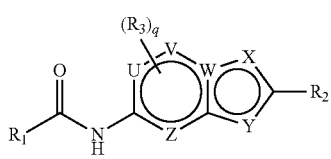

wherein:
X is S, O, or NH;
V is N or CH;
W is N or CH;
Y is N or CH;
Z is N or CH;
$R_1$ is a $C_{4-6}$ cycloalkyl, heterocycloalkyl, aryl, or heteroaryl, unsubstituted or substituted with one or more $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group;
$R_2$ is a $C_{5-7}$ cycloalkyl, heterocycloalkyl, aryl, or heteroaryl, unsubstituted or substituted with one or more $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group;
$R_3$ is a $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group; and
q is an integer from 0-3;
or a pharmaceutically acceptable salt, prodrug, or optical isomer thereof.

In some embodiments, no more than four of U, V, W, X, Y, and Z is N or NH, e.g., no more than three are N or NH. In some embodiments, U, V, W, X, Y, and Z are selected such that heteroatoms are not directly connected with each other. In certain embodiments U, V, W, X, Y, and Z are selected to form a benzothiazole structure, a benzoxazole structure, or a benzimidazole structure. In some embodiments, U, V, W, X, Y, and Z are selected to form one of the following core structures:

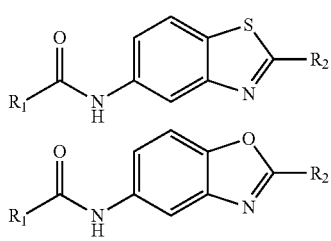

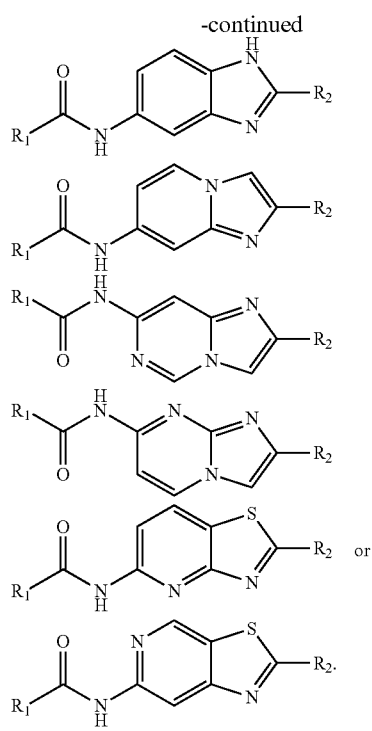

Another aspect of the invention relates to a compound of formula I having formula II:

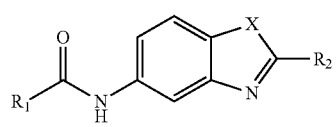

wherein:
X is S, O, or NH;
$R_1$ is a $C_{4-6}$ cycloalkyl, heterocycloalkyl, aryl, or heteroaryl, unsubstituted or substituted with one or more $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group; and
$R_2$ is a $C_{5-7}$ cycloalkyl, heterocycloalkyl, aryl, or heteroaryl, unsubstituted or substituted with one or more $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group;
or a pharmaceutically acceptable salt, prodrug, or optical isomer thereof.

A further aspect of the invention relates to a compound of formula I, having formula III:

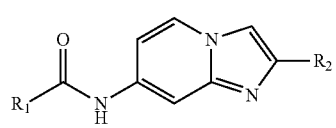

wherein:
$R_1$ is a $C_{4-6}$ cycloalkyl, heterocycloalkyl, aryl, or heteroaryl, unsubstituted or substituted with one or more $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group; and R₂ is a $C_{5-7}$ cycloalkyl, heterocycloalkyl, aryl, or heteroaryl, unsubstituted or substituted with one or more $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group;
or a pharmaceutically acceptable salt, prodrug, or optical isomer thereof.

In certain embodiments of the compounds of formula I, II, or III, $R_1$ is a substituted or unsubstituted cycloalkyl or heterocycloalkyl. In some embodiments, $R_1$ is a substituted or unsubstituted pyrrolidine. In some embodiments, $R_1$ is a substituted or unsubstituted oxazole or thiazole. In certain embodiments, $R_1$ is:

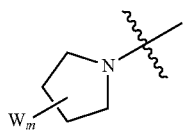

wherein:
W is $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group; and
m is an integer from 0-4.

In certain embodiments, $R_2$ is a substituted or unsubstituted aryl or heteroaryl. In certain embodiments, $R_2$ is:

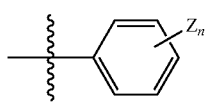

wherein:
Z is $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group; and
n is an integer from 0-4.

In some embodiments, the compound of the invention has formula IV:

IV

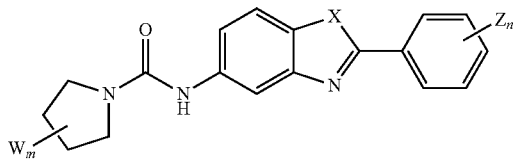

wherein:
X is S, O, or NH;
W is $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group;
m is an integer from 0-4;
Z is $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group; and
n is an integer from 0-4;
or a pharmaceutically acceptable salt, prodrug, or optical isomer thereof.

In some embodiments of the compounds of the invention, e.g., the compound of formula I, II, or IV, X is S.

In some embodiments of the compounds of the invention, e.g., the compound of formula I, II, or IV, m is 1 or 2 and/or n is 1, 2, or 3.

In some embodiments of the compounds of the invention, e.g., the compound of formula I, II, or IV, W and/or Z is halo, e.g., F.

In some embodiments of the compounds of the invention, e.g., the compound of formula I, II, or IV, $R_2$ is:

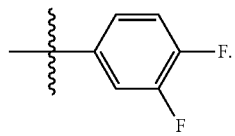 [SMILES: *c1ccc(F)c(F)c1]

In specific embodiments, the compound of the invention is

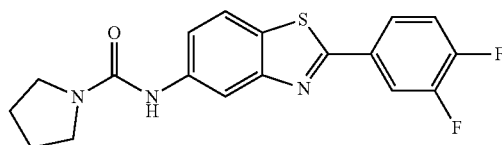

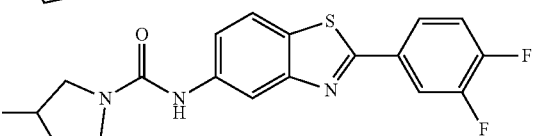

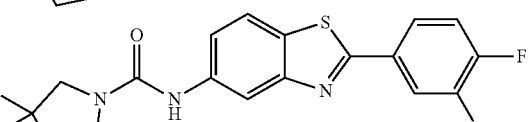

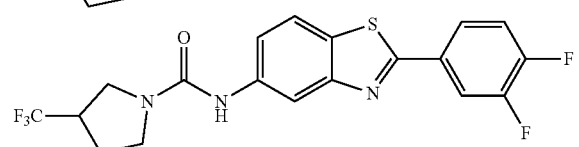

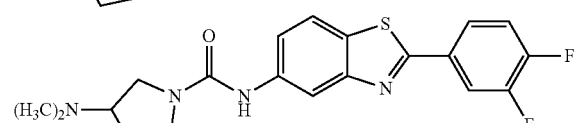

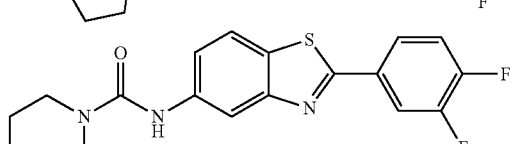

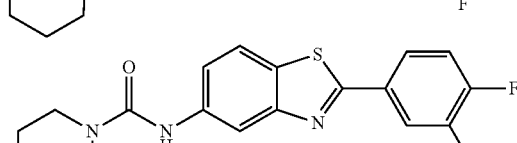

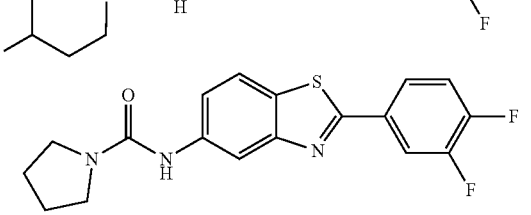

-continued

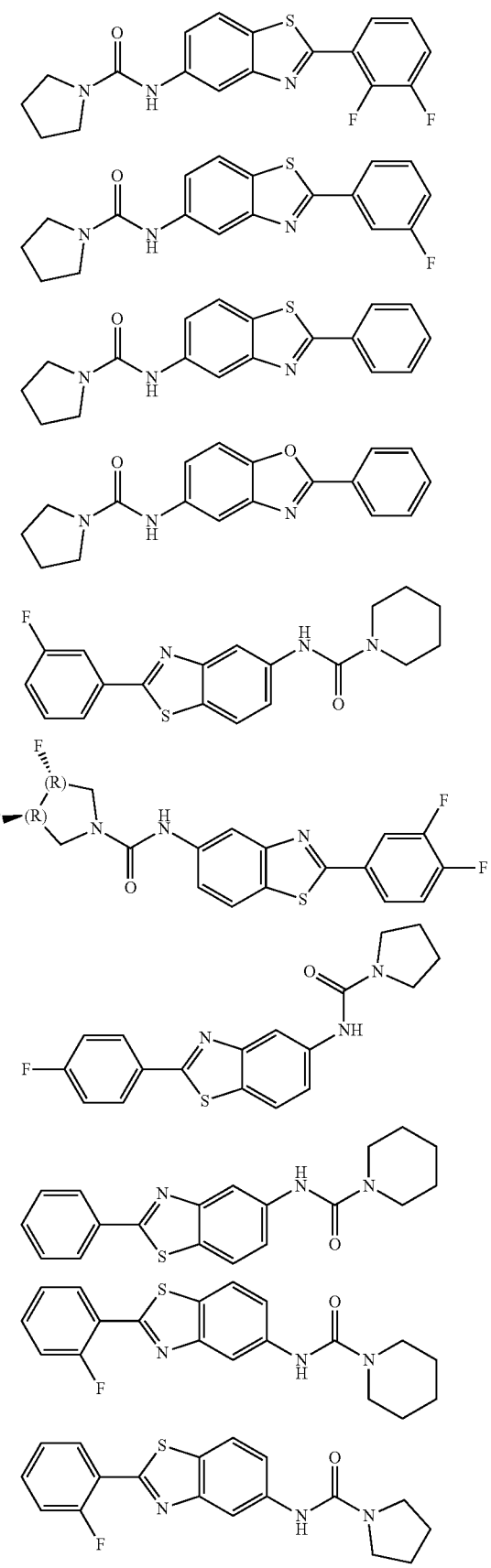

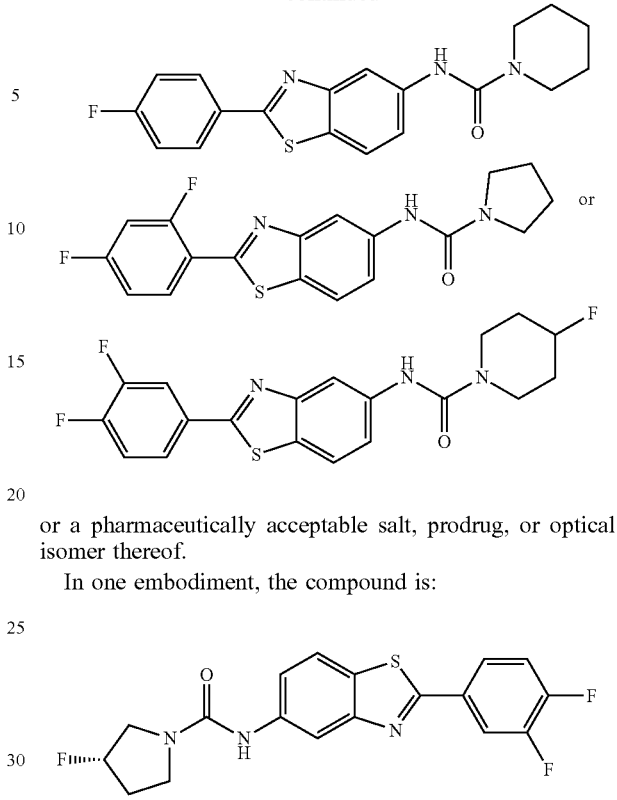

or a pharmaceutically acceptable salt, prodrug, or optical isomer thereof.

In one embodiment, the compound is:

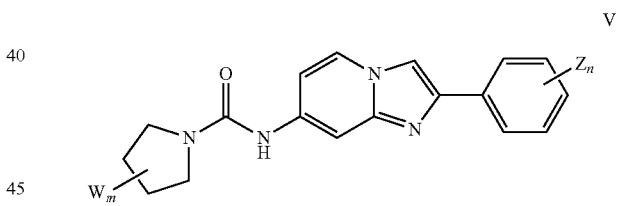

or a pharmaceutically acceptable salt or prodrug thereof.

In some embodiments, the compound of the invention has formula V:

$$V$$

wherein:
W is $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group;
m is an integer from 0-4;
Z is $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group; and
n is an integer from 0-4;
or a pharmaceutically acceptable salt, prodrug, or optical isomer thereof.

In some embodiments of the compounds of the invention, e.g., the compound of formula I, III, or V, X is S.

In some embodiments of the compounds of the invention, e.g., the compound of formula I, III, or V, m is 1 or 2 and/or n is 1, 2, or 3.

In some embodiments of the compounds of the invention, e.g., the compound of formula I, III, or V, W and/or Z is halo, e.g., F.

In some embodiments of the compounds of the invention, e.g., the compound of formula I, III, or V, R₂ is:

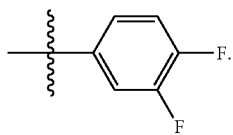

In specific embodiments, the compound of the invention is

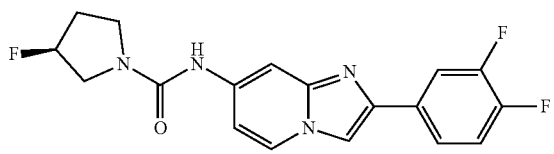

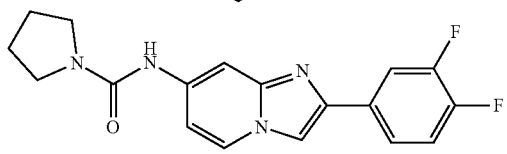

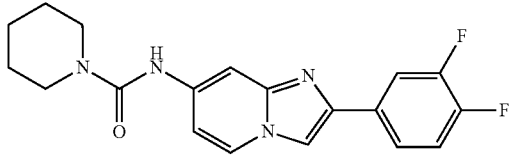

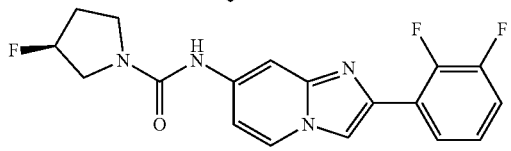

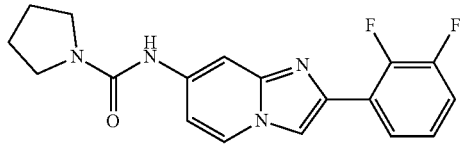

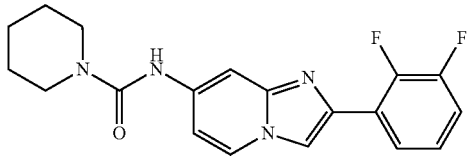

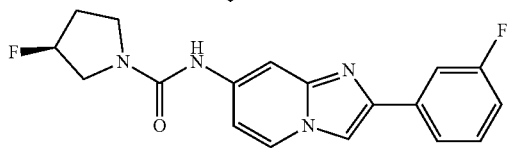

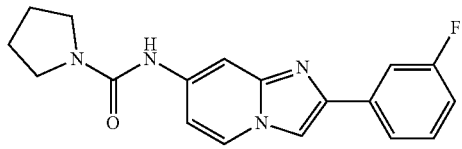

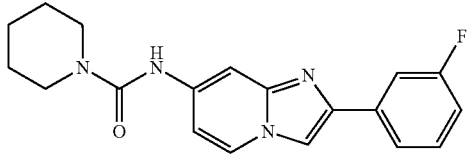

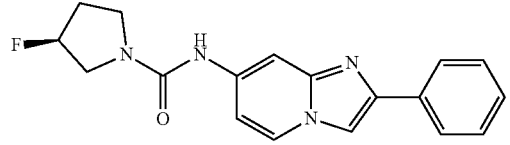

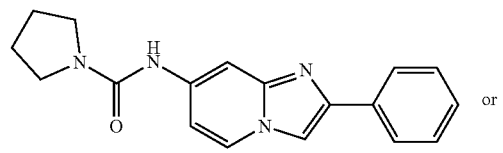

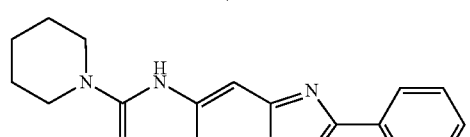

or a pharmaceutically acceptable salt, prodrug, or optical isomer thereof.

In specific embodiments, the compound of the invention is

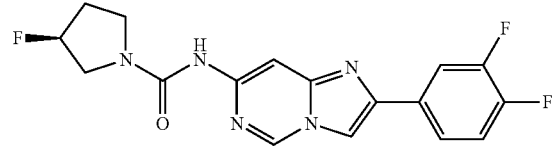

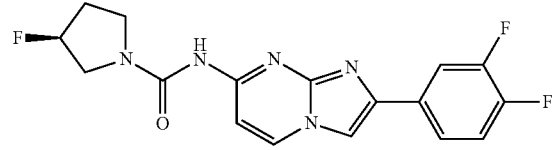

or a pharmaceutically acceptable salt, prodrug, or optical isomer thereof.

In specific embodiments, the compound of the invention is

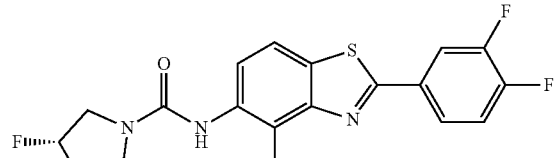

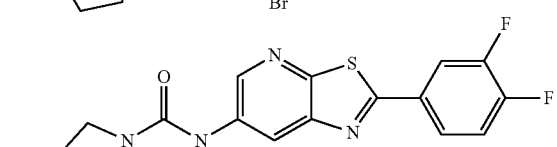

-continued

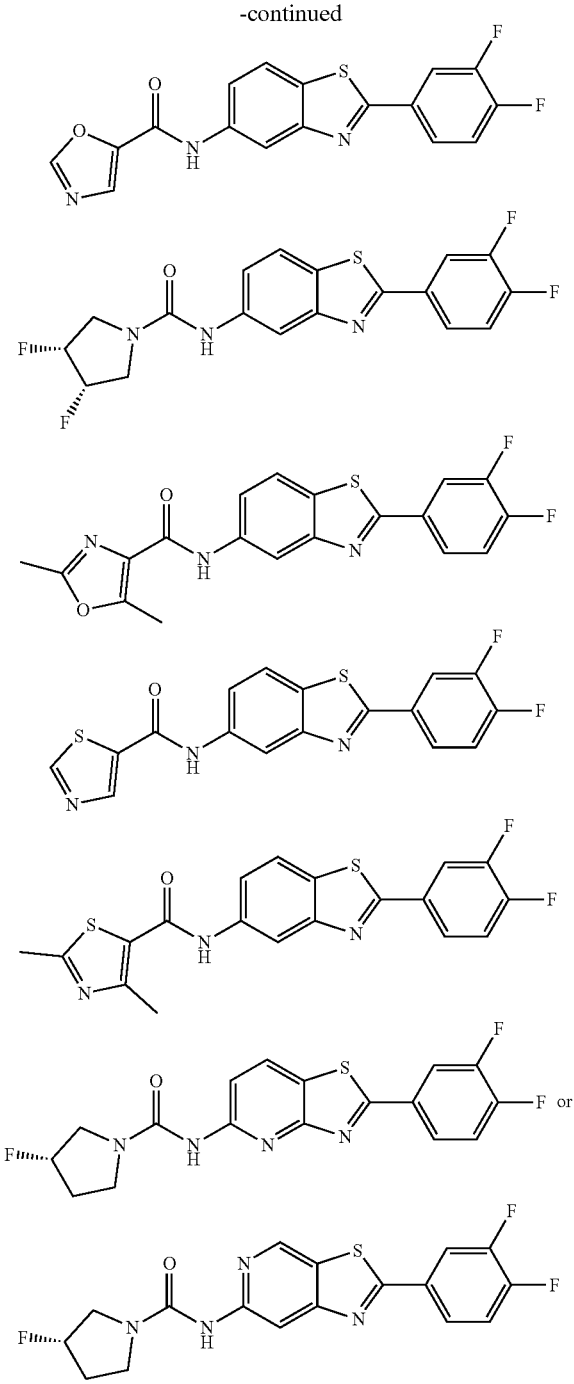

or a pharmaceutically acceptable salt, prodrug, or optical isomer thereof.

In certain embodiments, the compound of the invention is one that penetrates the blood brain barrier and exhibits a brain/plasma ratio 60 minutes after systemic administration of the compound of at least 1, e.g., at least 2, 3, 4, 5, 6, 7, 8, or more.

Another aspect of the invention relates to a pharmaceutical composition comprising the compound of the invention and a pharmaceutically acceptable carrier. Pharmaceutical carriers are described further below.

A further aspect of the invention relates to a kit comprising the compound of the invention, e.g., a kit useful for carrying out the methods of the invention. The kit may comprise one or more of the compounds of the invention. The kit may further comprise other components useful for storing, mixing, and/or administering the compound, e.g., containers, buffers, measuring devices, administration devices, etc.

The compounds of the invention can be synthesized by methods well known in the art and as shown in the examples below.

The compounds of this invention include all pharmaceutically acceptable salt forms thereof. Examples of such salts include those derived from pharmaceutically acceptable inorganic and organic acids and bases. Examples of suitable acid salts include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynapthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the invention and their pharmaceutically acceptable acid addition salts.

Salts derived from appropriate bases include, without limitation, alkali metal (e.g., sodium, potassium), alkaline earth metal (e.g., magnesium and calcium), ammonium and N-(alkyl)$_4^+$ salts.

Compounds of the formulae herein include those having quaternization of any basic nitrogen-containing group therein.

The discussion herein is, for simplicity, provided without reference to stereoisomerism. Those skilled in the art will appreciate that the compounds of the invention can contain one or more asymmetric centers and thus occur as racemates and racemic, mixtures, single optical isomers, individual enantiomers or diastereomers, and enantiomeric or diastereomeric mixtures. All such isomeric forms of these compounds are expressly included in the present invention. When enantiomers or diastereomers exist, a composition comprising the same may have an excess of a single enantiomer or diastereomer, e.g., 51%, 60%, 70%, 80%, 90%, 95%, 96%, 97%, 98%, 99%, or more excess.

Similarly, compounds of the invention containing a double bond can exist in the form of geometric isomers, which can be readily separated and recovered by conventional procedures. Such isomeric forms are included in the scope of this invention. The compounds of the invention also include all tautomeric forms.

Further, the compounds of the invention include prodrugs of the compounds that are converted to the active compound in vivo. For example, the compound can be modified to enhance cellular permeability (e.g., by esterification of polar groups) and then converted by cellular enzymes to produce the active agent. Methods of masking charged or reactive moieties as a pro-drug are known by those skilled in the art (see, e.g., P. Korgsgaard-Larsen and H. Bundgaard, A Textbook of Drug Design and Development, Reading U.K., Harwood Academic Publishers, 1991).

The term "prodrug" refers to compounds that are rapidly transformed in vivo to yield the parent compound of the above formula, for example, by hydrolysis in blood, see, e.g., T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Exemplary prodrugs include a prodrug that is metabolized in vivo by a subject to an active drug having an activity of the compounds as described herein, wherein the prodrug is an ester of an alcohol or carboxylic acid group, if such a group is present in the compound; an amide of an amine group or carboxylic acid group, if such groups are present in the compound; a urethane of an amine group, if such a group is present in the compound; an acetal or ketal of an alcohol group, if such a group is present in the compound; a N-Mannich base or an imine of an amine group, if such a group is present in the compound; or a Schiff base, oxime, acetal, enol ester, oxazolidine, or thiazolidine of a carbonyl group, if such a group is present in the compound, such as described, for example, in U.S. Pat. Nos. 6,680,324 and 6,680,322.

The term "pharmaceutically acceptable prodrug" (and like terms) as used herein refers to those prodrugs of the compounds of the present invention which are, within the scope of sound medical judgment, suitable for use in contact with the tissues of humans and/or other animals without undue toxicity, irritation, allergic response and the like, commensurate with a reasonable risk/benefit ratio, and effective for their intended use, as well as the zwitterionic forms, where possible, of the compounds of the invention.

After extensive screening efforts, the present inventors have developed the compounds of the present invention that were surprisingly found to be both orally available and capable of crossing the BBB. Thus, the compounds are highly suitable for the treatment and/or prevention of infection with pathogens that are found in the CNS. The compounds have been demonstrated to be effective and potent inhibitors of trypanosomes, treating both acute (peripheral) and chronic (CNS) infection. Because of the surprising ability of the compounds to cross the BBB, they may also be suitable for treatment and/or prevention of other neurological pathogens.

Thus, one aspect of the invention relates to a method of treating or preventing a disorder caused by a trypanosome in a subject in need thereof, comprising delivering to the subject a therapeutically effective amount of the compound or pharmaceutical composition of the invention, thereby treating the disorder. The disorder may be any disorder caused by any trypanosome. In one embodiment, the trypanosome is *Trypanosoma brucei* and the disorder is African sleeping sickness. In another embodiment, the trypanosome is *Trypanosoma cruzi* and the disorder is Chagas disease.

Another aspect of the invention relates to a method of treating or preventing a disorder caused by a neurological pathogen in a subject in need thereof, comprising delivering to the subject a therapeutically effective amount of the compound or pharmaceutical composition of the invention, thereby treating the disorder. The neurological pathogen may be any pathogen that is present in the CNS of an infected subject at some point during the infection and causes a disease or disorder, e.g., meningitis, encephalitis, toxoplasmosis, malaria, tuberculosis, leprosy, neurosyphilis, etc. Examples of neurological pathogens include, without limitation, parasites (e.g., trypanosomes), protozoans (e.g., *Toxoplasma gondii, Plasmodium* spp., *Naegleria fowleri*), fungi (e.g., *Cryptococcus neoformans*), bacteria (e.g., *Neisseria meningitidis, Streptococcus pneumoniae, Listeria monocytogenes, Mycobacterium tuberculosis, Mycobacterium leprae, Treponoma pallidum*), and viruses (e.g., enteroviruses, herpes simplex virus, rabies virus, poliovirus, measles virus, human papilloma virus).

In some embodiments, the compound is administered concurrently with an additional therapeutic agent. In certain embodiments, the compound is administered in the same pharmaceutical composition as the additional therapeutic agent. In other embodiments, the compound is administered in a different pharmaceutical composition than the additional therapeutic agent. The additional therapeutic agent can be delivered to the subject on a different schedule or by a different route as compared to the compound. The additional therapeutic agent can be any agent that provides a benefit to the subject. Examples of other therapeutic agents include, without limitation, anti-parasitic agents (e.g., suramin, melarsoprol, pentamidine, melarsoprol, eflornithine), anti-fungal agents (e.g., amphotericin B, flucytosine), anti-bacterial agents (e.g., penicillins, cephalosporins, vancomycin, chloramphenicol), anti-viral agents (e.g., acyclovir), and other agents (e.g., steroids, sedatives).

In one embodiment of the invention, one or more of the compounds of the invention is administered to the subject as needed to treat and/or prevent a disorder. The compound can be administered continuously or intermittently. In one embodiment, the compound is administered to the subject more than once a day or once every 1, 2, 3, 4, 5, 6, or 7 days. In another embodiment, the compound is administered to the subject no more than once a week, e.g., no more than once every two weeks, once a month, once every two months, once every three months, once every four months, once every five months, once every six months, or longer. In a further embodiment, the compound is administered using two or more different schedules, e.g., more frequently initially (for example to build up to a certain level, e.g., once a day or more) and then less frequently (e.g., once a week or less). In other embodiments, the compound can be administered by any discontinuous administration regimen. In one example, the compound can be administered not more than once every three days, every four days, every five days, every six days, every seven days, every eight days, every nine days, or every ten days, or longer. The administration can continue for one, two, three, or four weeks or one, two, or three months, or longer. Optionally, after a period of rest, the compound can be administered under the same or a different schedule. The period of rest can be one, two, three, or four weeks, or longer, according to the pharmacodynamic effects of the compound on the subject.

The compound of the invention can be delivered to the subject by any suitable route, e.g., oral, rectal, buccal (e.g., sub-lingual), vaginal, parenteral (e.g., subcutaneous, intramuscular, intradermal, or intravenous), topical (i.e., both skin and mucosal surfaces, including airway surfaces) and transdermal administration. The compound is delivered to the subject at a dose that is effective to treat the disorder. The effective dosage will depend on many factors including the gender, age, weight, and general physical condition of the subject, the severity of the disorder, the particular compound or composition being administered, the duration of the treatment, the nature of any concurrent treatment, the carrier used, and like factors within the knowledge and expertise of those skilled in the art. As appropriate, a treatment effective amount in any individual case can be determined by one of ordinary skill in the art by reference to the pertinent texts and literature and/or by using routine experimentation (see, e.g., Remington, *The Science and Practice of Pharmacy* ($21^{st}$ ed. 2005)). In one embodiment, the compound is administered at a dose of about 0.001 to about 10 mg/kg body weight, e.g., about 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, or 10 mg/kg. In some instances, the dose can be even lower, e.g., as low as 0.0005 or 0.0001 mg/kg or lower. In some instances, the dose can be even higher, e.g., as high as 20, 50, 100, 500, or 1000 mg/kg or higher. The present invention encompasses every sub-range within the cited ranges and amounts.

The present invention finds use in research as well as veterinary and medical applications. Suitable subjects are generally mammalian subjects. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects.

In particular embodiments, the subject is a human subject that has been infected with a trypanosome or neurological pathogen or is suspected of having been infected with a trypanosome or neurological pathogen (e.g., has not yet developed signs or symptoms of infection). In some embodiments, the subject is one that is at risk for infection (e.g., due to exposure (such as during travel)). In other embodiments, the subject used in the methods of the invention is an animal model of a disorder caused by a trypanosome or neurological pathogen.

The subject can be a subject "in need of" the methods of the present invention, e.g., in need of the therapeutic or prophylactic effects of the inventive methods. For example, the subject can be a subject that is experiencing a disorder caused by a trypanosome or neurological pathogen and/or is anticipated to experience a disorder caused by a trypanosome or neurological pathogen, and the methods and compositions of the invention are used for therapeutic and/or prophylactic treatment.

The compounds of the invention described above can be formulated for administration in a pharmaceutical carrier in accordance with known techniques. See, e.g., Remington, *The Science And Practice of Pharmacy* ($21^{st}$ ed. 2005). In the manufacture of a pharmaceutical formulation according to the invention, the compound is typically admixed with, inter alia, an acceptable carrier. The carrier must, of course, be acceptable in the sense of being compatible with any other ingredients in the formulation and must not be deleterious to the patient. The carrier can be a solid or a liquid, or both, and can be formulated with the compound as a unit-dose formulation, for example, a tablet, which can contain from 0.01% or 0.5% to 95% or 99% by weight of the compound. One or more compounds can be incorporated in the formulations of the invention, which can be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration can be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations can be prepared by any suitable method of pharmacy which includes the step of bringing into association the compound and a suitable carrier (which can contain one or more accessory ingredients as noted above). In general, the formulations of the invention are prepared by uniformly and intimately admixing the compound with a liquid or finely divided solid carrier, or both, and then, if necessary, shaping the resulting mixture. For example, a tablet can be prepared by compressing or molding a powder or granules containing the compound, optionally with one or more accessory ingredients. Compressed tablets can be prepared by compressing, in a suitable machine, the compound in a free-flowing form, such as a powder or granules optionally mixed with a binder, lubricant, inert diluent, and/or surface active/dispersing agent(s). Molded tablets can be made by molding, in a suitable machine, the powdered compound moistened with an inert liquid binder.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose (e.g., in a syringe or other injection device) or multi-dose containers, for example sealed ampoules and vials, and can be stored in a freeze-dried (lyophilized) condition requiring only the addition of the sterile liquid carrier, for example, saline or water-for-injection immediately prior to use. Extemporaneous injection solutions and suspensions can be prepared from sterile powders, granules and tablets of the kind previously described. For example, in one aspect of the present invention, there is provided an injectable, stable, sterile composition comprising one or more compounds, in a unit dosage form in a sealed container. The compound is provided in the form of a lyophilizate which is capable of being reconstituted with a suitable pharmaceutically acceptable carrier to form a liquid composition suitable for injection thereof into a subject. The unit dosage form typically comprises from about 0.001 mg to about 10 grams of the compound. When the compound is substantially water-insoluble (e.g., when conjugated to a lipid), a sufficient amount of emulsifying agent which is physiologically acceptable can be employed in sufficient quantity to emulsify the compound in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharm. Res.* 3:318 (1986)) and typically take the form of an optionally buffered aqueous solution of the compound. Suitable formulations comprise citrate or bis\tris buffer (pH 6) or ethanol/water and contain from 0.1 to 0.2 M active ingredient.

Other pharmaceutical compositions can be prepared from the compounds disclosed herein, such as aqueous base emulsions. In such an instance, the composition will contain a sufficient amount of pharmaceutically acceptable emulsifying agent to emulsify the desired amount of the compound. Particularly useful emulsifying agents include phosphatidyl cholines and lecithin.

In addition to the compound, the pharmaceutical compositions can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions can contain microbial preservatives. Useful microbial preservatives include methylparaben, propylparaben, and benzyl alcohol. The microbial preservative is typically employed when the formulation is placed in a vial designed for multidose use. Other additives that are well known in the art include, e.g., detackifiers, anti-foaming agents, antioxidants (e.g., ascorbyl palmitate, butyl hydroxy anisole (BHA), butyl hydroxy toluene (BHT) and tocopherols, e.g., α-tocopherol (vitamin E)), preservatives, chelating agents (e.g., EDTA and/or EGTA), viscomodulators, tonicifiers (e.g., a sugar such as sucrose, lactose, and/or mannitol), flavorants, colorants, odorants, opacifiers, suspending agents, binders, fillers, plasticizers, lubricants, and mixtures thereof. The amounts of such additives can be readily determined by one skilled in the art, according to the particular properties desired.

The additive can also comprise a thickening agent. Suitable thickening agents can be those known and employed in the art, including, e.g., pharmaceutically acceptable polymeric materials and inorganic thickening agents. Exemplary thickening agents for use in the present pharmaceutical compositions include polyacrylate and polyacrylate co-polymer resins, for example poly-acrylic acid and poly-acrylic acid/methacrylic acid resins; celluloses and cellulose derivatives including: alkyl celluloses, e.g., methyl-, ethyl- and propyl-celluloses; hydroxyalkyl-celluloses, e.g., hydroxypropyl-celluloses and hydroxypropylalkyl-celluloses such as hydroxypropyl-methyl-celluloses; acylated celluloses, e.g., cellulose-acetates, cellulose-acetatephthallates, cellulose-acetatesuccinates and hydroxypropylmethyl-cellulose phthallates; and salts thereof such as sodium-carboxymethyl-celluloses; polyvinylpyrrolidones, including for example poly-N-vinylpyrrolidones and vinylpyrrolidone copolymers such as vinylpyrrolidone-vinylacetate co-polymers; polyvinyl resins, e.g., including polyvinylacetates and alcohols, as well as other polymeric materials including gum traganth, gum arabicum, alginates, e.g., alginic acid, and salts thereof, e.g., sodium alginates; and inorganic thickening agents such as atapulgite, bentonite and silicates including hydrophilic silicon dioxide products, e.g., alkylated (for example methylated) silica gels, in particular colloidal silicon dioxide products. Such thickening agents as described above can be included, e.g., to provide a sustained release effect. However, where oral administration is intended, the use of thickening agents as aforesaid will generally not be required and is generally less preferred. Use of thickening agents is, on the other hand, indicated, e.g., where topical application is foreseen.

Further, the present invention provides liposomal formulations of the compounds disclosed herein. The technology for forming liposomal suspensions is well known in the art. When the compound is in the form of an aqueous-soluble material, using conventional liposome technology, the same can be incorporated into lipid vesicles. In such an instance, due to the water solubility of the compound, the compound will be substantially entrained within the hydrophilic center or core of the liposomes. The lipid layer employed can be of any conventional composition and can either contain cholesterol or can be cholesterol-free. When the compound of interest is water-insoluble, again employing conventional liposome formation technology, the compound can be substantially entrained within the hydrophobic lipid bilayer which forms the structure of the liposome. In either instance, the liposomes which are produced can be reduced in size, as through the use of standard sonication and homogenization techniques. The liposomal formulations containing the compound disclosed herein, can be lyophilized to produce a lyophilizate which can be reconstituted with a pharmaceutically acceptable carrier, such as water, to regenerate a liposomal suspension.

The present invention is explained in greater detail in the following non-limiting Examples.

Example 1

Screening of Compounds

A phenotypic screen of a library of over 700,000 compounds (provided by Genomics Institute of the Novartis Research Foundation) led to 1009 confirmed hits that killed the blood stream form of *T. brucei* in vivo at concentrations <4 µM. After applying Lipinsky rules and eliminating compounds with structure alerts for toxicity and synthetic incompatibilities, the hits were narrowed down to 20 potential lead compounds. The list was further prioritized by determining blood-brain barrier penetration of lead compounds. A total of 15 molecular scaffolds were chosen for lead optimization. The chemical synthesis of new molecules for each scaffold was guided by in vivo activity against *T. brucei*, cytotoxicity against mammalian cells, oral availability, microsomal stability, and permeability in the MDR1-MDCKII model of the blood brain barrier. A total of 1266 compounds were synthesized and screened for anti-trypanosomal activity. A number of the compounds demonstrated activity in the low nanomolar range and the most potent compounds had sub-nanomolar activities. Four compounds that were curative and demonstrated no overt toxicity in an acute mouse model of trypanosomiasis and had favorable brain plasma ratios in mice were selected for testing in a chronic (neurological infection) mouse model of trypanosomiasis.

Compounds from the library were tested for inhibitory activity on *T. brucei* at 3.6 µM. The screen yielded 3889 primary hits (0.6% hit rate) that inhibited growth by >50%. Primary hits from the screen were further characterized using a dose-response assay format to determine the $EC_{50}$. In parallel, the cytotoxicities of these compounds were determined against a proliferating human hepatoma cell line (Huh7). The final set of confirmed hits consisted of compounds that had $EC_{50}$<3.6 µM against *T. brucei*, as well as a limited or nonobservable Huh7 cytotoxicity ($CC_{50}$>10 µM or SI>10; SI—$CC_{50}/EC_{50}$). The final set of confirmed *T. brucei* hits consisted of 1035 inhibitors. The 1035 confirmed and selective hits could be grouped into about 115 distinct scaffolds, with 144 compounds having an $EC_{50}$ on *T. brucei* of less than 100 nM and a further 446 compounds having a $EC_{50}$ of less than 500 nM.

In vitro antitrypanosomal activities against *T. b. rhodesiense* (STIB9000) and cytotoxicities against L6 rat myoblast cells were measured following established protocols (Orhan et al., *Mar. Drugs* 8:47 (2010). During the screen, the parasite was grown in 1536-well plates in 5.5 µL of HMI-9 medium in the presence of library compounds. All wells including negative controls contained a final of 0.4% DMSO. After incubation of the plates at 37° C. for 48 h, the parasite density was determined using the CellTiter-Glo reagent (Promega), a firefly luciferase assay system that measures the amount of cellular ATP present in plate wells.

In vivo experiments were performed as previously reported with modifications to reduce the stringency of the mouse model of infection for the new chemical scaffolds (Wenzler et al., *Antimicrob. Agents Chemother.* 58:4452 (2014)). Female NMRI mice were infected intraperitoneally (i.p.) with $10^4$ STIB900 bloodstream trypanosome forms. Experimental groups of two mice were treated with 30 mg/kg i.p. test compounds on three consecutive days from day 1 to day 3 post infection (90 mg/kg i.p. total dose). A control group was infected but remained untreated. Tail blood of all mice was checked for parasitemia reduction (versus untreated control mice) 24 and 96 hours after last compound administration and thereafter twice peer week until 30 days post infection. Day of parasitemia relapse of animals was recorded to calculate the mean relapse time in days. Surviving and aparasitemic mice at day 30 were considered as cured. Mice were euthanized after 96 hours if the tail blood was not parasite free, after a parasitemia relapse was detected or on day 30 if the mouse was cured.

Metabolic stability was evaluated using liver microsomes derived from mouse and human sources. Microsomal incubations were carried out according to a protocol described previously (Wang et al., *Antimicrob. Agents Chemother.* 54:2507 (2010)) with modifications. Briefly, substrate stock solutions were prepared in DMSO and DMSO content was kept at 0.5% (v/v) in final incubations. Incubation mixtures (final volume 0.2 mL) consisted of substrate (3 µM), liver microsomes (0.5 mg/mL) from mouse (pool of 1000, CD-1 male mouse) or human (pool of 50, mixed gender) (Xeno-Tech LLC, Lenexa, Kans.) in a phosphate buffer (100 mM, pH 7.4) containing 3.3 mM $MgCl_2$. After a 5-minute pre-equilibration period at 37° C., reactions (in triplicate) were initiated by adding the NADPH cofactor (1 mM). For NADPH-independent reactions, the cofactor was replaced with water. Aliquots (10 µl) of the reaction mixtures were removed at 0, 15, 30, and 60 minutes and individually mixed with 200 µL of ice-cold acetonitrile containing internal standard. The mixtures were vortex-mixed, and precipitated protein was removed by centrifugation at 2,250×g for 15 min. The supernatant fractions were dried using a 96-well microplate evaporator (Apricot Designs Inc., Covina, Calif.) under $N_2$ at 50° C. and reconstituted with 100 µL 50% methanol containing 0.1% trifluoroacetic acid before UPLC-MS/MS analysis. In vitro half-life ($t_{1/2}$) was obtained by analyzing the substrate concentration vs. incubation time curve using the one-phase exponential decay model (Graph-Pad Prism® 5.0, San Diego, Calif.).

For distribution of compounds between mouse plasma and brain, mice (in groups of 3) were injected with test compounds (5 mg/kg ip) and sacrificed at the indicated times for collection of plasma and brain. Compound was dissolved in 0.4 mL of dosing solution (7% Tween 80, 3% ethanol, 5% DMSO, 0.9% saline) for ip injections. The brains were weighed and immediately frozen, then later homogenized in acetonitrile using a Dounce homogenizer. Prior to animal studies, recovery of test compound was carried out by adding a known amount to a mouse brain in the test extraction solvent and performing the homogenization. Compound recovery was determined by liquid chromatography/tandem mass spectrometry analysis relative to a standard compound amount. Blood was taken from the same mice in heparinized capillary tubes (Fisherbrand) for determination of compound concentration in plasma. The concentration of compound in the brain was obtained by dividing the moles of compound in the brain by the brain volume (obtained from the brain weight assuming 1 g is 1 mL) and correcting for the brain vasculature volume of 2.5% by weight.

For pharmacokinetic studies, test compound was administered to mice by oral gavage followed by blood sampling at intervals of 30, 60, 120, 180, 240, and 360 min. Compound was dosed orally ay 50 mg/kg in 0.2 mL of dosing solution (7% Tween 80, 3% ethanol, 5% DMSO, 0.9% saline). Experiments were performed with groups of three mice per compound. Plasma was separated and extracted with acetonitrile for measurements of compound concentrations by liquid chromatography/tandem mass spectrometry.

For acute efficacy studies in mice, experiments were carried out using the standard operating procedure used by WHO screening centers and done in compliance with the University of Washington Institutional Animal Care and Use Committee (IACUC) approved protocol. Groups of 5 female Swiss-Webster mice (ND4 outbred, ages 6-8 weeks) were in infected on day 0 with $1\times10^4$ *T. b. rhodesiense* (strain STIB900) parasites. The test compound was administered by oral gavage at 50 mg/kg every 12 h from day 2 to day 5, for a total of 8 doses in a 200 µL volume of a vehicle consisting of DMSO (5%), Tween 80 (7%), and EtOH (3%) in physiological saline (0.9%) solution. Parasitemia was monitored via microscopic analysis of tail blood for 60 d post-infection, or until parasites were detected. Mice were removed from the experiment once parasites were detected in the blood.

For chronic efficacy, experiments were done in compliance with the University of Washington IACUC approved protocol. According to published procedures, groups of 5 mice were infected with $1\times10^4$ *T. b. brucei* (strain TREU667) at day 0 to establish a chronic infection. Treatment began on day 21 post-infection, and mice received 50 mg/kg test compound orally b.i.d. for 10 d (total of 20 doses) in a 200 µL volume of a vehicle composed of Phosal 53 MCT (60%), PEG400 (30%) and EtOH (10%). A control group received vehicle with no compound and another control group received a single intraperitoneal dose of diminazene aceturate at 10 mg/kg in water on day 21. The diminazene aceturate temporarily clears parasites from the blood, but since it does not cross the BBB, the blood is later repopulated from parasites in the CNS. Post dosing, parasitemia was monitored via microscopic examination of tail blood slides until 180 days post-infection. Mice were removed from the experiment once parasites were detected in the blood.

Example 2

Compound 1

Compound 1 was synthesized using methods known in the art. The compound provides a total polar surface area (tPSA) of 44.7, a C Log P of 4.33083 and satisfies four of the four relevant rules from the Lipinski rule of 5.

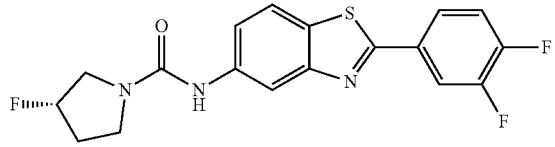

1

Compound 1 provides antimicrobial specificity for trypanosomes as shown in Table 1. The compound exhibits good stability with a microsomal half-life of 60 min in human microsomes and >60 min in mouse microsomes.

TABLE 1

Antimicrobial activity

| Organism | $EC_{50}$ | $EC_{90}$ |
|---|---|---|
| Trypanosoma brucei | 34.75 nM | 54.84 nM |
| Trypanosoma cruzi | 117.56 nM | 178.14 nM |
| Plasmodium falciparum | 16.74 μM | |
| Leishmania amazonensis | >10 μM | |

Compound 1 provides excellent blood brain barrier penetration as shown in Table 2. Compound 1 is also orally available as shown in Table 3. The combination of oral availability and blood brain barrier penetration makes the compound ideal for treatment of neurological pathogens.

TABLE 2

Brain penetration

| | |
|---|---|
| Average concentration in plasma | 2.273 ± 1.537 μM (n = 3) |
| Average concentration in brain | 9.067 ± 6.882 μM (n = 3) |
| Average brain/plasma ratio | 4.0000 ± 0.624 (n = 3) |

TABLE 3

Mouse oral pharmacokinetics (50 mg/kg dose)

| | |
|---|---|
| Average $C_{max}$ | 23.34 ± 5.22 μM (n = 3) |
| Average AUC | 132217 ± 2156 min μmol/L (n = 3) |

The pharmacokinetics of compound 1 was tested in rats after intravenous and oral administration. Two rats were administered 5 mg/kg compound 1 intravenously in a vehicle consisting of 7% Tween 80, 3% EtOH, 5% DMSO in saline. Two rats were administered 20 mg/kg compound 1 orally in a vehicle consisting of 5% DMSO, 0.5% Tween 80, 1% methylcellulose in water. The results are shown in Table 4 and FIGS. 3A-3B and 4A-4B.

TABLE 4

| | IV administration | | | Oral administration | | |
|---|---|---|---|---|---|---|
| Parameter | Rat 1 | Rat 2 | Mean ± SEM | Rat 3 | Rat 4 | Mean ± SEM |
| Measured dose (mg/kg) | 0.840 | 0.762 | 0.801 ± 0.039 (n = 2) | 2.900 | 3.040 | 2.97 ± 0.07 (n = 2) |
| Rat weight (kg) | 0.156 | 0.160 | 0.158 ± 0.002 (n = 2) | 0.145 | 0.150 | 0.147 ± 0.003 (n = 2) |
| Apparent $T_{1/2}$ (min) for steady state | 88.524 | 104.811 | 96.67 ± 8.14 (n = 2) | — | — | — |
| Apparent $T_{1/2}$ (min) for terminal phase | 88.517 | 104.814 | 96.67 ± 8.15 (n = 2) | — | — | — |
| Plasma CL (mL/min/kg) | 10.306 | 8.384 | 9.35 ± 0.96 (n = 2) | — | — | — |
| Plasma $V_z$ (L/kg) | 0.882 | 0.639 | 0.76 ± 0.122 (n = 2) | — | — | — |
| Plasma $V_{ss}$ (L/kg) | 1.316 | 1.301 | 1.309 ± 0.01 (n = 3) | — | — | — |
| $C_{max}$ (μM) | 12.083 | 11.263 | 11.67 ± 0.41 (n = 2) | 7.310 | 10.522 | 8.92 ± 1.61 (n = 2) |
| $T_{max}$ (min) | 5 | 5 | 5 ± 0 (n = 2) | 480 | 360 | 420 ± 60 (n = 2) |
| $AUC_{0-inf}$ (h* μM) | 1384.50 | 1504.15 | 1444.32 ± 59.83 (n = 2) | 5769.10 | 6766.41 | 6267.75 ± 498.66 (n = 2) |
| Apparent BA (%) | | | | 110.29 | 123.40 | 116.85 ± 6.55 (n = 2) |

The efficacy of compound 1 was tested in both acute and chronic models of T. brucei infection. In the acute model (organisms in the bloodstream only), 5 of 5 mice were cured. In the chronic model (organisms in the bloodstream and the central nervous system), again 5 of 5 mice were cured, confirming the ability of compound 1 to penetrate the blood brain barrier and accumulate in therapeutically effective amounts.

The effects of fluorination and stereochemistry on the biological properties of compound 1 were tested by synthesizing the following compounds of Formula VI. The stability, oral PK, and brain penetration of the three compounds are shown in Table 5.

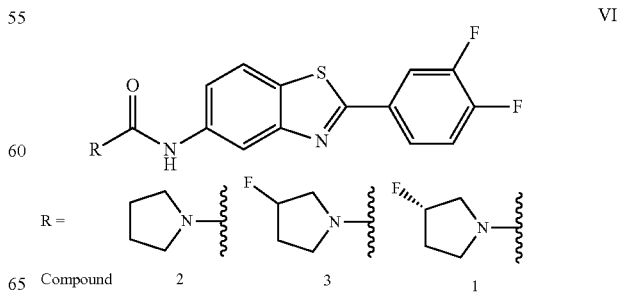

VI

TABLE 5

Effects of fluorination and stereochemistry

| | Compound | | |
|---|---|---|---|
| | 2 | 3 | 1 |
| Microsome $t_{1/2}$ (min) | | | |
| Human | >60 | >60 | 60 |
| Mouse | 13.8 | 60 | >60 |
| Mouse oral PK | | | |
| Average $C_{max}$ (μM) | 2.00 ± 0.82 (n = 3) | 10.03 ± 1.10 (n = 3) | 23.34 ± 5.22 (n = 3) |
| Average AUC (min * μmol/L) | 408 ± 95 (n = 3) | 3847 ± 466 (n = 3) | 13217 ± 2156 (n = 3) |
| $T_{max}$ (min) | 60 | 60 | 120 |
| $T_{last}$ (min) | 480 | 480 | 1440 |
| Mouse brain penetration (60 min) | | | |
| Average concentration in plasma (μM) | 2.607 ± 1.259 (n = 3) | 2.777 ± 0.652 (n = 3) | 2.273 ± 1.537 (n = 3) |
| Average concentration in plasma (μM) | 4.253 ± 1.200 (n = 3) | 4.223 ± 0.974 (n = 3) | 9.067 ± 6.882 (n = 3) |
| Average brain/plasma ratio | 1.807 ± 0.793 (n = 3) | 1.52 ± 0.0416 (n = 3) | 4.000 ± 0.624 (n = 3) |

The effect of stereochemistry on antimicrobial activity was assessed by comparing the activity of the (S)-enantiomer (compound 1) with the racemic compound (compound 3) and the (R)-enantiomer (compound 4). As shown in Table 6, the racemic compound (compound 3) has strong antimicrobial activity while the (S)-enantiomer (compound 1) is even more active. The (R)-enantiomer (compound 4) is less active.

TABLE 6

Antimicrobial activity

| Organism | Compound 3 (racemic) | Compound 4 ((R)-enantiomer) | Compound 1 ((S)-enantiomer) |
|---|---|---|---|
| T. brucei $EC_{50}$ (nM) | 51.9 | 325.6 | 34.8 |
| T. cruzi $EC_{50}$ (nM) | 91.9 | 491.4 | 58.5 |

Example 3

Analogs of Compound 1

Analogs of compound 1 were prepared and tested for antimicrobial activity and brain penetration. First, analogs in which $R_1$ of the compound of formula II was fixed as N-pyrrolidinyl were tested. The results are shown in Table 7.

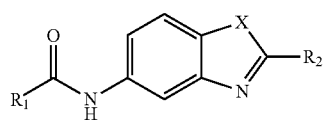

II

TABLE 7

| | | | T. brucei Average $EC_{50}$ (nM) | Average [compound] plasma (μM) | Average [compound] brain (μM) | Average brain/plasma ratio |
|---|---|---|---|---|---|---|
| Compound | $R_2$ | X | Brain penetration (groups of 3 mice) | | | |
| 2 | 3,4-di-F-Ph | S | 91.8 | 2.61 ± 1.26 | 4.25 ± 1.20 | 1.81 ± 0.793 |
| 5 | 2,3-di-F-Ph | S | 183 | 1.30 ± 0.703 | 2.31 ± 1.29 | 1.76 ± 0.055 |
| 6 | 3-F-Ph | S | 158 | 2.22 ± 0.798 | 2.28 ± 0.92 | 1.01 ± 0.064 |
| 7 | Ph | S | 325 | 3.40 ± 0.569 | 4.24 ± 1.21 | 1.24 ± 0.272 |
| 8 | Ph | O | 5252 | 0.270 ± 0.062 | 0.397 ± 0.13 | 1.577 ± 0.839 |

The data show that compound 2 achieves the highest compound concentration in the brain and the highest brain/plasma ratio. When the fluorination pattern is changed there is a decrease in brain compound concentration and/or brain/plasma ratio. The benzothiazole compounds are better than the benzoxazole compound with respect to both potency and brain penetration. However, it is noteworthy that all of the compounds are able to penetrate the blood brain barrier. Further, there is a reasonably good correlation between potency and brain penetration.

Another set of compounds in which $R_2$ of the compound of formula II was fixed as 3,4-difluorophenyl, X was fixed as S, and $R_1$ was varied were tested. The results are shown in Table 8.

TABLE 8

| Compound | $R_1$ | T. brucei $EC_{50}$ (nM) | Brain penetration (groups of 3 mice) | | |
|---|---|---|---|---|---|
| | | | Average [compound] plasma (µM) | Average [compound] brain (µM) | Average brain/plasma ratio |
| 1 | (S)-3-F—N-pyrrolidinyl | 34.8 | 2.27 ± 1.54 | 9.07 ± 6.88 | 4.00 ± 0.624 |
| 2 | N-pyrrolidinyl | 91.8 | 2.61 ± 1.26 | 4.25 ± 1.20 | 1.81 ± 0.793 |
| 3 | (±)-3-F—N-pyrrolidinyl | 51.9 | 3.26 ± 0.630[a] | 5.48 ± 0.683[a] | 2.11 ± 0.669 |
| 4 | (R)-3-F—N-pyrrolidinyl | 326 | 1.20 ± 0.467 | 6.35 ± 3.91 | 4.86 ± 1.83 |
| 9 | 3,3-di-F—N-pyrrolidinyl | 934 | 2.81 ± 0.784 | 21.7 ± 3.40 | 7.92 ± 1.20 |
| 10 | 3-$CF_3$—N-pyrrolidinyl | 1695 | 4.15 ± 2.37 | 1.97 ± 1.06 | 0.477 ± 0.090 |
| 11 | 3-($NMe_2$)—N-pyrrolidinyl | 1705 | 0.780 ± 0.350 | 3.00 ± 1.38 | 3.80 ± 0.57 |
| 12 | N-piperidinyl | 223 | 2.52 ± 0.320 | 1.29 ± 0.27 | 0.510 ± 0.040 |
| 13 | 4-F—N-piperidinyl | 341 | 2.51 ± 0.352 | 2.53 ± 0.43 | 1.01 ± 0.140 |
| 35 | (R,R)-3,4-di-F—N-pyrrolidinyl | 114 | 2.19 ± 0.424 | 16.2 ± 2.88 | 7.71 ± 1.63 |

[a]Average values ± SEM of 6 mice.

The data show that brain penetration is enhanced by fluorination of both pyrrolidone and piperidine rings. The best penetration was achieved with compound 9. In these analogs, there is less correlation between the best potency and best brain penetration. For example, the racemic compound 2 has high potency and good brain penetration, but the inactive (R)-enantiomer has better brain penetration. Compound 10 exhibits decreased brain penetration. Compound 11 exhibits a good brain/plasma ratio even though it has a lower concentration in the brain. In general, the piperidine compounds are a little less potent and exhibit decreased brain penetration compared to the corresponding pyrrolidine compounds. However, the piperidine compounds are still potent (submicromolar $EC_{50}$).

The identification of compounds with superior brain penetration, such as compounds 1, 4, and 9, suggest that these compounds may be used as the basis for further identification of therapeutic compounds with enhanced brain penetration suitable for the treatment of neurological pathogens.

Additional compounds were synthesized and tested for efficacy against T. b. brucei as described above. The results are shown in Table 9.

TABLE 9

| Compound | Core | $R_1$ | $R_2$ | T. brucei EC50 (nM) | T. brucei EC90 (nM) |
|---|---|---|---|---|---|
| 1 | A | (S)-3-fluoropyrrolidin-1-yl | 3,4-difluorophenyl | 34.8 | 54.8 |
| 2 | A | pyrrolidin-1-yl | 3,4-difluorophenyl | 91.8 | 181 |
| 3 | A | 3-fluoropyrrolidin-1-yl | 3,4-difluorophenyl | 51.9 | 91.9 |
| 4 | A | (R)-3-fluoropyrrolidin-1-yl | 3,4-difluorophenyl | 326 | 491 |
| 5 | A | pyrrolidin-1-yl | 2,3-difluorophenyl | 183 | 394 |
| 6 | A | pyrrolidin-1-yl | 3-fluorophenyl | 158 | 391 |
| 7 | A | pyrrolidin-1-yl | phenyl | 325 | 817 |
| 8 | B | pyrrolidin-1-yl | phenyl | 5250 | >10000 |
| 9 | A | 3,3-difluoropyrrolidin-1-yl | 3,4-difluorophenyl | 934 | 1660 |
| 10 | A | 3-(trifluoromethyl)pyrrolidin-1-yl | 3,4-difluorophenyl | 1690 | 4880 |
| 11 | A | 3-(dimethylamino)pyrrolidin-1-yl | 3,4-difluorophenyl | 1700 | 1950 |
| 12 | A | piperidin-1-yl | 3,4-difluorophenyl | 223 | 282 |
| 13 | A | 4-fluoropiperidin-1-yl | 3,4-difluorophenyl | 341 | 596 |
| 14 | C | phenyl | phenyl | >10000 | >10000 |
| 15 | B | phenyl | phenyl | >10000 | >10000 |
| 16 | B | piperidin-1-yl | phenyl | 2800 | 9300 |
| 17 | A | phenyl | phenyl | 2380 | 7740 |
| 18 | A | thiophen-2-yl | phenyl | 882 | 2130 |
| 19 | A | thiophen-3-yl | phenyl | 1570 | 2490 |
| 20 | A | thiazol-2-yl | phenyl | 5860 | >10000 |
| 21 | A | thiazol-4-yl | phenyl | >10000 | >10000 |
| 22 | A | thiazolidin-3-yl | phenyl | 1240 | 2380 |
| 23 | A | piperidin-1-yl | phenyl | 366 | 809 |
| 24 | A | 1,2,3,6-tetrahydropyridin-1-yl | phenyl | 1120 | 1350 |
| 25 | A | phenyl | 4-fluorophenyl | 1920 | 3000 |
| 26 | A | pyrroldin-1-yl | 4-fluorophenyl | 375 | 895 |
| 27 | A | piperidin-1-yl | 4-fluorophenyl | 427 | 737 |
| 28 | A | phenyl | 3-fluorophenyl | 1780 | 3620 |
| 29 | A | piperidin-1-yl | 3-fluorophenyl | 174 | 602 |
| 30 | A | 4-methylpiperazin1-yl | 3-fluorophenyl | 3150 | 7550 |
| 31 | A | piperazin-1,4-diyl | 3-fluorophenyl | >20000 | >20000 |
| 32 | A | pyrrolidin-1-yl | 2-fluorophenyl | 983 | 1240 |
| 33 | A | piperidin-1-yl | 2-fluorophenyl | 935 | 1140 |
| 34 | A | pyrrolidin-1-yl | 2,4-difluorophenyl | 929 | 1480 |
| 35 | A | (3R,4R)-3,4-difluoropyrrolidin-1-yl | 3,4-difluorophenyl | 114 | 747 |
| 36 | A | 3-cyanopyrrolidin-1-yl | 3,4-difluorophenyl | 2850 | 4670 |
| 37 | A | 3-aminopyrrolidin-1-yl | 3,4-difluorophenyl | 2320 | 2720 |
| 38 | A | 3-hydroxypyrrolidin-1-yl | 3,4-difluorophenyl | 7680 | 13600 |

TABLE 9-continued

| Compound | Core | R₁ | R₂ | T. brucei EC50 (nM) | T. brucei EC90 (nM) |
|---|---|---|---|---|---|
| 39 | A | 3-methoxypyrrolidin-1-yl | 3,4-difluorophenyl | 3050 | 4590 |
| 40 | A | 4,4-difluoropiperidin-1-yl | 3,4-difluorophenyl | 2980 | 4170 |

Core Structures:

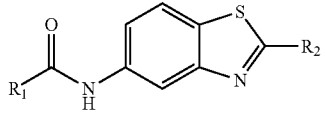

A

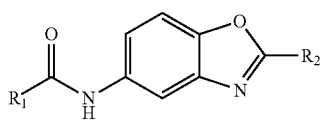

B

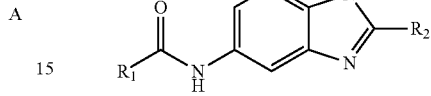

C

The compounds were tested for efficacy against *T. cruzi* as described above. The results are shown in Table 10. The compounds have good potency, with EC$_{50}$ values below 2 μM. The similarity score (Tanimoto coefficient) was calculated using Collaborative Drug Discovery software (ChemAxon).

TABLE 10

| Compound | Structure | Similarity Score (%) | T.cruzi EC$_{50}$ (nM) | T.cruzi EC$_{90}$ (nM) |
|---|---|---|---|---|
| 1 | 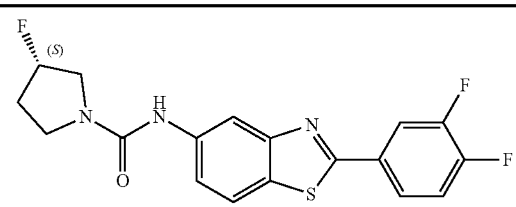 | 100 | 117.56 | 178.14 |
| 2 | 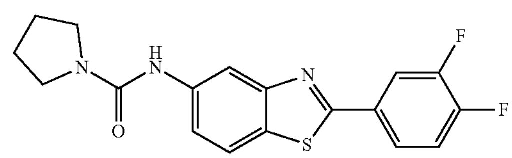 [SMILES: O=C(Nc1ccc2sc(-c3ccc(F)c(F)c3)nc2c1)N1CCCC1] | 94 | 339 | 483.31 |
| 3 | 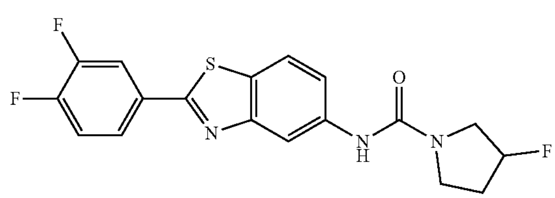 [SMILES: O=C(Nc1ccc2sc(-c3ccc(F)c(F)c3)nc2c1)N1CCC(F)C1] | 100 | 177.17 | 524.54 |
| 4 | 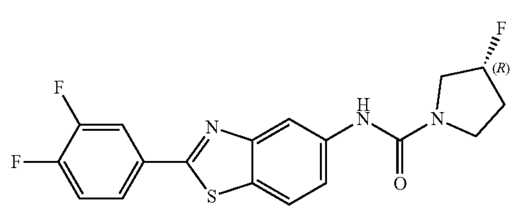 | 100 | 967.58 | 1539.42 |
| 5 | 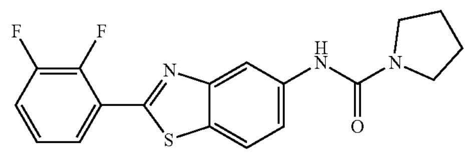 [SMILES: O=C(Nc1ccc2sc(-c3cccc(F)c3F)nc2c1)N1CCCC1] | 89 | 578.45 | 664.73 |

TABLE 10-continued

| Compound | Structure | Similarity Score (%) | T.cruzi EC$_{50}$ (nM) | T.cruzi EC$_{90}$ (nM) |
| --- | --- | --- | --- | --- |
| 6 | 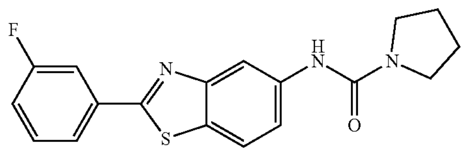 | 92 | 631.26 | 697.31 |
| 7 | 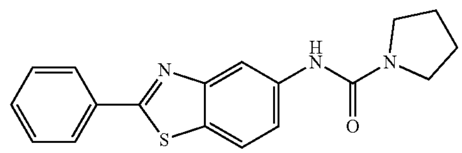 [SMILES: O=C(Nc1ccc2sc(-c3ccccc3)nc2c1)N1CCCC1] | 86 | 563.85 | 861.39 |
| 12 | 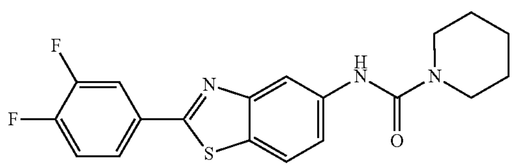 [SMILES: O=C(Nc1ccc2sc(-c3ccc(F)c(F)c3)nc2c1)N1CCCCC1] | 92 | 428.62 | 911.68 |
| 13 | 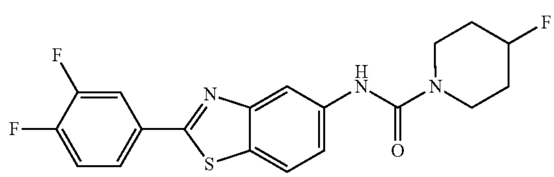 [SMILES: O=C(Nc1ccc2sc(-c3ccc(F)c(F)c3)nc2c1)N1CCC(F)CC1] | 96 | 1799.38 | 1994.23 |
| 23 | 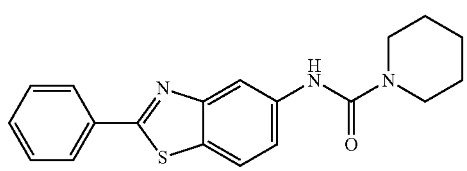 [SMILES: O=C(Nc1ccc2sc(-c3ccccc3)nc2c1)N1CCCCC1] | 85 | 825.97 | 1072.87 |
| 26 | 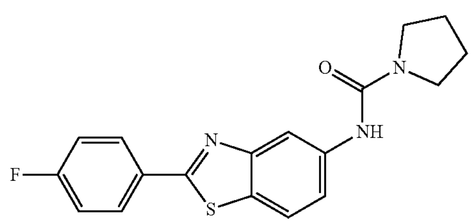 [SMILES: O=C(Nc1ccc2sc(-c3ccc(F)cc3)nc2c1)N1CCCC1] | 90 | 666.26 | 802.24 |
| 27 | 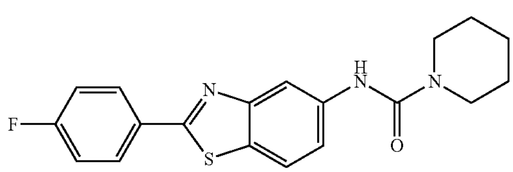 [SMILES: O=C(Nc1ccc2sc(-c3ccc(F)cc3)nc2c1)N1CCCCC1] | 89 | 1673.48 | 1949.26 |
| 29 | 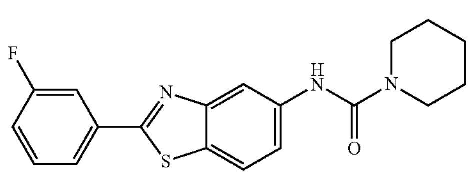 [SMILES: O=C(Nc1ccc2sc(-c3cccc(F)c3)nc2c1)N1CCCCC1] | 91 | 320.06 | 503.33 |
| 32 | 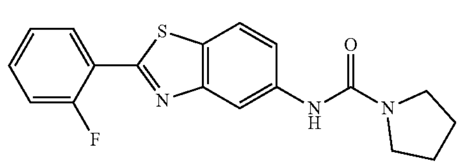 [SMILES: O=C(Nc1ccc2sc(-c3ccccc3F)nc2c1)N1CCCC1] | 86 | 1233.1 | 1987.31 |

TABLE 10-continued

| Compound | Structure | Similarity Score (%) | T.cruzi EC$_{50}$ (nM) | T.cruzi EC$_{90}$ (nM) |
|---|---|---|---|---|
| 33 | 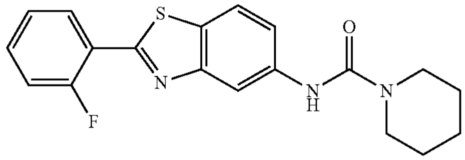 [SMILES: O=C(Nc1ccc2sc(-c3ccccc3F)nc2c1)N1CCCCC1] | 86 | 842.52 | 1123.6 |
| 34 | 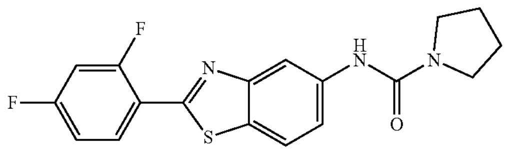 [SMILES: O=C(Nc1ccc2sc(-c3ccc(F)cc3F)nc2c1)N1CCCC1] | 87 | 1728.35 | 2022.66 |
| 35 | 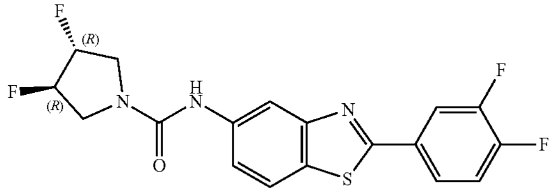 | 99 | 561.64 | 651.88 |

Cytotoxicity and Selectivity.

All compounds with EC$_{50}$ values below 1 μM (except 34) were tested for toxicity against human lymphocytes CRL-8155 and human hepatocytes HepG2 (Table 11). Most of the compounds (including 1) exhibited no detectable toxicity to either cell line. Only compounds 2 and 35 had detectable toxicity to the CRL-8155 cells (EC$_{50}$=33.9 and 27.1 μM respectively), and none had detectable toxicity to the HepG2 cells. The selectivity of each compound for the parasite over each of the two cell lines was calculated. Compound 1 exhibited a selectivity index above 1000 against either cell line. Thirteen analogues (2, 3, 4, 5, 6, 7, 12, 13, 23, 26, 27, 29, and 35) had selectivity indices above 100 against either cell line. Within this group, compound 28 had a selectivity index above 500 in the CRL-8155 assay, while 54 and 55 had selectivity indices above 500 in the HepG2 assay.

TABLE 11

Cytotoxicity and selectivity of select compounds

| compd | T. b. brucei EC50 (μM) | CRL-8155[a,b] EC50 (μM)[e] | CRL-8155[a,b] EC90 (μM)[f] | CRL-8155[a,b] SI[g] | HepG2[c,d] EC50 (μM)[e] | HepG2[c,d] EC90 (μM)[f] | HepG2[c,d] SI[g] |
|---|---|---|---|---|---|---|---|
| 1 | 0.0348 | >50 | >50 | >1437 | >50 | >50 | >1437 |
| 2 | 0.0918 | 33.9 | >50 | 369 | >50 | >50 | >545 |
| 3 | 0.0519 | >50 | >50 | >963 | >50 | >50 | >963 |
| 4 | 0.326 | >50 | >50 | >153 | >50 | >50 | >153 |
| 5 | 0.183 | >50 | >50 | >273 | >50 | >50 | >273 |
| 6 | 0.158 | >50 | >50 | >316 | >50 | >50 | >316 |
| 7 | 0.325 | >50 | >50 | >154 | >50 | >50 | >154 |
| 9 | 0.934 | >50 | >50 | >54 | >50 | >50 | >54 |
| 12 | 0.223 | >50 | >50 | >224 | >50 | >50 | >224 |
| 13 | 0.341 | >50 | >50 | >147 | >50 | >50 | >147 |
| 18 | 0.882 | >50 | >50 | >57 | >50 | >50 | >57 |
| 23 | 0.366 | >50 | >50 | >137 | >50 | >50 | >137 |
| 26 | 0.375 | >50 | >50 | >133 | >50 | >50 | >133 |
| 27 | 0.427 | >50 | >50 | >117 | >50 | >50 | >117 |
| 29 | 0.174 | >50 | >50 | >287 | >50 | >50 | >287 |
| 32 | 0.983 | >50 | >50 | >51 | >50 | >50 | >51 |
| 33 | 0.935 | >50 | >50 | >53 | >50 | >50 | >53 |
| 35 | 0.114 | 27.1[h] | >50 | >238 | >50 | >50 | >439 |
| penth | 0.00105 | 45.4 | >100 | >43200 | >100 | >100 | >93000 |

[a]Human lymphoblasts (CRL-8155).
[b]Control for CRL-8155 EC$_{50}$ assay average ± SEM: quinacrine (4.23 μM ± 0.97 μM (n = 7); EC$_{90}$ assay average ± SEM: quinacrine (9.94 μM ± 2.41 μM (n = 7).
[c]Human hepatocytes (HepG2).
[d]Control for HepG2 EC$_{50}$ assay average ± SEM: quinacrine (10.44 μM ± 1.39 μM (n = 7); EC$_{90}$ assay average ± SEM: quinacrine (18.23 μM ± 2.34 μM (n = 7).
[e]Concentration of compound required to inhibit growth by 50% (EC$_{50}$) of mammalian cell lines.
[f]Concentration of compound required to inhibit growth by 90% (EC$_{90}$) of mammalian cell lines.
[g]Selectivity index expressed as the ratio EC$_{50}$ (cell line)/EC$_{50}$ (T. b. brucei), rounded to the nearest integer.
[h]Pentamidine Metabolic Stability.

Select compounds were assayed for stability to mouse and human liver microsomes (Table 12). All compounds that were tested had half-lives greater than 10 min in the mouse microsomes and at least 30 min (except for 29) in the human microsomes.

TABLE 12

Stability of select compounds to mouse and human liver microsomes

| Compound | T. b. brucei EC$_{50}$ (μM) | Mouse microsomes t$_{1/2}$ (min)[a,b] | Human microsomes t$_{1/2}$ (min)[a,c] |
|---|---|---|---|
| 1 | 0.0348 | >60 (73%) | >60 (53%) |
| 2 | 0.0918 | 14 | >60 (66%) |
| 3 | 0.0519 | >60 (52%) | >60 (99%) |
| 6 | 0.158 | 12 | 37 |

TABLE 12-continued

Stability of select compounds to mouse and human liver microsomes

| Compound | T. b. brucei EC$_{50}$ (μM) | Mouse microsomes t$_{1/2}$ (min)$^{a,b}$ | Human microsomes t$_{1/2}$ (min)$^{a,c}$ |
|---|---|---|---|
| 7 | 0.325 | 18 | 30 |
| 15 | >10 | 17 | 60 |
| 16 | 2.80 | 11 | >60 (77%) |
| 17 | 2.38 | 50 | >60 (53%) |
| 23 | 0.366 | 17 | >60 (62%) |
| 29 | 0.174 | 11 | 8.9 |
| 35 | 0.114 | >60 (67%) | >60 (96%) |

$^a$Microsome reactions were incubated at 37° C. with KH$_2$PO$_4$ (0.16M), NADPH (1 mM), of microsomes (0.5 mg/mL), and test compounds (1.5 μM). Numbers in parentheses are percentages of compound remaining after 5 min (where t$_{1/2}$ < 5 min) or after 60 min (where t$_{1/2}$ > 60 min)
$^b$Control for mouse microsome assay average ± SEM: dextromethorphan (7.79 min. ± 1.40 min, n = 7) and testosterone (5.26 min. ± 0.637 min, n = 7).
$^c$Control for human microsome assay average ± SEM: dextromethorphan (39.15 ± 5.13 min, n = 7) and testosterone (22.7 ± 5.89 min, n = 6).
$^d$Below limit of detection.

Mouse Oral PK.

Compounds 1, 2, 3, and 35 were administered to groups of three mice in single doses of 50 mg/kg by oral gavage in a dosing vehicle consisting of Tween 80 (7%), EtOH (3%), and DMSO (5%) in 0.9% sodium chloride solution (Table 13). Compound 1 (the most potent in vitro) clearly showed the highest blood levels of the four compounds tested in the same vehicle, with a maximum blood concentration of 23.3 μM and an AUC of 13,216 min·μM. Compound 35 had a lower C$_{max}$ but a similar AUC compared to 1. Less than 1% of the C$_{max}$ of 1 remained at the 24 h time point, compared to 34% of the Cmax of 35. More than the 17% of the C$_{max}$ of 35 remained at the 32 h time point. Compound 1 gave a PK profile similar to that obtained using the original vehicle when administered in a vehicle consisting of Phosal 53 MCT (60%), PEG400 (30%), and EtOH (10%); however, the use of a vehicle consisting of methylcellulose cP 400 (0.5%) and Tween 80 (0.5%) in water resulted in a lower Cmax and AUC values.

TABLE 13

Oral Pharmacokinetics of Compounds 1, 2, 3, and 35 in Mice

| Compound | C$_{max}$ (μM)$^a$ | AUC$_{0\ min-\infty}$ (min × μM)$^a$ |
|---|---|---|
| 1$^b$ | 23.34 ± 3.02 | 13254 ± 1237 |
| 1$^c$ | 18.55 ± 5.54 | 14673 ± 2833 |
| 1$^d$ | 8.54 ± 0.41 | 6352 ± 469 |
| 2$^b$ | 2.01 ± 0.46 | 443.3 ± 43.07 |
| 3$^b$ | 10.04 ± 0.65 | 6459.4 ± 481.8 |
| 35$^b$ | 10.96 ± 0.58 | 13515 ± 224.6 |

$^a$Average values ± SEM of 3 mice each given a single dose at 50 mg/kg by oral gavage.
$^b$Dosing vehicle consisted of Tween 80 (7%), EtOH (3%), and DMSO (5%) in 0.9% sodium chloride solution.
$^c$Dosing vehicle consisted of Phosal 53 MCT(60%), PEG400 (30%) and EtOH (10%).
$^d$Dosing vehicle consisted of methylcellulose cP 400 (0.5%) and Tween 80 (0.5%) in water.

Brain Penetration.

Brain penetration studies (Table 14) were initially performed upon compounds 1, 2, and 3, but were expanded to include other compounds in order to explore the SAR of brain penetration. Groups of three mice were given single 5 mg/kg ip doses of the test compounds and were sacrificed 1 h post-dose.

TABLE 14

Brain Penetration of Select Compounds in Mice at One Hour Post-Dose

| Compound | [compound]$_{Plasma}$ (μM)$^a$ | [compound]$_{Brain}$ (μM)$^a$ | Brain/plasma ratio |
|---|---|---|---|
| 1 | 2.27 ± 0.888 | 9.07 ± 3.973 | 4.00 ± 0.361 |
| 2 | 2.61 ± 0.727 | 4.25 ± 0.693 | 1.81 ± 0.458 |
| 3 | 3.26 ± 0.630$^b$ | 5.48 ± 0.683$^b$ | 2.11 ± 0.669 |
| 4 | 1.20 ± 0.270 | 6.35 ± 2.257 | 4.86 ± 1.055 |
| 5 | 1.3 ± 0.406 | 2.31 ± 0.746 | 1.76 ± 0.032 |
| 6 | 2.22 ± 0.461 | 2.28 ± 0.532 | 1.01 ± 0.037 |
| 7 | 3.403 ± 0.328 | 4.24 ± 0.698 | 1.24 ± 0.157 |
| 8 | 0.270 ± 0.036 | 0.397 ± 0.077 | 1.58 ± 0.484 |
| 9 | 2.81 ± 0.452 | 21.7 ± 1.96 | 7.92 ± 0.693 |
| 10 | 4.15 ± 1.368 | 1.97 ± 0.612 | 0.477 ± 0.052 |
| 11 | 0.780 ± 0.202 | 3.00 ± 0.796 | 3.80 ± 0.331 |
| 12 | 2.52 ± 0.185 | 1.29 ± 0.156 | 0.510 ± 0.023 |
| 13 | 2.51 ± 0.203 | 2.52 ± 0.248 | 1.01 ± 0.081 |
| 35 | 2.19 ± 0.424 | 16.2 ± 2.88 | 7.71 ± 1.63 |

$^a$Average values ± SEM of 3 mice each given a single ip dose at 5 mg/kg in vehicle consisting of Tween 80 (7%), EtOH (3%), and DMSO (5%) in 0.9% sodium chloride solution.
$^b$Average values ± SEM of 6 mice.

The brain and plasma concentrations of compound 1 were studied in a time-course experiment following oral dosing at 50 mg/kg (Table 15). The data show that 1 partitions to the brain compartment with brain to plasma ratios (BPRs) of 1.48, 4.43, and 5.48 at 1, 4, and 8 h post-dose, respectively. At 24 h, the plasma concentrations are undetectable and brain levels are down to sub-micromolar concentrations. Compared to the previous experiment (Table 14), the BPR ratio for 1 is lower at 1 h post-dose (1.48 vs. 4.0) probably due to the oral route of administration (as opposed to the ip route used before) leading to slower systemic absorption and distribution. The time-course experiment demonstrates that brain concentrations of 1 are sustained at high levels for at least 8 h post-dose, and help account for the successful results in the late-stage efficacy model discussed below.

TABLE 15

Brain Time-course Study of Compound 1.

| Time (h) | [compd]$_{Plasma}$ (μM)$^a$ | [compd]$_{Brain}$ (μM)$^a$ | Brain/plasma ratio |
|---|---|---|---|
| 1 | 27.14 ± 9.91 | 38.23 ± 13.51 | 1.48 ± 0.16 |
| 4 | 10.25 ± 2.21 | 45.2 ± 10.4 | 4.43 ± 0.3 |
| 8 | 8.97 ± 1.05 | 48.08 ± 2.47 | 5.48 ± 0.6 |
| 24 | <LLQ$^b$ | 0.28 ± 0.13 | — |
| C$_{max}$ (μM) | 27.39 ± 9.67 | 54.84 ± 4.64 | |
| AUC$_{0\ min-\infty}$ (min × μM) | 10798 ± 1975 | 43116.8 ± 2304 | |

$^a$Average concentration ± SEM of 3 mice at the stated time point after each mouse received a single oral dose at 50 mg/kg in vehicle consisting of Tween 80 (7%), EtOH (3%), and DMSO (5%) in 0.9% sodium chloride solution.
$^b$LLQ (lower limit of quantitation) is 0.010 μM.

In Vivo Efficacy.

Based upon its promising in vitro activity, cytotoxicity, metabolic stability, PK, and brain penetration data, compound 1 was selected as a candidate for in vivo efficacy studies. An acute model was employed (requiring 60 days to complete) followed by a chronic model (requiring 180 days to complete).

In a model of the acute phase of HAT, five mice infected with T. b. rhodesiense STIB900 were given the test compound at 50 mg/kg po b.i.d.×4 days, beginning 2 days post-infection. Efficacy PK blood samples were collected from three of the five mice prior to dose 7, and at 1 h and 6 h post-dose. Average plasma levels of the test compound were 9.1±7.6 µM (pre-dose), 18.6±7.2 µM (1 h), and 15.0±4.2 µM (6 h). Compound 1 attained 5/5 cures as determined by the absence of detectable parasitemia in any of the treated mice 60 days post-infection (FIG. 1). All mice receiving only vehicle showed high parasitemia on the last day of dosing, with all concentrations >1.5×10$^7$ parasites/ml of blood, and were euthanized.

Figure 2:
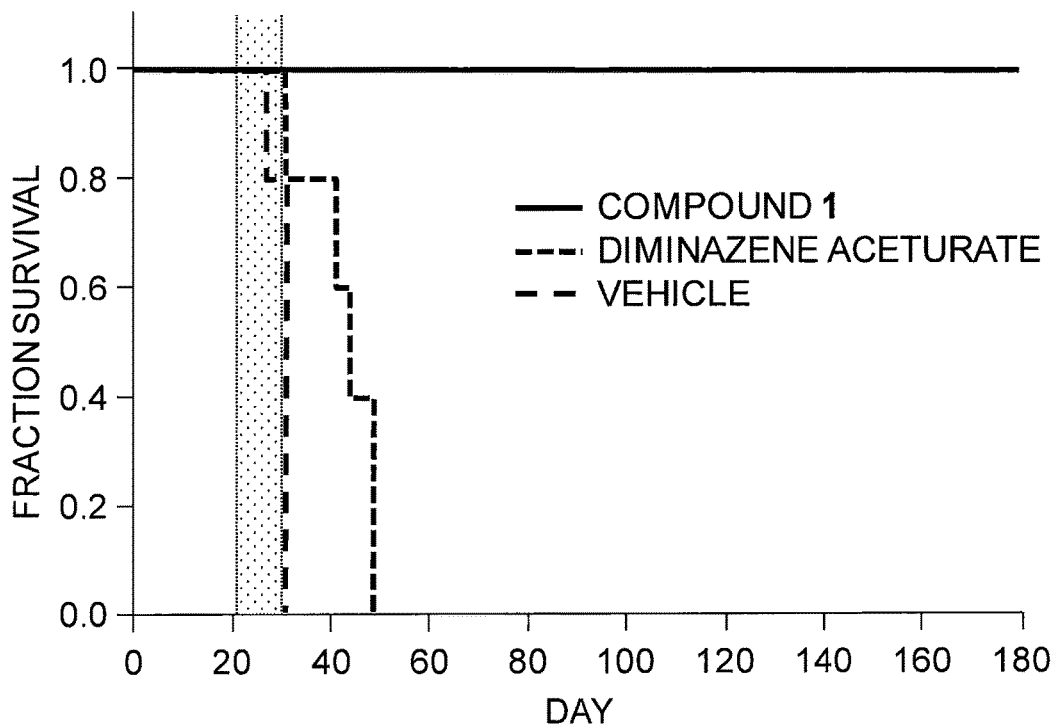
FIG. 2 shows mouse efficacy model of chronic T. brucei infection. All mice were infected with T. b. brucei TREU667 strain on day 0. Groups of five mice were treated with compound 1 (50 mg/kg by oral gavage b.i.d.) or vehicle from day 21-30 (gray-shaded area). A control group received a single dose of diminazene on day 21. Mice were monitored for parasitemia in tail blood samples through day 180 post-infection.
Figure 3A:
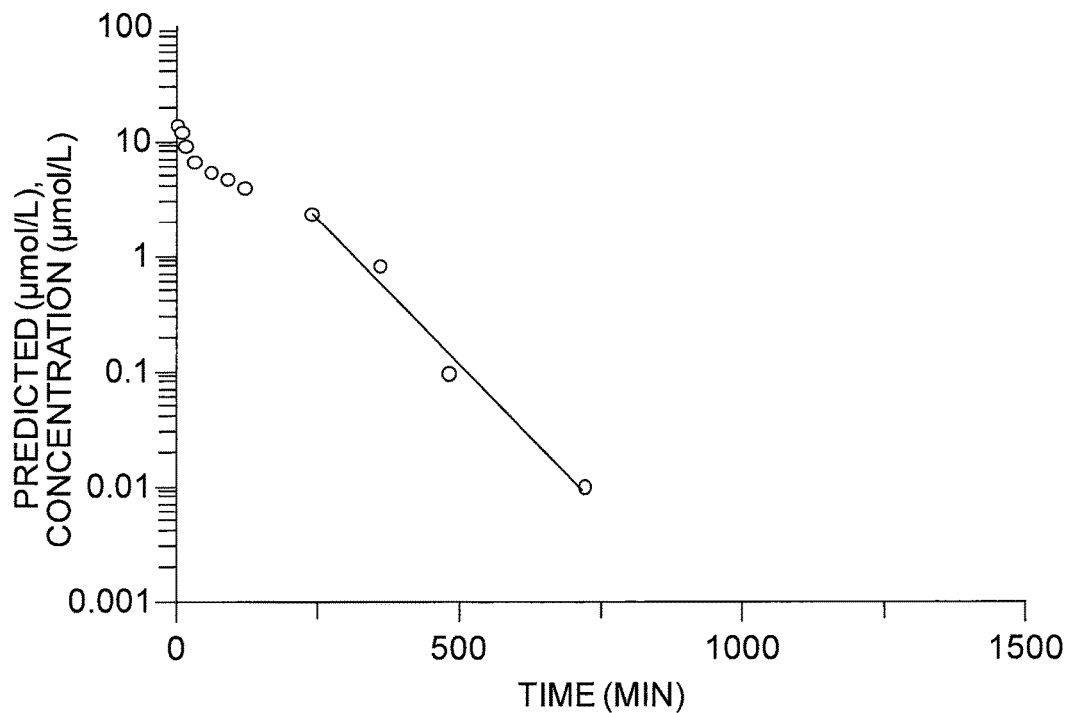
FIGS. 3A-3B show the pharmacokinetics of compound 1 in two individual rats after intravenous administration.
Figure 3B:
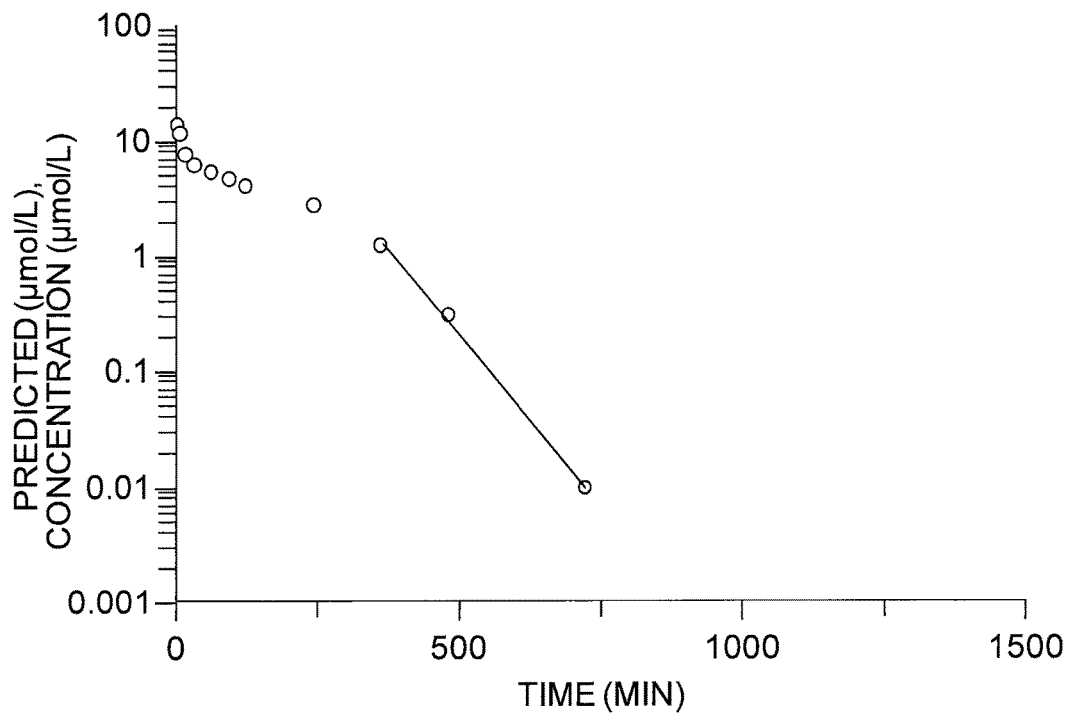
Figure 4A:
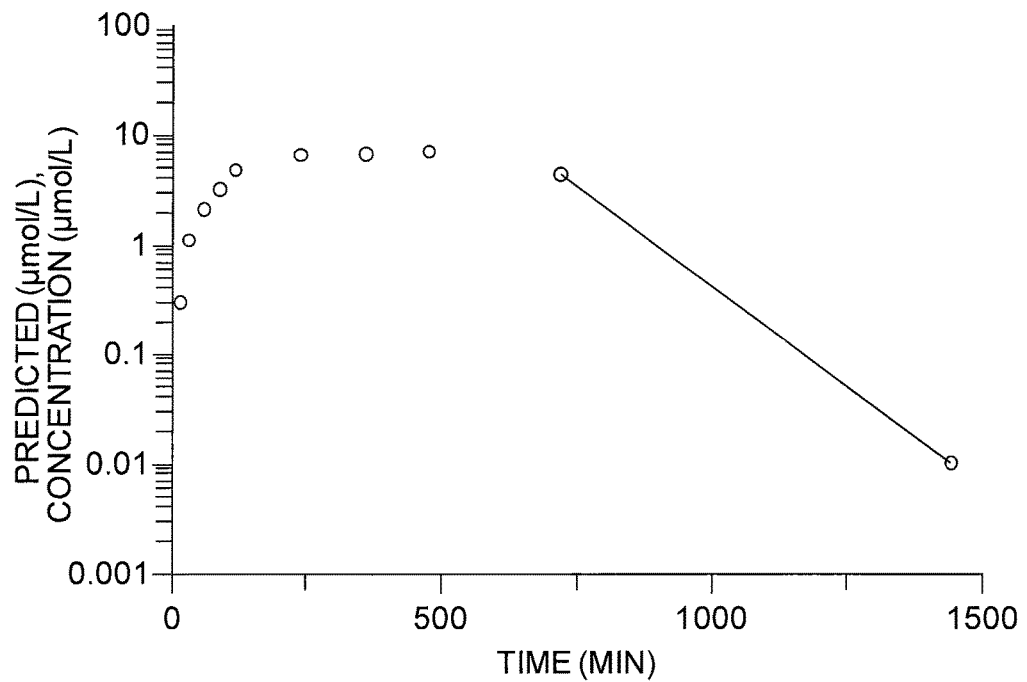
FIGS. 4A-4B show the pharmacokinetics of compound 1 in two individual rats after oral administration.
Figure 4B:
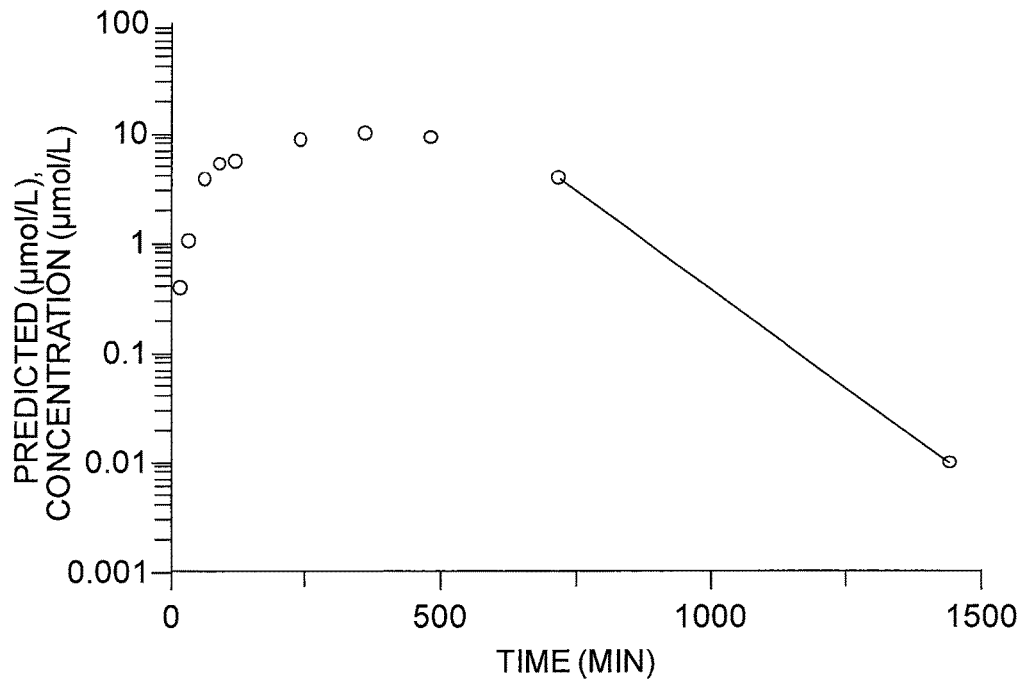

In a model of the chronic phase of HAT, compound 1 was administered to five mice infected with *T. b. brucei* TREU667 at 50 mg/kg/po b.i.d.×10 days, beginning 21 days post-infection. This dose was chosen since earlier PK studies demonstrated good plasma exposure at 50 mg/kg (Table 13). Efficacy PK blood samples were collected from three of the five mice prior to dose 15, and at 1 h and 6 h post-dose. Average plasma levels of the test compound were 15.8±8.7 µM (pre-dose), 23.1±603 µM (1 h), and 26.7±7.1 µM (6 h). Compound 1 attained 5/5 cures as determined by the absence of detectable parasitemia in any of the treated mice through 180 days post-infection (FIG. 2). No mice receiving vehicle alone had spontaneous cures. The mice receiving diminazene aceturate (which does not cross the BBB (Bacchi et al., *Antimicrob. Agents Chemother.* 53:3269 (2009))) had temporary clearance of parasitemia, but subsequently relapsed, most likely from parasites leaving the brain and returning to the hemolymphatic system. By observing mice for 180 days, more than ample time is allowed for mice to show signs of illness or parasites to become visible on blood films (as was observed with the diminazene-treated mice), thus providing assurance that the 1-treated mice were cured.

Example 4

Additional Analogs

Additional compounds were synthesized and tested for the efficacy against *T. brucei* and *T. cruzi* as described above. The results are shown in Table 16. The compounds have good potency against both organisms

TABLE 16

| Compound | Chemical Structure | T. b. brucei EC$_{50}$ (nM) | T. Cruzi EC$_{50}$ (nM) |
| --- | --- | --- | --- |
| 41 | 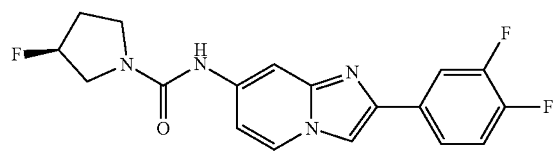 [SMILES: O=C(Nc1ccn2cc(-c3ccc(F)c(F)c3)nc2c1)N1CC[C@H](F)C1] | 160 | 390 |
| 42 | 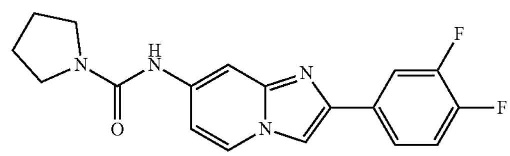 [SMILES: O=C(Nc1ccn2cc(-c3ccc(F)c(F)c3)nc2c1)N1CCCC1] | 320 | 2240 |
| 43 | 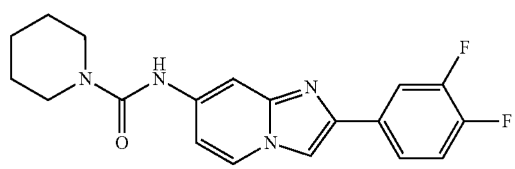 [SMILES: O=C(Nc1ccn2cc(-c3ccc(F)c(F)c3)nc2c1)N1CCCCC1] | 1200 | 2840 |
| 44 | 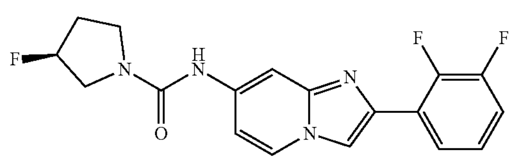 [SMILES: O=C(Nc1ccn2cc(-c3cccc(F)c3F)nc2c1)N1CC[C@H](F)C1] | 180 | 940 |
| 45 | 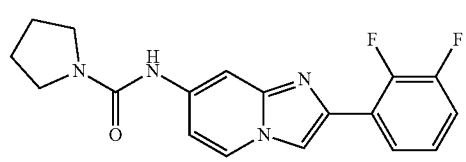 | 580 | 1020 |
| 46 | 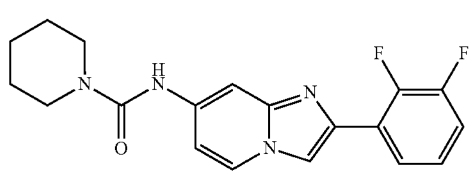 [SMILES: O=C(Nc1ccn2cc(-c3cccc(F)c3F)nc2c1)N1CCCCC1] | 720 | 1000 |

TABLE 16-continued

| Compound | Chemical Structure | T. b. brucei EC$_{50}$ (nM) | T. Cruzi EC$_{50}$ (nM) |
|---|---|---|---|
| 47 | 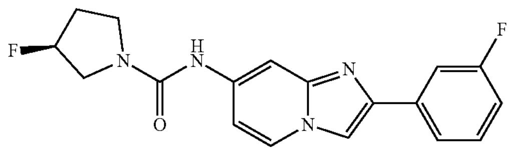 [SMILES: O=C(Nc1ccn2cc(-c3cccc(F)c3)nc2c1)N1CC[C@H](F)C1] | 160 | 710 |
| 48 | 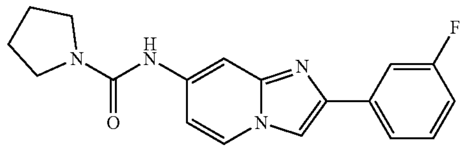 [SMILES: O=C(Nc1ccn2cc(-c3cccc(F)c3)nc2c1)N1CCCC1] | 730 | 2950 |
| 49 | 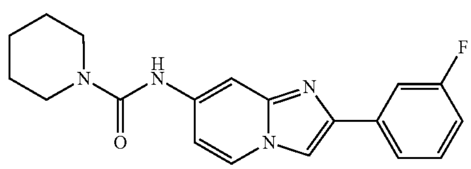 [SMILES: O=C(Nc1ccn2cc(-c3cccc(F)c3)nc2c1)N1CCCCC1] | 970 | 3100 |
| 50 | 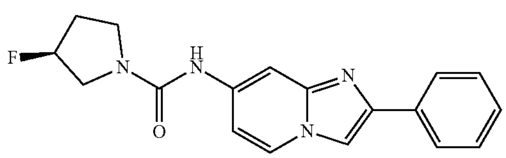 [SMILES: O=C(Nc1ccn2cc(-c3ccccc3)nc2c1)N1CC[C@H](F)C1] | 620 | 1080 |
| 51 | 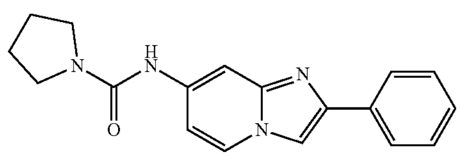 [SMILES: O=C(Nc1ccn2cc(-c3ccccc3)nc2c1)N1CCCC1] | 2230 | 4460 |
| 52 | 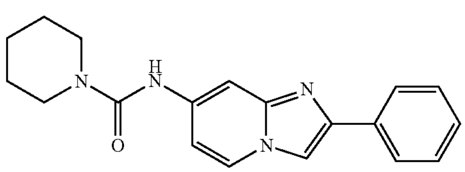 [SMILES: O=C(Nc1ccn2cc(-c3ccccc3)nc2c1)N1CCCCC1] | 2510 | 2750 |
| 53 | 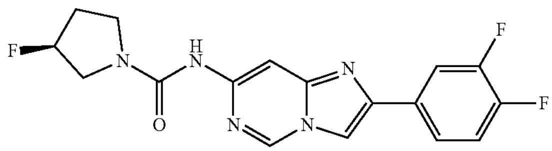 | 20 | 90 |
| 54 | 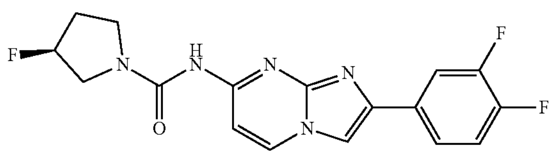 [SMILES: O=C(Nc1ccn2cc(-c3ccc(F)c(F)c3)nc2n1)N1CC[C@H](F)C1] | >20000 | 2530 |

Further compounds were synthesized and tested for the efficacy against *T. brucei* as described above. The results are shown in Table 17.

TABLE 17

| Compound | Chemical Structure | T. b. brucei EC$_{50}$ (nM) | T. b. brucei EC$_{90}$ (nM) |
|---|---|---|---|
| 55 | 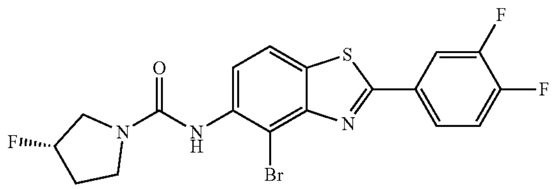 [SMILES: O=C(Nc1ccc2sc(-c3ccc(F)c(F)c3)nc2c1Br)N1CC[C@H](F)C1] | >20,000 | >20,000 |
| 56 | 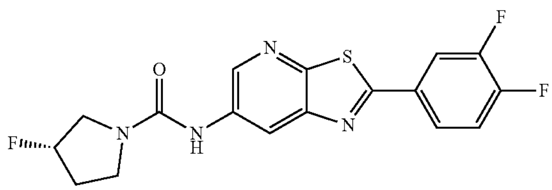 [SMILES: O=C(Nc1cnc2sc(-c3ccc(F)c(F)c3)nc2c1)N1CC[C@H](F)C1] | 181 | 364 |
| 57 | 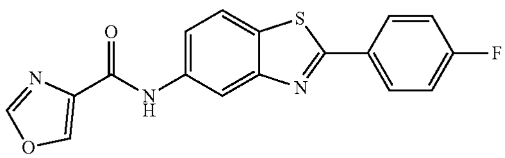 [SMILES: O=C(Nc1ccc2sc(-c3ccc(F)cc3)nc2c1)c1cocn1] | >20,000 | >20,000 |
| 58 | 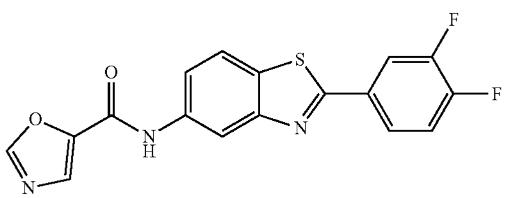 [SMILES: O=C(Nc1ccc2sc(-c3ccc(F)c(F)c3)nc2c1)c1cnco1] | >20,000 | >20,000 |
| 59 | 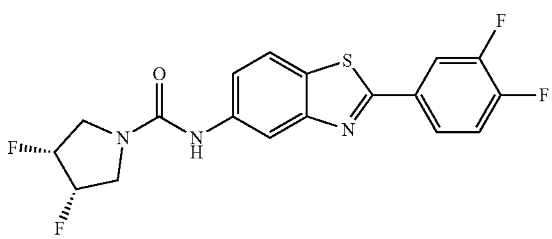 [SMILES: O=C(Nc1ccc2sc(-c3ccc(F)c(F)c3)nc2c1)N1C[C@@H](F)[C@@H](F)C1] | 340 | 517 |
| 60 | 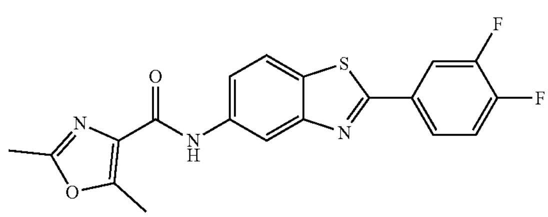 [SMILES: Cc1nc(C(=O)Nc2ccc3sc(-c4ccc(F)c(F)c4)nc3c2)c(C)o1] | >20,000 | >20,000 |
| 61 | 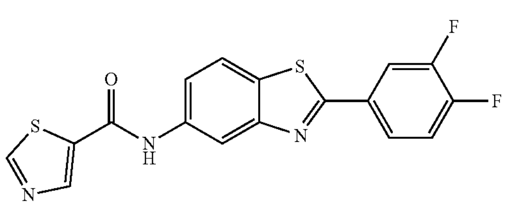 | 3833 | 7372 |

TABLE 17-continued

| Compound | Chemical Structure | T. b. brucei EC$_{50}$ (nM) | T. b. brucei EC$_{90}$ (nM) |
|---|---|---|---|
| 62 | 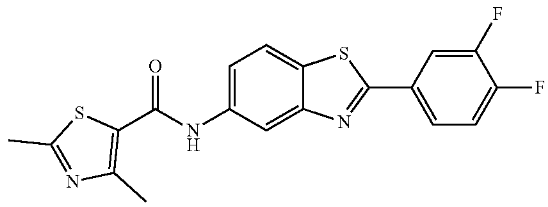 [SMILES: Cc1nc(C)c(C(=O)Nc2ccc3sc(-c4ccc(F)c(F)c4)nc3c2)s1] | >20,000 | >20,000 |
| 63 | 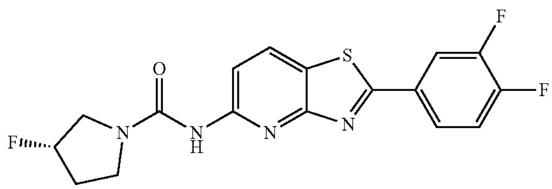 [SMILES: O=C(Nc1ccc2sc(-c3ccc(F)c(F)c3)nc2n1)N1CC[C@H](F)C1] | | |
| 64 | 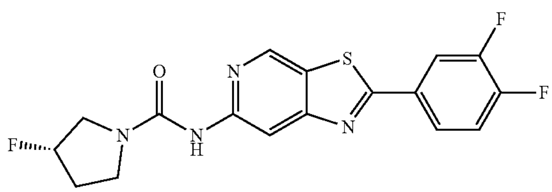 [SMILES: O=C(Nc1cc2nc(-c3ccc(F)c(F)c3)sc2cn1)N1CC[C@H](F)C1] | | |

Example 5

Synthesis of Compounds

General chemistry experimental. Uncorrected melting points were measured on a Thermo Scientific 9200 melting point apparatus. $^1$H NMR spectra were recorded on a Varian Inova 400 MHz, a Bruker AVANCE 400 MHz, or a Varian Inova 600 MHz spectrometer. Anhydrous solvents were purchased from Aldrich Chemical Co., Milwaukee, Wis., or from Fisher Scientific, Waltham, Mass., in Sure-seal® or AcroSeal® containers and were used without further purification. Organic starting materials were purchased from the same sources or were prepared by published procedures as noted. Reaction mixtures were monitored by TLC on silica gel or by reverse phase HPLC. Organic layers of extraction mixtures were neutralized as necessary with acidic or basic washes, washed with saturated NaCl solution and dried over MgSO$_4$ before being evaporated under reduced pressure. Normal phase flash column chromatography was performed using Davisil grade 633, type 60A silica gel (200-425 mesh). Analytical HPLC chromatograms were recorded on an Agilent 1100 or 1200 series chromatograph using a Zorbax Rx C8 column (4.6×75 mm, 3.5 μm) maintained at 40° C. and UV photodiode array detection at 230, 254, 265, 290, and 320 mm Area % values are reported at the wavelengths where the strongest signals of the products were observed. Mobile phases consisted of mixtures of MeOH (0-95%) in water containing formic acid (80 mM), ammonium formate (20 mM) and Et$_3$N (15 mM). Samples were eluted at appropriate gradients at a flow rate of 1.5 mL/min. Low resolution ESI mass spectra were recorded on an Agilent Technologies 1100 Series LC/MSD Trap mass spectrometer or at the North Carolina State University Mass Spectrometry Facility located in the Department of Chemistry. In cases of hydrochloride salts, the m/z values reported are those of the free bases. Elemental analyses were measured by Atlantic Microlab, Norcross, Ga., and unless stated otherwise, were within ±0.4% of calculated values. All target compounds are judged to be >95% pure by elemental analysis and analytical HPLC.

The benzimidazole and benzoxazole compounds of the invention were synthesized as shown in Scheme 1. The reaction of 4-nitrobenzene-1,2-diamine (65) with benzoyl chloride (THF at −10° C.) resulted in the selective formation of amide 66, which underwent ring closure to benzimidazole 67 in the presence of boron trifluoride etherate in refluxing dioxane. Reduction of the nitro group using tin(II) dichloride in refluxing concentrated HCl gave amine 68, which underwent benzoylation in DCM to target compound 14, the HCl salt of the known free base (Kulkarni et al., Med. Chem. 9:91 (2013)). 4-Hydroxybenzene-1,3-diamine dihydrochloride (69) was reacted with benzoic acid in PPA to give 2-phenyl-5-aminobenzoxazole (70). Amine 70 underwent benzoylation to give amide 15 or reaction with triphosgene and triethylamine in DCM followed by addition of the appropriate secondary amine to obtain ureas 8 and 16.

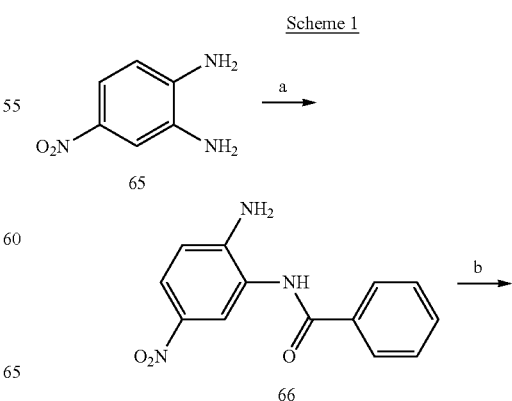

Scheme 1

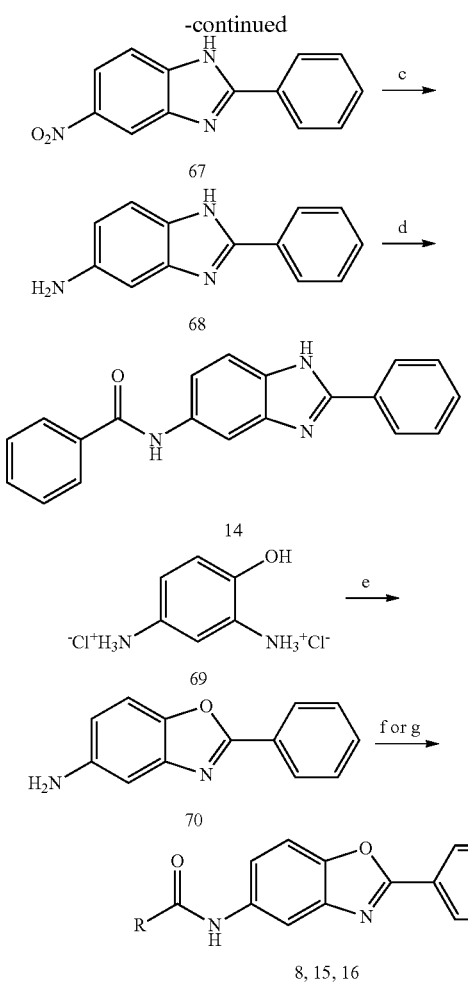

Reagents and conditions: (a) benzoyl chloride, Et₃N, THF, -10° C.;
(b) BF₃•Et₂O, dioxane, reflux, 3 h; (c) SnCl₂•2H₂O, concd HCl,
reflux, 2 h; (d) benzoyl chloride, Et₃N, DCM, rt, overnight;
(e) benzoic acid, PPA, 110-180° C., 4 h; (f) benzoyl chloride, Et₃N,
DCM, rt, overnight; (g) triphosgene, Et₃N, DCM, 0° C. and then
appropriate 2° amine, 0° C. to rt, overnight.

The benzothiazole compounds of the invention were synthesized as shown in Scheme 2. The syntheses of benzothiazoles 1-7, 9-13, and 17-40 began with the acylation of 2-chloro-5-nitroaniline (71a) with the appropriate benzoyl chloride in pyridine to obtain N-phenyl-benzamides 72a-g. Formamide 72h (Chupak et al., US 2006/0135447; Spieler et al., Helv. Chim. Acta 33:1429 (1950)) was prepared from bromoaniline 71b in refluxing formic acid. Amides 72a-h were reacted with sodium sulfide nonahydrate and sulfur in refluxing ethanol (Wynne et al., WO 2007/091106) to give 5-nitrobenzothiazoles 73a-h. These intermediates plus commercially available 63i were reduced to the corresponding amines 74a-i using iron powder and ammonium chloride in refluxing aqueous ethanol (Wynne et al., WO 2007/091106) after the failure to obtain 74a either by catalytic hydrogenation or stannous chloride reduction of 73a. The target benzothiazole amides 17-19, 21, 25, and 28 were prepared from amines 74a-c and the appropriate acyl chloride in the presence of Et₃N in DCM. Thiazole 2-carboxylic acid was treated with 1-[bis(dimethylamino)methylene]-1H-1,2,3-triazolo[4,5-b]-pyridinium 3-oxide hexafluorophosphate) (HATU) in the presence of Et₃N in THF followed by the addition of amine 74a to obtain amide 20. Urea analogues 1-7, 9-13, 22-24, 26, 27, and 29-40 were prepared by reaction the isocyanate derivatives of primary amines 74a-i (generated in situ using triphosgene) with the appropriate secondary amine. Initially (for 7, 23, 24, and 26), the isocyanates were prepared by dropwise addition of a solution of triphosgene (in DCM) to a solution of the primary amine and triethylamine in DCM at −5° C. in order to avoid formation of the undesired symmetric urea. In subsequent reactions, solid triphosgene was added to the reaction mixture in a single portion, producing the same result provided the concentration of the primary amine was below 20 mM. The 3-aminopyrrolidinyl urea 37 was prepared from 3-Boc-aminopyrrolidine and 74g, followed by amine deprotection using TFA. The hydrochloride salt of (3R,4R)-3,4-difluoropyrrolidine (Hulin et al., Bioorg. Med. Chem. Lett. 15:4770 (2005)), the secondary amine precursor to analogue 35, was prepared in five steps from L-tartaric acid by modification of known procedures (Bonanni et al., Synlett 747 (2009); Dieguez et al., J. Chem. Soc., Dalton Trans. 3517 (1998); Kano et al., Tetrahedron 64:1197 (2008); Marson et al., J. Org. Chem. 70:9771 (2005); Miyashita, WO 2010/041402; Rocha Gonsalves et al., J. Mol. Catal. A: Chem. 195:1 (2003)).

Scheme 2

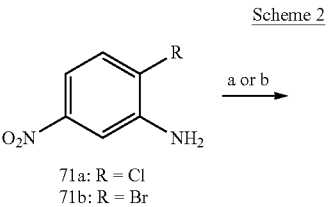

71a: R = Cl
71b: R = Br

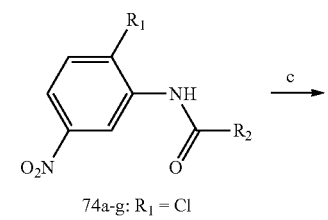

74a-g: R₁ = Cl
72h: R₁ = Br

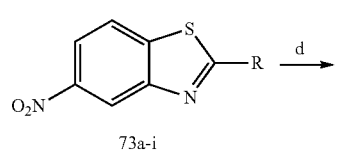

73a-i a: R (R₂) = Ph
b: R (R₂) = 4-fluorophenyl
c: R (R₂) = 3-fluorophenyl
d: R (R₂) = 2-fluorophenyl
e: R (R₂) = 2,3-difluorophenyl
f: R (R₂) = 2,4-difluorophenyl
g: R (R₂) = 3,4-difluorophenyl
h: R (R₂) = H
j: R (R₂) = Me

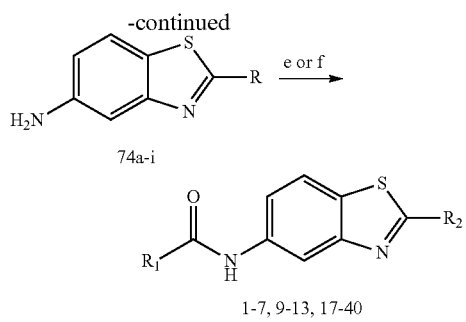

1-7, 9-13, 17-40

Reagents and conditions: (a) appropriate benzoyl chloride, Py, rt, overnight; (b) HCO₂H, reflux (for 99 h); (c) Na₂S•9H₂O, S₈, EtOH, reflux; (d) Fe, NH₄Cl, aq EtOH, reflux; (e) appropriate acyl halide or active ester, Et₃N, DCM, rt, overnight (for amides); (f) triphosgene, Et₃N, DCM, -5° C. and then appropriate 2° amine, 0° C. to rt, overnight (for ureas).

The synthesis of compounds 55 and 59 is shown in Scheme 3. Urea 59 (Scheme 3) was prepared analogously to 1 from 74g and cis-3,4-difluoropyrroldine HCl. Similar methodology was employed for the preparation of urea 55 from 75 (the bromination product of 74g) and (S)-3-fluoro-pyrroldine HCl.

The oxazoyl and thiazoyl amide compounds of the invention were synthesized as shown in Scheme 4. Amide 57 was prepared from 74g and oxazole-4-carboxylic acid using oxalyl chloride, a catalytic amount of DMF, and triethylamine in dichloromethane (Scheme 4). The other four amides were prepared from 74g and the appropriate carboxylic acid in the presence of 1-[bis(dimethylamino)methylene]-1H-1,2,3-triazolo[4,5-b]pyridinium 3-oxide hexafluorophosphate (HATU) and diisopropylethylamine in DMF.

Scheme 4

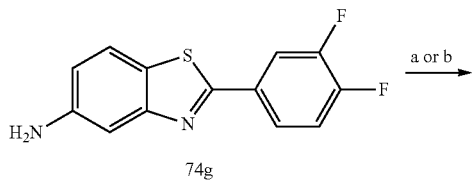

Scheme 3

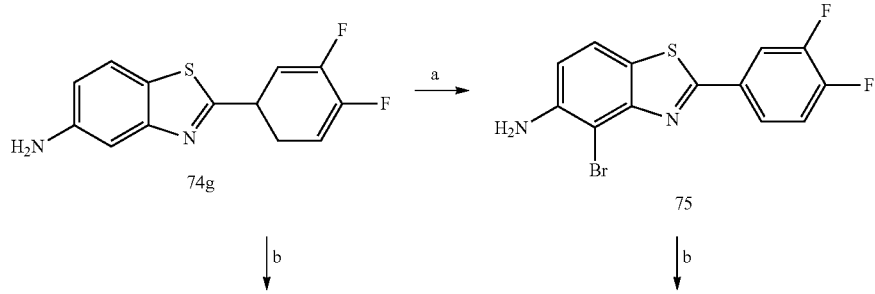

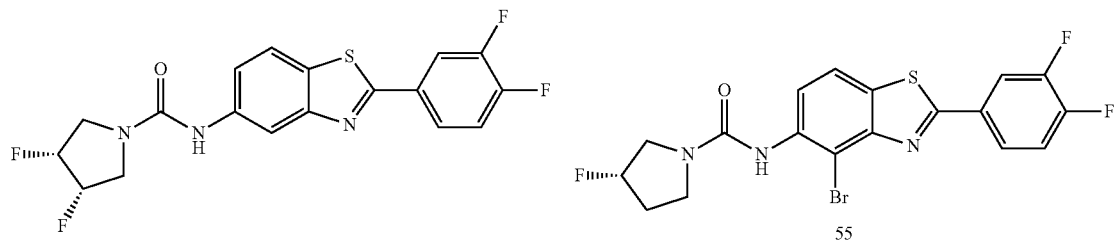

Reagents and conditions: (a) N-bromosuccinimide, CH₃CN, rt; (b) triphosgene, Et₃N, DCM, 5° C. and then appropriate 2° amine HCl salt, 0° to rt, overnight.

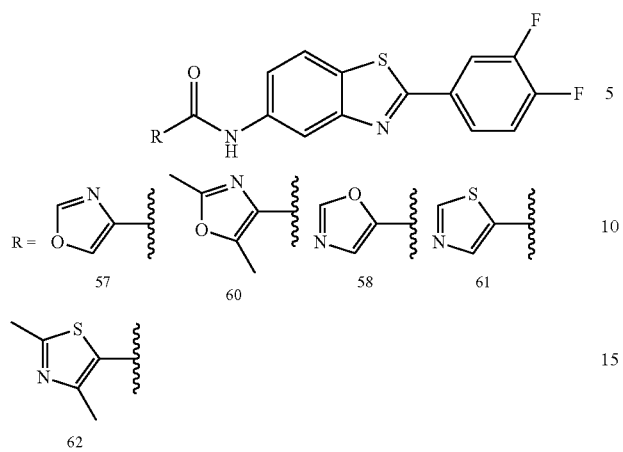

Reagents and conditions: (a) oxazole-4-carboxylic acid, oxalyl chloride, DMF, Et₃N, DCM; (b) appropriate carboxylic acid, HATU, DIEA, DMF.

The synthesis of the 7-aza analogue of 1 is depicted in Scheme 5. This pathway began with the reaction of 2-chloro-5-nitronicotinic acid with diphenylphosphoryl azide (DPPA) in the presence of tert-butanol in triethylamine in refluxing toluene to give 3-Boc-amino-2-chloro-5-nitropyridine (76). The carbamate underwent deprotection (trifluoroacetic acid/dichloromethane) followed by reaction of the crude amine with 3,4-difluorbenzoyl chloride to give amide 77. The amide underwent cyclization using Lawesson's reagent (1,3-dimethyl-3,4,5,6-tetrahydro-2(1H)-pyrimidinone (DMPU), 160° C. for 15 minutes) to give the 7-azabenzothiazole 78. Reduction of the nitro group (Fe, NH₄Cl, EtOH/H₂O, reflux) gave the amine 79, which was reacted analogously to 74g with (S)-3-fluoropyrrolidine HCl to give 56.

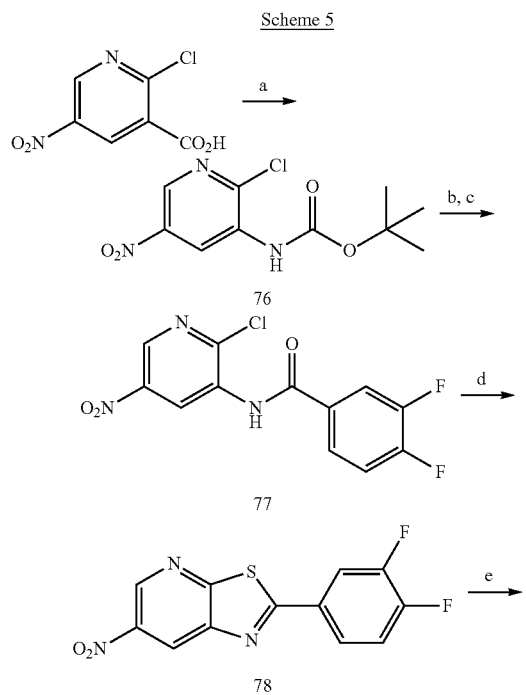

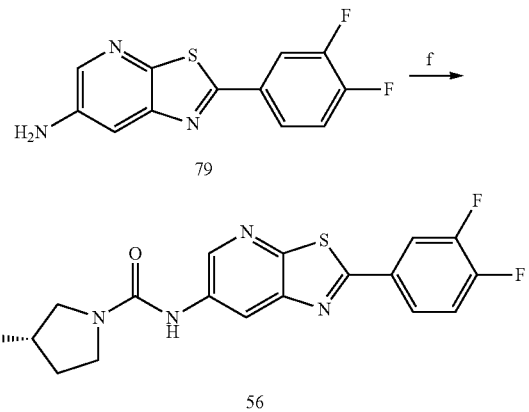

Reagents and conditions: (a) DPPA, t-BuOH, Et₃N, toluene, reflux 2 h; (b) TFA/DCM (1:1), rt; (c) 3,4-difluorobenzoyl chloride, Py; (d) Lawesson's reagent, DMPU, 160° C., 15 min; (e) Fe, NH₄Cl, EtOH/H₂O (2:1), reflux 3 h; (f) triphosgene, Et₃N, DCM, 5° C. and then appropriate (S)-3-fluoropyrrolidine HCl, 0° to rt, overnight.

The proposed synthesis of 4-aza analogue of 1 is shown in Scheme 6.

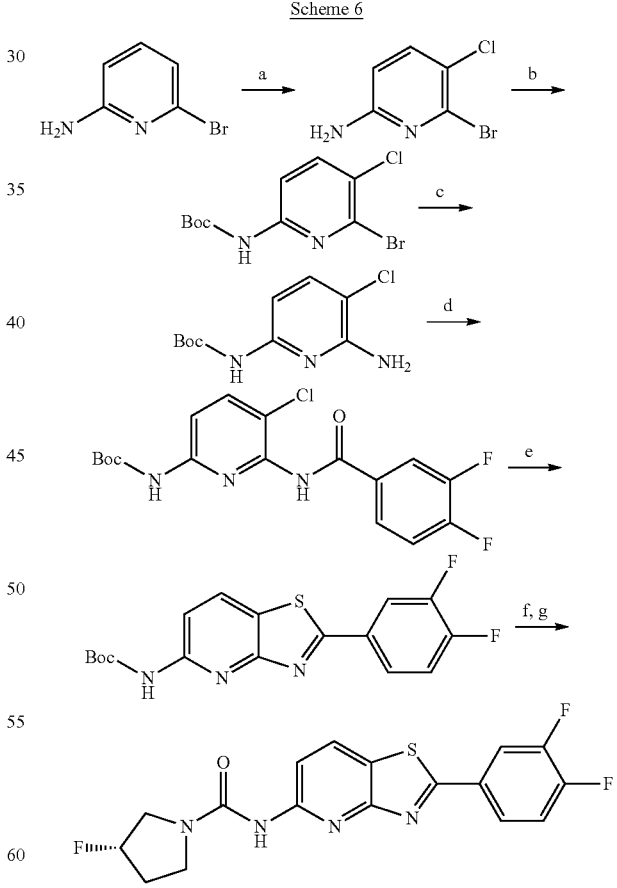

Reagents and conditions: (a) N-chlorosuccinimide, CH₃CN, reflux; (b) di-tert-butyl dicarbonate, NaN[Si(CH₃)₃], THF; (c) NH₃ gas, Cu₂O, ethylene glycol, pressure tube, rt; (d) 3,4-diflurobenzoyl chloride, Py; (e) Lawesson's reagent, DMPU; (f) TFA, DCM; (g) triphosgene, Et₃N, DCM, 0° C. and then (S)-3-fluorpyrrolidine HCl, rt.

The proposed synthesis of 6-aza analogue of 1 is shown in Scheme 7.

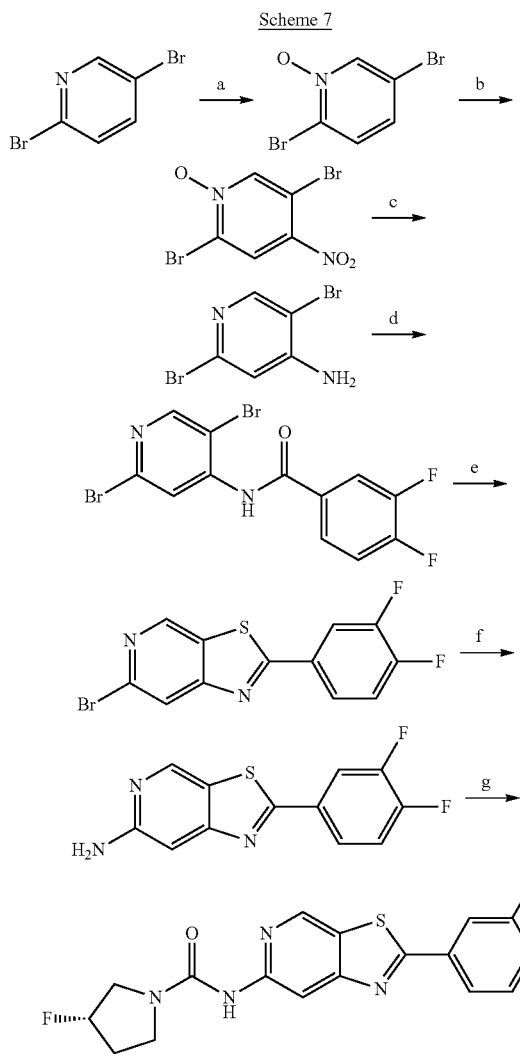

Reagents and conditions: (a) H₂O₂, TFA, 70-90° C.; (b) 90% HNO₃, H₂SO₄, 100° C., (c) Fe, NH₄Cl, aq. EtOH, reflux; (d) 3,4-diflurobenzoyl chloride, Py; (e) Lawesson's reagent, DMPU; (f) NH₃ gas, Cu₂O, ethylene glycol, pressure tube, rt; (g) triphosgene, Et3N, DCM, 0° C. and then (S)-3-fluorpyrrolidine HCl, rt.

The synthesis of compounds 41-54 is depicted in Scheme 8.

Scheme 8

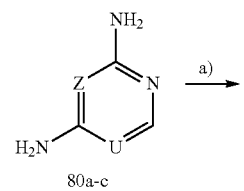

80a; W and V = CH
80b; W = N, V = CH
80c; W = CH, V = N

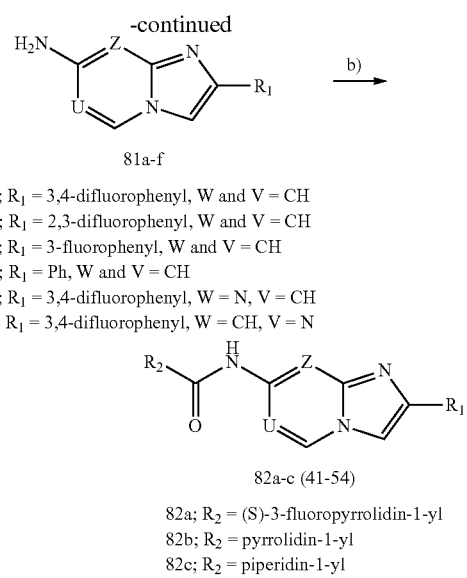

81a-f

81a; R₁ = 3,4-difluorophenyl, W and V = CH
81b; R₁ = 2,3-difluorophenyl, W and V = CH
81c; R₁ = 3-fluorophenyl, W and V = CH
81d; R₁ = Ph, W and V = CH
81e; R₁ = 3,4-difluorophenyl, W = N, V = CH
81f; R₁ = 3,4-difluorophenyl, W = CH, V = N 82a-c (41-54)

82a; R₂ = (S)-3-fluoropyrrolidin-1-yl
82b; R₂ = pyrrolidin-1-yl
82c; R₂ = piperidin-1-yl Reagents and conditions: a) appropriate diaminopyridine/pyrimidine and bromoacetophenone, NaHCO₃, MeOH. reflux, 12 h and b) triphosgene, Et₃N, DCM, 0° C. and then appropriate 2° amine, 0° C. to r.t., overnight.

5-Benzamido-2-phenylbenzimidazole hydrochloride (14)

Benzoyl chloride (80 µL, 0.690 mmol) was added to a mixture of 5-amino-2-phenylbenzimidazole (Shi et al., *Bioorg. Med. Chem.* 22:4735 (2014)) (68, 113 mg, 0.538 mmol) and Et₃N (150 µL, 1.08 mmol) in DCM (20 mL), and the mixture was stirred overnight before being diluted with water and extracted into DCM. The product was recrystallized from EtOH/H₂O (treated with Norit) as a pink powder, which was then recrystallized from EtOH/1 M HCl as a white solid (76.4 mg, 41%): mp>290° C.; ¹H NMR (400 MHz, DMSO-d₆) δ 15.40 (s, 2H), 10.65 (s, 1H), 8.52 (d, J=1.8 Hz, 1H), 8.33 (dd, J=6.8, 2.9 Hz, 2H), 8.02 (d, J=7.4 Hz, 2H), 7.90 (dd, J=8.9, 1.9 Hz, 1H), 7.83 (d, J=8.8 Hz, 1H), 7.77-7.68 (m, 3H), 7.63 (t, J=7.2 Hz, 1H), 7.57 (t, J=7.4 Hz, 2H); EIMS m/z 314.1 (M+1)⁺; HPLC 99.0 area % (320 nm). Anal. Calcd for C₂₀H₁₅N₃O.HCl.1.4H₂O: C, 64.05; H, 5.05; N, 11.20. Found: C, 63.93; H, 4.98; N, 11.02.

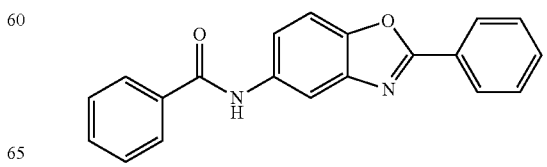

5-Benzamido-2-phenylbenzoxazole (Burri, *Parasitology* 137:1987 (2010)) (15) was prepared analogously to 14 from benzoyl chloride (250 μL, 2.16 mmol), 5-amino-2-phenylbenzoxazole (75, 316 mg, 1.50 mmol), and Et$_3$N (500 μL, 3.59 mmol) in DCM (10 mL). The product was recrystallized from EtOH/water and then from MeOH as light pink crystals (317 mg, 67%): mp 182-184° C.; $^1$H NMR (400 MHz, DMSO-d$_6$) δ 10.44 (s, 1H), 8.30 (t, J=1.3 Hz, 1H), 8.28-8.16 (m, 2H), 8.04-7.96 (m, 2H), 7.78 (d, J=1.3 Hz, 2H), 7.69-7.59 (m, 4H), 7.56 (ddt, J=8.5, 6.5, 1.7 Hz, 2H); EIMS m/z 315.0 (M+1)$^+$; HPLC 100 area % (265 nm). Anal. Calcd for C$_{20}$H$_{14}$N$_2$O$_2$: C, 76.42; H, 4.49; N, 8.91. Found: C, 76.21; H, 4.63; N, 8.75.

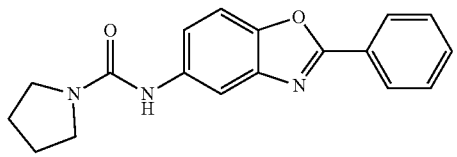 [SMILES: O=C(Nc1ccc2oc(-c3ccccc3)nc2c1)N1CCCC1]

2-Phenyl-5-N-pyrrolidylamidobenzoxazole (8)

A solution of triphosgene (155 mg, 0.523 mmol) in DCM (30 mL) was added dropwise to a solution of 5-amino-2-phenylbenzoxazole (70, 317 mg, 1.51 mmol) and Et$_3$N (0.5 mL, 3.59 mmol) in DCM (50 mL) at −10° C. After 1 h, pyrrolidine (0.27 g, 3.80 mmol) was added, and the ice-salt bath was removed. The mixture was stirred for 2 h at room temperature and was then diluted with water and extracted into DCM. The product was recrystallized from DCM/hexanes as an off-white powder (331 mg, 71%): mp 221-222.5° C.; $^1$H NMR (400 MHz, DMSO-d$_6$) δ 8.26 (s, 1H), 8.23-8.14 (m, 2H), 7.99 (d, J=2.1 Hz, 1H), 7.68-7.55 (m, 4H), 7.52 (dd, J=8.8, 2.1 Hz, 1H), 3.44-3.36 (m, 4H), 1.93-1.81 (m, 4H); EIMS m/z 308.3 (M+1)$^+$; HPLC 100 area % 265 nm). Anal. Calcd for C$_{18}$H$_{17}$N$_3$O$_2$.0.2H$_2$O: C, 69.53; H, 5.64; N, 13.51. Found: C, 69.45; H, 5.68; N, 13.29.

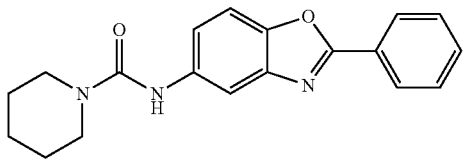

2-Phenyl-5-N-piperidylamidobenzoxazole (16) was prepared analogously to 8 from 70 (319 mg, 1.52 mmol) and piperidine (0.25 g, 2.94 mmol) as light yellow crystals (237 mg, 49%): mp 207-209° C.; $^1$H NMR (400 MHz, DMSO-d$_6$) δ 8.58 (s, 1H), 8.23-8.14 (m, 2H), 7.93 (d, J=2.1 Hz, 1H), 7.67-7.56 (m, 4H), 7.47 (dd, J=8.8, 2.1 Hz, 1H), 3.49-3.41 (m, 4H), 1.65-1.56 (m, 2H), 1.56-1.46 (m, 4H); EIMS m/z 322.2 (M+1)$^+$; HPLC 100 area % (254 nm). Anal. Calcd for C$_{19}$H$_{19}$N$_3$O$_2$: C, 71.01; H, 5.96; N, 13.08. Found: C, 70.96; H, 6.06; N, 12.92.

5-Aminobenzothiazole Amide Derivatives 17-21, 25, and 28

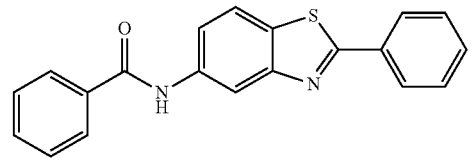 [SMILES: O=C(Nc1ccc2sc(-c3ccccc3)nc2c1)c1ccccc1]

5-Benzamido-2-phenylbenzothiazole (17)

Et$_3$N (0.5 mL, 3.59 mmol) was added to a solution of 5-amino-2-phenylbenzothiazole (74a, 340.3 mg, 1.50 mmol) and benzoyl chloride (250 μL, 2.16 mmol) in DCM. The mixture was stirred at rt overnight before being diluted with water and extracted into DCM. Recrystallization of the product from EtOH gave white crystals (406 mg, 82%): mp 221-222° C.; $^1$H NMR (400 MHz, DMSO-d$_6$) δ 10.50 (s, 1H), 8.62 (d, J=2.0 Hz, 1H), 8.18-8.07 (m, 3H), 8.06-7.97 (m, 2H), 7.85 (dd, J=8.7, 2.0 Hz, 1H), 7.68-7.52 (m, 6H); EIMS m/z 331.0 (M+1)$^+$; HPLC 99.2 area % (290 nm). Anal. Calcd for C$_{20}$H$_{14}$N$_2$OS: C, 72.69; H, 4.27; N, 8.48. Found: C, 72.45; H, 4.50; N, 8.42.

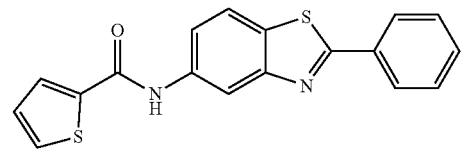 [SMILES: O=C(Nc1ccc2sc(-c3ccccc3)nc2c1)c1cccs1]

2-Phenyl-5-(2-thienylamido)benzothiazole (18) was prepared analogously to 17 from 5-amino-2-phenylbenzothiazole (74a, 340.3 mg, 1.50 mmol) and 2-thiophenecarbonyl chloride (75 μL, 0.704 mmol) as white crystals (157 g, 83%): mp 256° C.; $^1$H NMR (600 MHz, DMSO-d$_6$) δ 10.48 (s, 1H), 8.55 (d, J=2.0 Hz, 1H), 8.14-8.09 (m, 3H), 8.09 (dd, J=3.8, 1.1 Hz, 1H), 7.91 (dd, J=5.0, 1.1 Hz, 1H), 7.78 (dd, J=8.7, 2.0 Hz, 1H), 7.62-7.56 (m, 3H), 7.27 (dd, J=5.0, 3.7 Hz, 1H). EIMS m/z 337.0 (M+1)$^+$; HPLC 100 area % (290 nm). Anal. Calcd for C$_{18}$H$_{12}$N$_2$O$s_2$: C, 64.26; H, 3.60; N, 8.33. Found: C, 63.97; H, 3.71; N, 8.18.

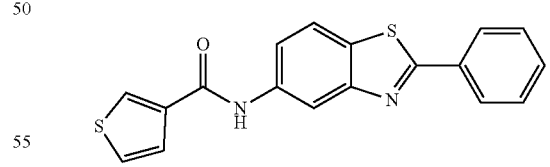

2-Phenyl-5-(3-thienylamido)benzothiazole (19) was prepared analogously to 17 from 5-amino-2-phenylbenzothiazole (74a, 127.0 mg, 0.561 mmol) and 3-thiophenecarbonyl chloride (prepared from the corresponding acid (251 mg, 1.96 mmol) and thionyl chloride (1.0 mL, 1.27 mmol) in refluxing toluene) as white crystals (110 mg, 58%); 200-201° C.; $^1$H NMR (400 MHz, DMSO-d$_6$) δ 10.30 (d, J=8.9 Hz, 1H), 8.58 (d, J=2.0 Hz, 1H), 8.40 (dd, J=2.6, 1.7 Hz, 1H), 8.15-8.06 (m, 3H), 7.79 (dd, J=8.7, 2.1 Hz, 1H), 7.73-7.64 (m, 2H), 7.63-7.53 (m, 3H); EIMS m/z 337.0

(M+1)+; HPLC 100 area % (290 nm). Anal. Calcd for C$_{18}$H$_{12}$N$_2$OS$_2$.0.1H$_2$O: C, 63.92; H, 3.64; N, 8.283. Found: C, 63.86; H, 3.73; N, 8.25.

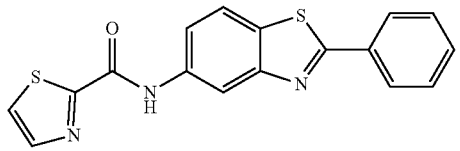 [SMILES: O=C(Nc1ccc2sc(-c3ccccc3)nc2c1)c1nccs1]

N-(2-Phenylbenzo[d]thiazol-5-yl)thiazole-2-carboxamide (20)

A solution of thiazole-2-carboxylic acid (102 mg, 0.786 mmol), Et$_3$N (0.3 mL, 2.15 mmol) and HATU (299 mg, 0.787 mmol) in THF (10 mL) was stirred for 1.5 h at room temperature before the addition of 5-amino-2-phenylbenzothiazole (74a, 142 mg, 0.628 mmol). The mixture was stirred overnight before being diluted with saturated NaCl and extracted into EtOAc. The product was recrystallized form EtOH as an off-white solid (116 mg (55%): mp 161-162; $^1$H NMR (400 MHz, DMSO-d$_6$) δ 11.08 (s, 1H), 8.64 (d, J=2.0 Hz, 1H), 8.18 (d, J=3.1 Hz, 1H), 8.15 (d, J=3.0 Hz, 1H), 8.14-8.07 (m, 3H), 7.97 (dd, J=8.8, 2.1 Hz, 1H), 7.63-7.55 (m, 3H); EIMS m/z 337.9 (M+1)+; HPLC 100 area % (290 nm). Anal. Calcd for C$_{17}$H$_{11}$N$_3$OS$_2$.0.2H$_2$O: C, 59.87; H, 3.37; N, 12.32. Found: C, 59.74; H, 3.42; N, 12.19.

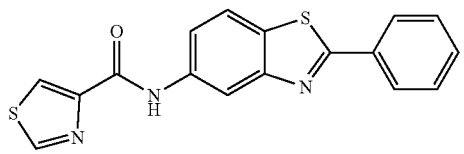 [SMILES: O=C(Nc1ccc2sc(-c3ccccc3)nc2c1)c1cscn1]

N-(2-Phenylbenzo[d]thiazol-5-yl)thiazole-4-carboxamide (21) was prepared from 5-amino-2-phenylbenzothiazole (74a, 127 mg, 0.559 mmol) and thiazolecarboxylic acid (131 mg, 1.01 mmol) analogously to 19 above except that neat thionyl chloride was used to prepare the acyl chloride. The product was isolated as a white solid (142 mg, 76%): mp 180-181° C.; $^1$H NMR (400 MHz, DMSO-d$_6$) δ 10.65 (s, 1H), 9.31 (d, J=2.0 Hz, 1H), 8.68 (d, J=1.9 Hz, 1H), 8.58 (d, J=2.0 Hz, 1H), 8.16-8.07 (m, 3H), 7.96 (dd, J=8.7, 2.1 Hz, 1H), 7.64-7.53 (m, 3H); EIMS m/z 338.0 (M+1)+; HPLC 100 area % (290 nm). Anal. Calcd for C$_{17}$H$_{11}$N$_3$OS$_2$.0.1H$_2$O: C, 60.19; H, 3.33; N, 12.39. Found: C, 60.18; H, 3.41; N, 12.29.

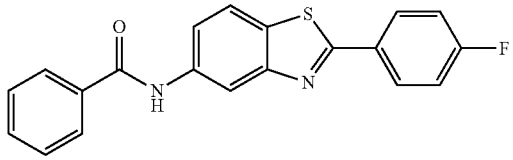 [SMILES: O=C(Nc1ccc2sc(-c3ccc(F)cc3)nc2c1)c1ccccc1]

5-Benzamido-2-(4-fluorophenyl)benzothiazole (25) was prepared analogously to 33 from 5-amino-2-(4-fluorophenyl)benzothiazole (74b, 127 mg, 0.521 mmol) and benzoyl chloride (80 μL, 0.690 mmol) as white crystals (138 mg, 76%): mp 232.5-233.5° C.; $^1$H NMR (400 MHz, DMSO-d$_6$) δ 10.51 (s, 1H), 8.61 (d, J=2.0 Hz, 1H), 8.21-8.14 (m, 2H), 8.11 (d, J=8.7 Hz, 1H), 8.05-7.97 (m, 2H), 7.84 (dd, J=8.7, 2.1 Hz, 1H), 7.68-7.60 (m, 1H), 7.60-7.52 (m, 2H), 7.49-7.38 (m, 2H); EIMS m/z 349.1 (M+1)+; HPLC 100 area % (290 nm). Anal. Calcd for C$_{20}$H$_{13}$FN$_3$OS$_2$.0.4H$_2$O: C, 67.55; H, 3.91; N, 7.88. Found: C, 67.57; H, 3.92; N, 7.92.

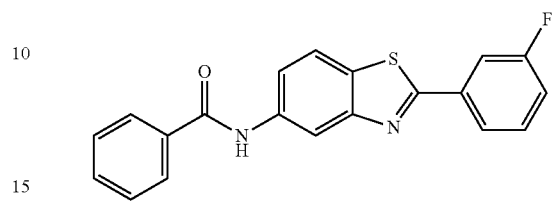

5-Benzamido-2-(3-fluorophenyl)benzothiazole (28) was prepared analogously to 33 from 5-amino-2-(3-fluorophenyl)benzothiazole (74c, 128 mg, 0.523 mmol) and benzoyl chloride (0.15 g, 1.29 mmol) as white crystals (148 mg, 81%): mp 221-22° C.; $^1$H NMR (400 MHz, DMSO-d$_6$) δ 10.53 (s, 1H), 8.64 (d, J=2.0 Hz, 1H), 8.13 (d, J=8.7 Hz, 1H), 8.04-7.98 (m, 2H), 7.97-7.89 (m, 2H), 7.87 (dd, J=8.7, 2.0 Hz, 1H), 7.69-7.60 (m, 2H), 7.57 (t, J=7.4 Hz, 2H), 7.45 (td, J=8.6, 2.6 Hz, 1H); EIMS m/z 349.0 (M+1)+; HPLC 100 area % (290 nm). Anal. Calcd for C$_{20}$H$_{13}$FN$_3$OS$_2$.0.75H$_2$O: C, 66.37; H, 4.04; N, 7.74. Found: C, 66.10; H, 3.77; N, 7.69.

General Procedure for 5-Aminobenzothiazole Urea Derivatives 1-7, 9-13, 22-24, 26, 27, and 29-40

A stirred solution of the appropriate primary amine (0.5-2 mmol) and Et$_3$N (min of 2 equivalents) in DCM was chilled to maximum internal temperature of −5° C. (ice-salt bath). Triphosgene (0.35-0.55 equivalent) was added either dropwise as a solution in DCM (for 7, 23, 24, and 26) or all at once in solid form for all others. The method of introduction was noncritical provided the final concentration of the primary amine was below 20 mM. The mixture was maintained at −5° C. until the starting material was no longer detectable by HPLC (typically 1 h or less). The secondary amine (min of 1 equivalent) or its HCl salt (in which cases an additional equivalent of Et$_3$N was employed) was added, and the solution was allowed to warm to room temperature overnight. The reaction mixture was diluted with water and extracted into DCM. Unless stated otherwise, the product was directly recrystallized from the appropriate solvent(s).

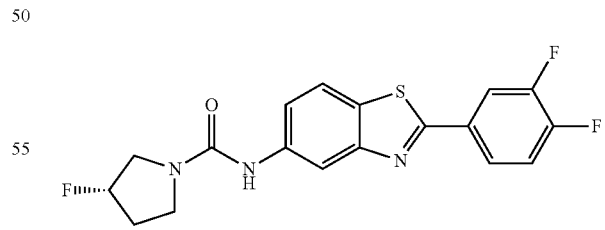

(S)-2-(3,4-Difluorophenyl)-5-(3-fluoro-N-pyrrolidylamido)benzothiazole (1) was prepared from 5-amino-2-(3,4-difluorophenyl)benzothiazole (74g, 0.63 mmol) and (S)-3-fluorpyrrolidine hydrochloride. The product was purified on a silica gel column eluting with hexanes/EtOAc (1:2) and recrystallized from EtOAc/hexanes as white crystals (86 mg, 36%); mp 208-209° C.; $^1$H NMR (400 MHz, DMSO-d$_6$) δ 8.50 (s, 1H), 8.33 (d, J=2.0 Hz, 1H), 8.13 (ddd, J=11.3, 7.7, 2.2 Hz, 1H), 7.99 (d, J=8.8 Hz, 1H), 7.96-7.89 (m, 1H), 7.69-7.58 (m, 2H), 5.39 (dm, J=53.3 Hz, 1H), 3.80-3.52 (m, 3H), 3.47 (td, J=10.3, 6.9 Hz, 1H), 2.27-2.00 (m, 2H); EIMS m/z 378.0 (M+1)$^+$; HPLC 97.0 area % (254 nm). Anal. Calcd for $C_{18}H_{14}F_3N_3OS \cdot 0.3H_2O$: C, 56.48; H, 3.84; N, 10.98. Found: C, 56.21; H, 3.77; N, 10.89.

A scale-up synthesis from a total of 6.6 mmol of 74g was performed in three batches. The combined product was chromatographed as above and recrystallized from EtOH as white crystals (1.59 g, 64%): mp 210-211.55° C.; HPLC 97.8% (254 nm). Anal. Calcd for $C_{18}H_{14}F_3N_3OS$: C, 57.29; H, 3.74; N, 11.13. Found: C, 57.32; H, 3.81; N, 11.02.

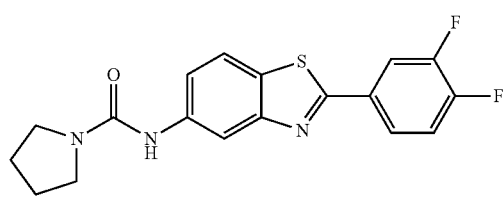 [SMILES: O=C(Nc1ccc2sc(-c3ccc(F)c(F)c3)nc2c1)N1CCCC1]

2-(3,4-Difluorophenyl)-5-(N-pyrrolidylamido)benzothiazole (2) was prepared from 5-amino-2-(3,4-difluorophenyl)benzothiazole (74g) and pyrrolidine. The product was recrystallized from EtOH as white crystals (147 mg, 58%); mp 221-223° C.; $^1$H NMR (400 MHz, DMSO-d$_6$) δ 8.35 (s, 1H), 8.34 (d, J=2.1 Hz, 1H), 8.12 (ddd, J=11.2, 7.7, 2.2 Hz, 1H), 7.97 (d, J=8.7 Hz, 1H), 7.95-7.89 (m, 1H), 7.69-7.58 (m, 2H), 3.46-3.37 (m, 4H), 1.95-1.82 (m, 4H); EIMS m/z 360.1 (M+1)$^+$; HPLC 98.7 area % (254 nm). Anal. Calcd for $C_{18}H_{15}F_2N_3OS$: C, 60.16; H, 4.21; N, 11.69. Found: C, 59.87; H, 4.26; N, 11.59.

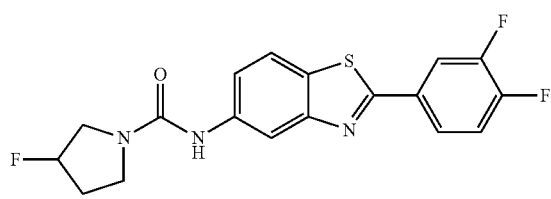 [SMILES: O=C(Nc1ccc2sc(-c3ccc(F)c(F)c3)nc2c1)N1CCC(F)C1]

2-(3,4-Difluorophenyl)-5-(3-fluoro-N-pyrrolidylamido)benzothiazole (3) was prepared from 5-amino-2-(3,4-difluorophenyl)benzothiazole (74g) and 3-fluorpyrrolidine hydrochloride. The product was recrystallized from DCM/hexanes as white crystals (146 mg, 64%); mp 209-210° C.; $^1$H NMR (400 MHz, DMSO-d$_6$) δ 8.50 (s, 1H), 8.33 (d, J=2.1 Hz, 1H), 8.13 (ddd, J=11.4, 7.7, 2.2 Hz, 1H), 7.99 (d, J=8.8 Hz, 1H), 7.93 (dt, J=7.5, 1.9 Hz, 1H), 7.69-7.58 (m, 2H), 5.39 (dm, J=52.9 Hz, 1H), 3.81-3.42 (m, 4H), 2.29-2.00 (m, 2H); EIMS m/z 378.0 (M+1)$^+$; HPLC 97.1 area % (254 nm). Anal. Calcd for $C_{18}H_{14}F_3N_3OS$: C, 57.29; H, 3.74; N, 11.13. Found: C, 57.23; H, 3.83; N, 11.23.

(R)-2-(3,4-Difluorophenyl)-5-(3-fluoro-N-pyrrolidylamido)benzothiazole (4) was prepared from 5-amino-2-(3,4-difluorophenyl)benzothiazole (74g) and (R)-3-fluorpyrrolidine hydrochloride. The product was purified on a silica gel column eluting with hexanes/EtOAc (1:2) and recrystallized from EtOAc/hexanes as white crystals (93 mg, 39%); mp 208-209° C.; $^1$H NMR (400 MHz, DMSO-d$_6$) δ 8.50 (s, 1H), 8.33 (dd, J=2.1, 0.5 Hz, 1H), 8.13 (ddd, J=11.3, 7.7, 2.2 Hz, 1H), 7.99 (dd, J=8.8, 0.5 Hz, 1H), 7.93 (dddd, J=8.7, 3.9, 2.2, 1.3 Hz, 1H), 7.69-7.58 (m, 2H), 5.39 (dm, J=53.4 Hz, 1H), 3.81-3.52 (m, 3H), 3.46 (dd, J=10.2, 7.0 Hz, 1H), 2.28-2.04 (m, 2H); EIMS m/z 378.0 (M+1)$^+$; HPLC 100 area % (254 nm). Anal. Calcd for $C_{18}H_{14}F_3N_3OS \cdot 0.1H_2O$: C, 57.01; H, 3.77; N, 11.08. Found: C, 56.78; H, 3.75; N, 11.03.

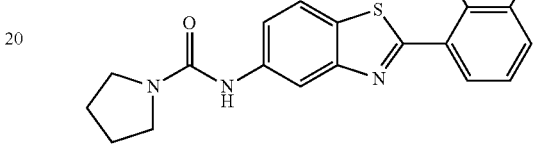

2-(2,3-Difluorophenyl)-5-(N-pyrrolidylamido)benzothiazole (5) was prepared from 5-amino-2-(2,3-difluorophenyl)benzothiazole (74e) and pyrrolidine. The product was recrystallized from EtOH as white crystals (124 mg, 61%); mp 194-195° C.; $^1$H NMR (400 MHz, DMSO-d$_6$) δ 8.41 (dd, J=2.1, 0.5 Hz, 1H), 8.38 (s, 1H), 8.14 (ddt, J=8.0, 6.3, 1.6 Hz, 1H), 8.02 (dd, J=8.8, 0.5 Hz, 1H), 7.72-7.60 (m, 2H), 7.43 (tdd, J=8.2, 5.1, 1.6 Hz, 1H), 3.46-3.38 (m, 4H), 1.94-1.83 (m, 4H); EIMS m/z 360.1 (M+1)$^+$; HPLC 99.6 area % (254 nm). Anal. Calcd for $C_{18}H_{15}F_2N_3OS$: C, 60.16; H, 4.21; N, 11.69. Found: C, 60.17; H, 4.21; N, 11.75.

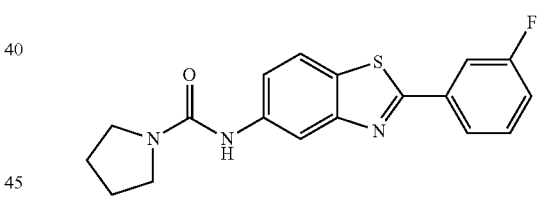

2-(3-Fluorophenyl)-5-(N-pyrrolidylamido)benzothiazole (6) was prepared from 5-amino-2-(3-fluorophenyl)benzothiazole (74c) and pyrrolidine. The product was recrystallized from EtOH as yellow crystals (120 mg, 67%); mp 232-233° C.; $^1$H NMR (400 MHz, DMSO-d$_6$) δ 8.36 (s, 1H), 8.35 (d, J=2.0 Hz, 1H), 7.98 (d, J=8.8 Hz, 1H), 7.95-7.84 (m, 2H), 7.68-7.57 (m, 2H), 7.43 (tdd, J=8.4, 2.6, 1.0 Hz, 1H), 3.45-3.38 (m, 4H), 1.94-1.84 (m, 4H); EIMS m/z 342.1 (M+1)$^+$; HPLC 97.9 area % (254 nm). Anal. Calcd for $C_{18}H_{16}FN_3OS$: C, 63.33; H, 4.72; N, 12.31. Found: C, 63.38; H, 4.90; N, 12.26.

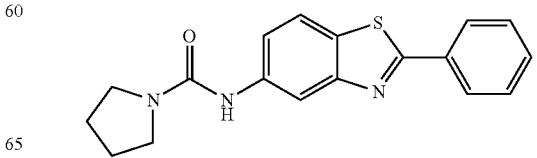

2-Phenyl-5-(N-pyrrolidylamido)benzothiazole (7) was prepared from 5-amino-2-phenylbenzothiazole (74a) and pyrrolidine. The product was recrystallized from EtOH as a beige solid (219 mg, 58%); mp 210-211° C.; $^1$H NMR (400 MHz, DMSO-d$_6$) δ 8.33 (s, 1H), 8.32 (d, J=2.0 Hz, 1H), 8.12-8.03 (m, 2H), 7.95 (d, J=8.7 Hz, 1H), 7.61 (dd, J=8.7, 2.1 Hz, 1H), 7.59-7.53 (m, 3H), 3.48-3.38 (m, 4H), 1.94-1.81 (m, 4H); EIMS m/z 324.2 (M+1)$^+$; HPLC 98.5 area % (290 nm). Anal. Calcd for C$_{18}$H$_{17}$N$_3$OS: C, 66.85; H, 5.30; N, 12.99. Found: C, 66.57; H, 5.46; N, 12.73.

2-(3,4-Difluorophenyl)-5-(3,3-difluoro-N-pyrrolidylamido)benzothiazole (9) was prepared from 5-amino-2-(3,4-difluorophenyl)benzothiazole (74g) and 3,3-difluorpyrrolidine hydrochloride. The product was recrystallized from DCM/hexanes as white crystals (88 mg, 38%); mp 227-228° C.; $^1$H NMR (400 MHz, MeOH-d$_4$) δ 8.19 (dd, J=2.1, 0.5 Hz, 1H), 8.03 (ddd, J=11.3, 7.6, 2.2 Hz, 1H), 7.93-7.84 (m, 2H), 7.55 (dd, J=8.7, 2.1 Hz, 1H), 7.50-7.39 (m, 1H), 3.88 (t, J=12.9 Hz, 2H), 3.76 (t, J=7.4 Hz, 2H), 2.58-2.42 (m, 2H); EIMS m/z 396.0 (M+1)$^+$; HPLC 96.7 area % (254 nm). Anal. Calcd for C$_{18}$H$_{13}$F$_4$N$_3$OS: C, 54.68; H, 3.31; N, 10.63. Found: C, 54.72; H, 3.44; N, 10.72.

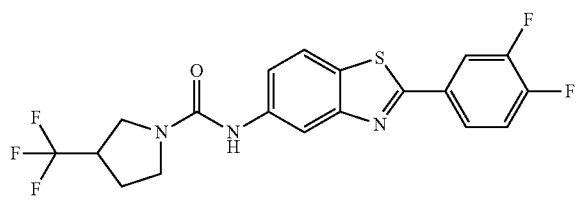 [SMILES: O=C(Nc1ccc2sc(-c3ccc(F)c(F)c3)nc2c1)N1CCC(C(F)(F)F)C1]

2-(3,4-Difluorophenyl)-5-[(3-trifluoromethyl)-N-pyrrolidylamido]benzothiazole (10) was prepared from 5-amino-2-(3,4-difluorophenyl)benzothiazole (74g) and 3-(trifluoromethyl)pyrrolidine hydrochloride. The product was recrystallized from EtOAc/hexanes as a white solid (88 mg, 38%); mp 171-175° C.; $^1$H NMR (400 MHz, Chloroform-d) δ 8.01 (d, J=2.1 Hz, 1H), 7.94 (ddd, J=10.9, 7.6, 2.2 Hz, 1H), 7.83-7.74 (m, 2H), 7.59 (dd, J=8.7, 2.2 Hz, 1H), 7.33-7.21 (m, 1H), 6.33 (s, 1H), 3.83 (dd, J=10.7, 8.2 Hz, 1H), 3.78-3.63 (m, 2H), 3.59 (q, J=7.8 Hz, 1H), 3.14-2.95 (m, J=8.2 Hz, 1H), 2.37-2.17 (m, 2H). EIMS m/z 428.2 (M+1)$^+$; HPLC 95.6 area % (254 nm). Anal. Calcd for C$_{19}$H$_{14}$F$_5$N$_3$OS: C, 53.40; H, 3.30; N, 9.83. Found: C, 53.40; H, 3.40; N, 9.71.

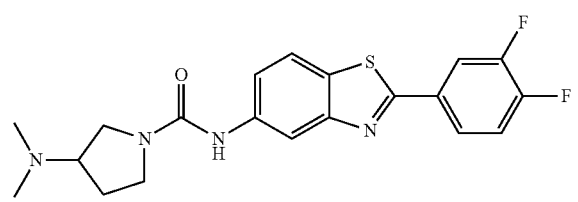 [SMILES: CN(C)C1CCN(C(=O)Nc2ccc3sc(-c4ccc(F)c(F)c4)nc3c2)C1]

2-(3,4-Difluorophenyl)-5-(3-dimethylamino-N-pyrrolidylamido)benzothiazole (11) was prepared from 5-amino-2-(3,4-difluorophenyl)benzothiazole (74g) and 3-dimethylaminopyrrolidine. The product was recrystallized from EtOAc/hexanes as ivory crystals (155 mg, 65%); mp 147-149° C.; $^1$H NMR (400 MHz, DMSO-d$_6$) δ 8.37 (s, 1H), 8.33 (dd, J=2.1, 0.5 Hz, 1H), 8.13 (ddd, J=11.3, 7.7, 2.2 Hz, 1H), 7.98 (dd, J=8.8, 0.5 Hz, 1H), 7.96-7.90 (m, 1H), 7.69-7.58 (m, 2H), 3.69 (dd, J=10.0, 7.0 Hz, 1H), 3.60 (ddd, J=10.6, 8.6, 2.2 Hz, 1H), 3.40-3.34 (m, 1H), 3.14 (dd, J=9.9, 8.3 Hz, 1H), 2.71 (p, J=7.5 Hz, 1H), 2.20 (s, 6H), 2.12-2.03 (m, 1H), 1.80-1.65 (m, 1H); EIMS m/z 403.2 (M+1)$^+$; HPLC 99.5 area % (254 nm). Anal. Calcd for C$_{20}$H$_{20}$F$_2$N$_4$OS·0.25H$_2$O: C, 59.03; H, 5.08; N, 13.77. Found: C, 58.79; H, 4.99; N, 13.76.

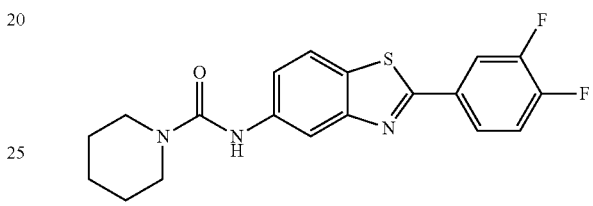

2-(3,4-Difluorophenyl)-5-(N-piperidylamido)benzothiazole (12) was prepared from 5-amino-2-(3,4-difluorophenyl)benzothiazole (74g) and piperidine. The product was recrystallized from DCM/hexanes as white crystals (136 mg, 67%); mp 232-233° C.; $^1$H NMR (400 MHz, DMSO-d$_6$) δ 8.68 (s, 1H), 8.27 (dd, J=2.1, 0.5 Hz, 1H), 8.12 (ddd, J=11.3, 7.7, 2.2 Hz, 1H), 7.97 (dd, J=8.8, 0.5 Hz, 1H), 7.95-7.90 (m, 1H), 7.64 (dt, J=10.5, 8.4 Hz, 1H), 7.58 (dd, J=8.8, 2.1 Hz, 1H), 3.51-3.42 (m, 4H), 1.60 (q, J=5.8, 5.1 Hz, 2H), 1.52 (dd, J=9.9, 5.8 Hz, 4H); EIMS m/z 374.1 (M+1)$^+$; HPLC 99.0 area % (254 nm). Anal. Calcd for C$_{19}$H$_{17}$F$_2$N$_3$OS: C, 61.11; H, 4.59; N, 11.25. Found: C, 61.00; H, 4.58; N, 11.22.

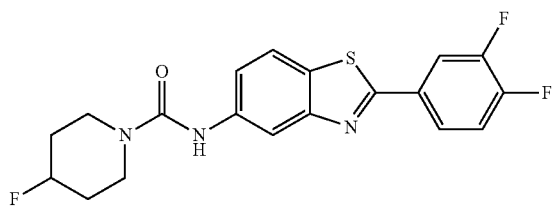 [SMILES: O=C(Nc1ccc2sc(-c3ccc(F)c(F)c3)nc2c1)N1CCC(F)CC1]

2-(3,4-Difluorophenyl)-5-(4-fluoro-N-piperidylamido)benzothiazole (13) was prepared from 5-amino-2-(3,4-difluorophenyl)benzothiazole (74g) and 4-fluoropiperidine hydrochloride. The product was recrystallized from DCM/hexanes as white crystals (135 mg, 68%); mp 231.5-232° C.; $^1$H NMR (400 MHz, DMSO-d$_6$) δ 8.81 (s, 1H), 8.29-8.24 (m, 1H), 8.13 (ddd, J=11.4, 7.7, 2.2 Hz, 1H), 7.98 (dd, J=8.7, 0.5 Hz, 1H), 7.96-7.89 (m, 1H), 7.64 (dt, J=10.5, 8.4 Hz, 1H), 7.57 (dd, J=8.8, 2.1 Hz, 1H), 4.89 (dtt, J=48.6, 7.1, 3.5 Hz, 1H), 3.69-3.57 (m, 2H), 3.52-3.41 (m, 2H), 1.93 (dddd, J=21.3, 17.4, 8.0, 3.8 Hz, 2H), 1.71 (ddtd, J=13.9, 10.7, 7.2, 3.8 Hz, 2H); EIMS m/z 392.1 (M+1)$^+$; HPLC 97.9 area % (254 nm). Anal. Calcd for C$_{19}$H$_{16}$F$_3$N$_3$OS·0.1H$_2$O: C, 58.04; H, 4.15; N, 10.69. Found: C, 57.84; H, 4.10; N, 10.62.

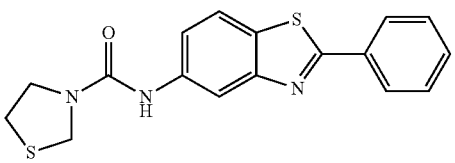 [SMILES: O=C(Nc1ccc2sc(-c3ccccc3)nc2c1)N1CCSC1]

N-(2-Phenylbenzo[d]thiazol-5-yl)pyrrolidine-1-carboxamide (22) was prepared from 5-amino-2-phenylbenzothiazole (74a) and thiazolidine. The product was recrystallized from DCM/hexanes as a white solid (50.5 mg, 26%); mp 177-179° C.; $^1$H NMR (400 MHz, DMSO-$d_6$) δ 8.84 (s, 1H), 8.27 (d, J=2.0 Hz, 1H), 8.13-8.03 (m, 2H), 7.99 (d, J=8.7 Hz, 1H), 7.62-7.53 (m, 4H), 4.59 (s, 2H), 3.76 (t, J=6.3 Hz, 2H), 3.07 (t, J=6.3 Hz, 2H); EIMS m/z 342.0 (M+1)$^+$; HPLC 98.6 area % (254 nm). Anal. Calcd for $C_{17}H_{15}N_3OS_2 \cdot 0.2H_2O$: C, 59.17; H, 4.50; N, 12.18. Found: C, 59.05; H, 4.59; N, 12.10.

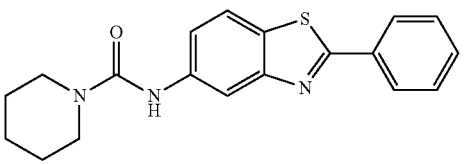 [SMILES: O=C(Nc1ccc2sc(-c3ccccc3)nc2c1)N1CCCCC1]

2-Phenyl-5-(N-piperidylamido)benzothiazole (23) was prepared from 5-amino-2-phenylbenzothiazole (74a) and piperidine. The product was recrystallized from EtOH as a white solid (273 mg, 54%); mp 230-232° C.; $^1$H NMR (400 MHz, DMSO-$d_6$) δ 8.66 (s, 1H), 8.25 (d, J=2.0 Hz, 1H), 8.07 (tddd, J=4.3, 3.4, 2.3, 1.1 Hz, 2H), 7.94 (d, J=8.7 Hz, 1H), 7.61-7.50 (m, 4H), 3.46 (dd, J=6.6, 4.1 Hz, 4H), 1.66-1.56 (m, 2H), 1.56-1.47 (m, 4H); EIMS m/z 338.2 (M+1)$^+$; HPLC 100 area % (254 nm). Anal. Calcd for $C_{19}H_{19}N_3OS$: C, 67.63; H, 5.68; N, 12.45. Found: C, 67.44; H, 5.76; N, 12.36.

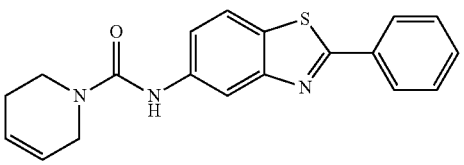 [SMILES: O=C(Nc1ccc2sc(-c3ccccc3)nc2c1)N1CC=CCC1]

N-(2-Phenylbenzo[d]thiazol-5-yl)-3,6-dihydropyridine-1(2H)-carboxamide (24) was prepared from 5-amino-2-phenylbenzothiazole (74a) and 1,2,3,6-tetrahydropyridine. The product was recrystallized from EtOH as ivory crystals (332 mg, 69%); mp 199-200° C.; $^1$H NMR (400 MHz, DMSO-$d_6$) δ 8.68 (s, 1H), 8.26 (dd, J=2.1, 0.5 Hz, 1H), 8.07 (ddq, J=6.5, 3.3, 2.2 Hz, 2H), 7.96 (d, J=8.6 Hz, 1H), 7.64-7.50 (m, 4H), 5.88 (dtt, J=9.9, 3.8, 2.2 Hz, 1H), 5.77 (dtt, J=10.0, 3.1, 1.8 Hz, 1H), 4.00 (p, J=2.8 Hz, 2H), 3.58 (t, J=5.6 Hz, 2H), 2.22-2.11 (m, 2H); EIMS m/z 336.1 (M+1)$^+$; HPLC 100 area % (254 nm). Anal. Calcd for $C_{19}H_{17}N_3OS$: C, 68.04; H, 5.11; N, 12.53. Found: C, 67.77; H, 5.13; N, 12.45.

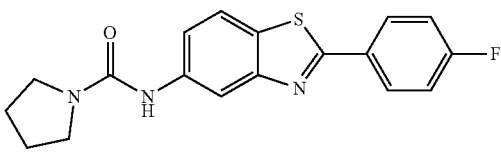 [SMILES: O=C(Nc1ccc2sc(-c3ccc(F)cc3)nc2c1)N1CCCC1]

2-(4-Fluorophenyl)-5-(N-pyrrolidylamido)benzothiazole (26) was prepared from 5-amino-2-(4-fluorophenyl)benzothiazole (74b) and pyrrolidine. The product was recrystallized from EtOH/water as beige crystals (142 mg, 81%); mp 211-213° C.; $^1$H NMR (400 MHz, DMSO-$d_6$) δ 8.34 (s, 1H), 8.31 (d, J=2.1 Hz, 1H), 8.17-8.07 (m, 2H), 7.94 (d, J=8.7 Hz, 1H), 7.60 (dd, J=8.8, 2.1 Hz, 1H), 7.46-7.35 (m, 2H), 3.47-3.35 (m, 4H), 1.93-1.81 (m, 4H); EIMS m/z 342.0 (M+1)$^+$; HPLC 97.4 area % (254 nm). Anal. Calcd for $C_{18}H_{16}FN_3OS$: C, 63.33; H, 4.72; N, 12.31. Found: C, 63.26; H, 4.73; N, 12.02.

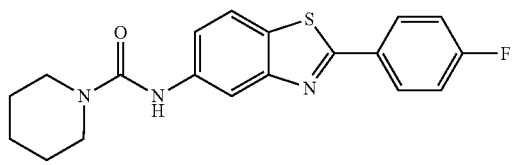 [SMILES: O=C(Nc1ccc2sc(-c3ccc(F)cc3)nc2c1)N1CCCCC1]

2-(4-Fluorophenyl)-5-(N-piperidylamido)benzothiazole (27) was prepared from 5-amino-2-(4-fluorophenyl)benzothiazole (74b) and piperidine. The product was recrystallized from EtOH as ivory crystals (85 mg, 47%); mp 227-229° C.; $^1$H NMR (400 MHz, DMSO-$d_6$) δ 8.67 (s, 1H), 8.24 (d, J=2.0 Hz, 1H), 8.18-8.07 (m, 2H), 7.94 (d, J=8.7 Hz, 1H), 7.55 (dd, J=8.7, 2.1 Hz, 1H), 7.46-7.35 (m, 2H), 3.46 (t, J=5.4 Hz, 4H), 1.63-1.55 (m, 2H), 1.55-1.48 (m, 4H); EIMS m/z 356.1 (M+1)$^+$; HPLC 99.1 area % (254 nm). Anal. Calcd for $C_{19}H_{18}FN_3OS$: C, 64.21; H, 5.10; N, 11.82. Found: C, 64.07; H, 5.00; N, 11.74.

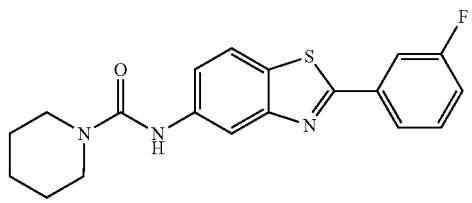 [SMILES: O=C(Nc1ccc2sc(-c3cccc(F)c3)nc2c1)N1CCCCC1]

2-(3-Fluorophenyl)-5-(N-piperidylamido)benzothiazole (29) was prepared from 5-amino-2-(3-fluorophenyl)benzothiazole (74c) and piperidine. The product was recrystallized from EtOH as white crystals (123 mg, 66%); mp 216-217° C.; $^1$H NMR (400 MHz, DMSO-$d_6$) δ 8.69 (s, 1H), 8.27 (d, J=2.0 Hz, 1H), 7.97 (d, J=8.8 Hz, 1H), 7.94-7.83 (m, 2H), 7.68-7.61 (m, 1H), 7.58 (dd, J=8.7, 2.1 Hz, 1H), 7.48-7.38 (m, 1H), 3.46 (t, J=5.4 Hz, 4H), 1.64-1.56 (m, 2H), 1.53 (q, J=5.3, 4.4 Hz, 4H); EIMS m/z 356.2 (M+1)$^+$; HPLC 99.3 area % (254 nm). Anal. Calcd for $C_{19}H_{18}FN_3OS$: C, 64.21; H, 5.10; N, 11.82. Found: C, 64.10; H, 5.04; N, 11.86.

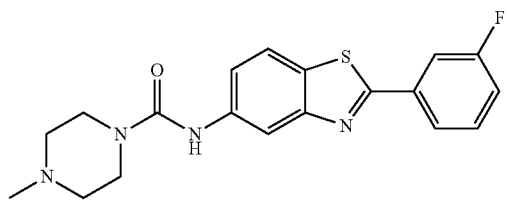 [SMILES: CN1CCN(C(=O)Nc2ccc3sc(-c4cccc(F)c4)nc3c2)CC1]

N-(2-(3-Fluorophenyl)benzothiazol-5-yl)-4-methylpiperazine-1-carboxamide (30) was prepared from 5-amino-2-(3-fluorophenyl)benzothiazole (74c) and 1-methylpiperazine. The product was recrystallized from EtOH as a white powder (104 mg, 50%); mp 224-226° C.; $^1$H NMR (400 MHz, DMSO-$d_6$) δ 8.75 (s, 1H), 8.27 (dd, J=2.1, 0.5 Hz, 1H), 7.98 (dd, J=8.7, 0.5 Hz, 1H), 7.94-7.83 (m, 2H), 7.68-7.60 (m, 1H), 7.58 (dd, J=8.8, 2.1 Hz, 1H), 7.43 (tdd, J=8.5, 2.7, 0.9 Hz, 1H), 3.48 (t, J=5.0 Hz, 4H), 2.34 (t, J=5.0 Hz, 4H), 2.22 (s, 3H); EIMS m/z 370.9 (M+1)$^+$; HPLC 99.4 area % (254 nm). Anal. Calcd for $C_{19}H_{19}FN_4OS$: C, 61.60; H, 5.17; N, 15.12. Found: C, 61.47; H, 5.26; N, 14.95.

2-(2-Fluorophenyl)-5-(N-piperidylamido)benzothiazole (33) was prepared from 5-amino-2-(2-fluorophenyl)benzothiazole (74d) and piperidine. The product was recrystallized from EtOH as white crystals (120 mg, 64%); mp 213-215° C.; $^1$H NMR (400 MHz, DMSO-$d_6$) δ 8.69 (s, 1H), 8.36 (td, J=7.8, 1.8 Hz, 1H), 8.31 (d, J=2.0 Hz, 1H), 7.99 (d, J=8.7 Hz, 1H), 7.68-7.60 (m, 1H), 7.58 (dd, J=8.8, 2.1 Hz, 1H), 7.53-7.39 (m, 2H), 3.46 (t, J=5.4 Hz, 4H), 1.60 (q, J=5.8 Hz, 2H), 1.52 (dd, J=7.1, 3.9 Hz, 4H); EIMS m/z

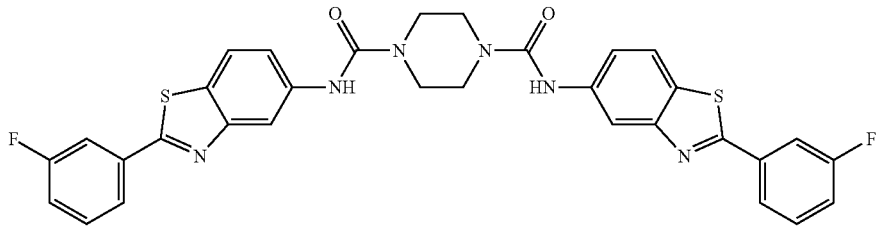 [SMILES: O=C(Nc1ccc2sc(-c3cccc(F)c3)nc2c1)N1CCN(C(=O)Nc2ccc3sc(-c4cccc(F)c4)nc3c2)CC1]

N$^1$,N$^4$-Bis(2-(3-fluorophenyl)benzothiazol-5-yl)piperazine-1,4-dicarboxamide (31) was prepared from 5-amino-2-(4-fluorophenyl)benzothiazole (74c) and piperazine (0.55 equiv). The crude product, which precipitated from the reaction mixture, was filtered off and was purified by suspension in EtOH to give a white powder (129 mg, 66%); mp>° C. dec; $^1$H NMR (400 MHz, DMSO-$d_6$) δ 8.87 (s, 2H), 8.31 (d, J=2.0 Hz, 2H), 8.01 (d, J=8.8 Hz, 2H), 7.95-7.84 (m, 4H), 7.68-7.57 (m, 4H), 7.49-7.38 (m, 2H), 3.59 (s, 8H), EIMS m/z 627.1 (M+1)$^+$; HPLC 100 area % (254 nm). Anal. Calcd for $C_{32}H_{24}F_2N_6O_2S_2.H_2O$: C, 59.61; H, 4.06; N, 13.04. Found: C, 59.47; H, 3.96; N, 13.09.

356.1 (M+1)$^+$; HPLC 100 area % (254 nm). Anal. Calcd for $C_{19}H_{18}FN_3OS.0.2H_2O$: C, 63.56; H, 5.17; N, 11.69. Found: C, 63.36; H, 5.13; N, 11.53.

2-(2,4-Difluorophenyl)-5-(N-pyrrolidylamido)benzothiazole (34) was prepared from 5-amino-2-(2,4-difluorophenyl)benzothiazole (74f) and pyrrolidine. The product was recrystallized from EtOH as beige granules (144 mg, 71%); mp 223-224° C.; $^1$H NMR (400 MHz, DMSO-$d_6$) δ 8.41 (td, J=8.8, 6.6 Hz, 1H), 8.38 (dd, J=2.1, 0.5 Hz, 1H), 8.36 (s, 1H), 7.99 (dd, J=8.7, 0.5 Hz, 1H), 7.64 (dd, J=8.8, 2.1 Hz, 1H), 7.56 (ddd, J=11.7, 9.1, 2.6 Hz, 1H), 7.34 (dddd, J=8.9, 8.1, 2.6, 0.9 Hz, 1H), 3.46-3.37 (m, 4H), 1.94-1.82 (m, 4H); EIMS m/z 360.1 (M+1)$^+$; HPLC 96.7 area % (254 nm). Anal. Calcd for $C_{18}H_{15}F_2N_3OS$: C, 60.16; H, 4.21; N, 11.69. Found: C, 59.95; H, 4.27; N, 11.58.

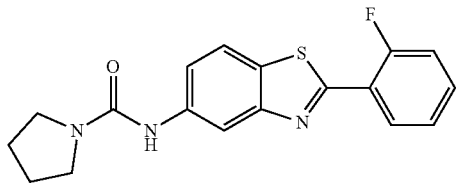 [SMILES: O=C(Nc1ccc2sc(-c3ccccc3F)nc2c1)N1CCCC1]

2-(2-Fluorophenyl)-5-(N-pyrrolidylamido)benzothiazole (32) was prepared from 5-amino-2-(2-fluorophenyl)benzothiazole (74d) and pyrrolidine. The product was recrystallized from EtOH as orange crystals (142 mg, 78%); mp 207-208° C.; $^1$H NMR (400 MHz, DMSO-$d_6$) δ 8.41-8.32 (m, 3H), 7.99 (d, J=8.7 Hz, 1H), 7.68-7.57 (m, 2H), 7.53-7.39 (m, 2H), 3.49-3.37 (m, 4H), 1.93-1.82 (m, 4H); EIMS m/z 342.0 (M+1)$^+$; HPLC 97.9 area % (254 nm). Anal. Calcd for $C_{18}H_{16}FN_3OS.0.1H_2O$: C, 62.99; H, 4.76; N, 12.24. Found: C, 62.77; H, 4.86; N, 11.98.

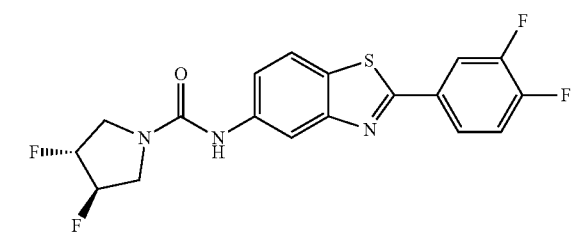

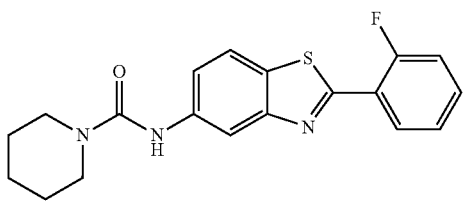 [SMILES: O=C(Nc1ccc2sc(-c3ccccc3F)nc2c1)N1CCCCC1]

(3R,4R)-2-(3,4-Difluorophenyl)-5-(3,4-difluoro-N-pyrrolidylamido)benzothiazole (35) was prepared from 5-amino-2-(3,4-difluorophenyl)benzothiazole (74g) and (3R,4R)-3,4-difluorpyrrolidine hydrochloride. The product was recrystallized from EtOH as white crystals (239 mg, 77%): mp 217-218° C.; $^1$H NMR (400 MHz, DMSO-$d_6$) δ 8.65 (s, 1H), 8.31 (dd, J=2.1, 0.5 Hz, 1H), 8.13 (ddd, J=11.4, 7.7, 2.2 Hz, 1H), 8.01 (dd, J=8.7, 0.5 Hz, 1H), 7.94 (dddd, J=8.6, 4.3, 2.2, 1.3 Hz, 1H), 7.70-7.62 (m, 1H), 7.60 (dd, J=8.8, 2.1 Hz, 1H), 5.44 (dt, J=52.5, 3.1, 1.9 Hz, 2H), 3.90 (d, J=13.3 Hz, 1H), 3.83 (td, J=6.6, 4.6 Hz, 2H), 3.71 (dd, J=13.6, 3.3 Hz, 1H); EIMS m/z 396.1 (M+1)⁻¹; HPLC 96.3 area % (254 nm). Anal. Calcd for $C_{18}H_{13}F_4N_3OS$: C, 54.68; H, 3.31; N, 10.63. Found: C, 54.39; H, 3.28; N, 10.41.

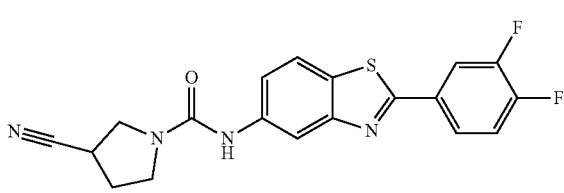 [SMILES: N#CC1CCN(C(=O)Nc2ccc3sc(-c4ccc(F)c(F)c4)nc3c2)C1]

2-(3,4-Difluorophenyl)-5-(3-cyano-N-pyrrolidylamido) benzothiazole (36) was prepared from 5-amino-2-(3,4-difluorophenyl)benzothiazole (74g) and 3-cyanopyrrolidine hydrochloride. The product was recrystallized from EtOAc/hexanes as a white solid (132 mg, 56%); mp 222-224° C.; ¹H NMR (400 MHz, DMSO-$d_6$) δ 8.55 (s, 1H), 8.32 (dd, J=2.1, 0.5 Hz, 1H), 8.13 (ddd, J=11.3, 7.7, 2.2 Hz, 1H), 8.00 (dd, J=8.8, 0.5 Hz, 1H), 7.97-7.89 (m, 1H), 7.69-7.57 (m, 2H), 3.76 (dd, J=10.4, 7.2 Hz, 1H), 3.69-3.62 (m, 1H), 3.66-3.45 (m, 3H), 2.32 (dq, J=13.7, 6.8 Hz, 1H), 2.20 (dq, J=13.2, 6.7 Hz, 1H); EIMS m/z 385.2 (M+1)⁺; HPLC 95.4 area % (254 nm). Anal. Calcd for $C_{19}H_{14}F_2N_4OS$: C, 59.37; H, 3.67; N, 14.58. Found: C, 59.34; H, 3.74; N, 14.37.

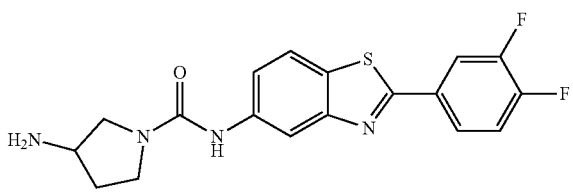 [SMILES: NC1CCN(C(=O)Nc2ccc3sc(-c4ccc(F)c(F)c4)nc3c2)C1]

2-(3,4-Difluorophenyl)-5-(3-amino-N-pyrrolidylamido) benzothiazole (37) was prepared from 5-amino-2-(3,4-difluorophenyl)benzothiazole (74g) and 3-(Boc-amino)pyrrolidine. The product was recrystallized from EtOAc/hexanes to give 5-(3-Boc-amino-N-pyrrolidylamido)-2-(3,4-Difluorophenyl)benzothiazole as a white solid (245 mg, 83%); mp 208-209° C.; ¹H NMR (400 MHz, DMSO-$d_6$) δ 8.38 (s, 1H), 8.34 (d, J=2.0 Hz, 1H), 8.13 (ddd, J=11.3, 7.7, 2.2 Hz, 1H), 7.97 (dd, J=8.7, 0.5 Hz, 1H), 7.95-7.88 (m, 1H), 7.69-7.58 (m, 2H), 7.22 (d, J=6.7 Hz, 1H), 4.03 (dd, J=13.5, 6.4 Hz, 1H), 3.62 (dd, J=10.4, 6.3 Hz, 1H), 3.54 (dt, J=10.2, 7.1 Hz, 1H), 3.42 (dt, J=10.1, 7.4 Hz, 1H), 3.25 (dd, J=10.5, 4.9 Hz, 1H), 2.06 (dq, J=13.5, 6.6 Hz, 1H), 1.93-1.75 (m, 1H), 1.41 (s, 9H); EIMS m/z 475.3 (M+1)⁺; HPLC 100 area % (254 nm). Anal. Calcd for $C_{23}H_{24}F_2N_4OS$: C, 58.22; H, 5.10; N, 11.81. Found: C, 58.41; H, 5.03; N, 11.56.

Trifluoroacetic acid (2.5 mL) was added dropwise by syringe to a suspension of the material above (214 mg, 0.450 mmol) in DCM (7.5 mL). After 30 minutes, the mixture was evaporated under reduced pressure. The residue was neutralized with saturated $NaHCO_3$ solution and extracted into DCM. The dried extract was evaporated to a white solid, which was recrystallized from EtOAc/hexanes (129 mg, 76%): mp>300° C. dec; ¹H NMR (400 MHz, DMSO-$d_6$) δ 8.34 (d, J=2.0 Hz, 1H), 8.32 (s, 1H), 8.12 (ddd, J=11.4, 7.7, 2.2 Hz, 1H), 7.97 (d, J=8.8 Hz, 1H), 7.95-7.89 (m, 1H), 7.69-7.58 (m, 2H), 3.52 (ddd, J=14.8, 9.4, 5.7 Hz, 3H), 3.46-3.35 (m, 1H), 3.08 (dd, J=9.6, 4.1 Hz, 1H), 1.97 (tt, J=12.4, 6.1 Hz, 1H), 1.81 (s, 2H), 1.64 (dq, J=12.7, 6.3 Hz, 1H). EIMS m/z 375.1 (M+1)⁺; HPLC 95.5 area % (254 nm). Anal. Calcd for $C_{18}H_{16}F_2N_4OS \cdot 1.5H_2O$: C, 53.86; H, 4.77; N, 13.96. Found: C, 53.78; H, 4.53; N, 13.73.

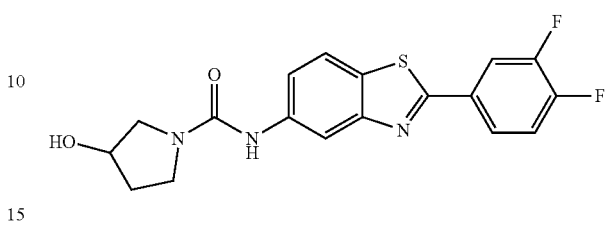

2-(3,4-Difluorophenyl)-5-(3-hydroxy-N-pyrrolidylamido)benzothiazole (38) was prepared from 5-amino-2-(3,4-difluorophenyl)benzothiazole (74g) and 3-hydroxypyrrolidine. The product was recrystallized from EtOH as ivory crystals (159 mg, 69%); mp 211-213° C.; ¹H NMR (400 MHz, DMSO-$d_6$) δ 8.36 (s, 1H), 8.34 (d, J=2.0 Hz, 1H), 8.13 (ddd, J=11.3, 7.7, 2.2 Hz, 1H), 7.97 (d, J=8.8 Hz, 1H), 7.96-7.88 (m, 1H), 7.69-7.58 (m, 2H), 4.98 (d, J=3.6 Hz, 1H), 4.35-4.30 (m, 1H), 3.55-3.43 (m, 3H), 3.34 (dt, J=10.9, 1.7 Hz, 1H), 1.95 (dtd, J=13.2, 8.8, 4.5 Hz, 1H), 1.87-1.79 (m, 1H); EIMS m/z 376.2 (M+1)⁺; HPLC 98.8 area % (254 nm). Anal. Calcd for $C_{18}H_{15}F_2N_3O_2S$: C, 57.59; H, 4.03; N, 11.19. Found: C, 57.82; H, 4.24; N, 10.80.

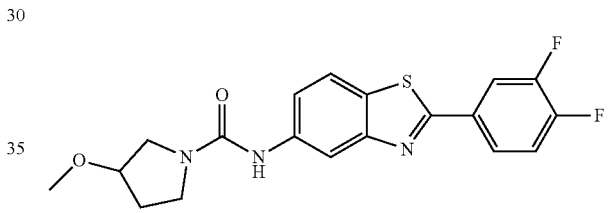

2-(3,4-Difluorophenyl)-5-(3-methoxy-N-pyrrolidylamido)benzothiazole (39) was prepared from 5-amino-2-(3,4-difluorophenyl)benzothiazole (74g) and 3-methoxypyrrolidine. The product was recrystallized from EtOH/water as a cream colored powder (165 mg, 69%); mp 189-190.5° C.; ¹H NMR (400 MHz, DMSO-$d_6$) δ 8.39 (s, 1H), 8.33 (dd, J=2.1, 0.5 Hz, 1H), 8.13 (ddd, J=11.3, 7.7, 2.2 Hz, 1H), 7.98 (dd, J=8.8, 0.5 Hz, 1H), 7.96-7.89 (m, 1H), 7.69-7.58 (m, 2H), 4.04-3.99 (m, 1H), 3.58-3.46 (m, 3H), 3.45-3.35 (m, 1H), 3.27 (s, 3H), 2.06-1.91 (m, 2H); EIMS m/z 390.2 (M+1)⁺; HPLC 96.5 area % (254 nm). Anal. Calcd for $C_{19}H_{17}F_2N_3O_2S$: C, 58.60; H, 4.40; N, 10.79. Found: C, 58.85; H, 4.50; N, 10.54.

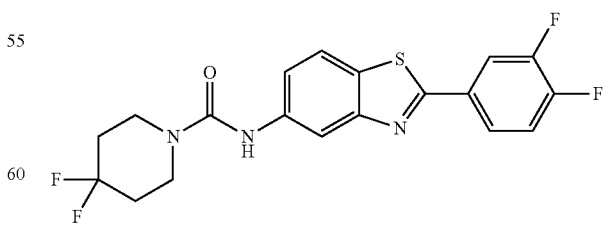

2-(3,4-Difluorophenyl)-5-(4,4-difluoro-N-piperidylamido)benzothiazole (40) was prepared from 5-amino-2-(3,4-difluorophenyl)benzothiazole (74g) and 4,4-difluoropiperidine hydrochloride. The product was recrystallized from DCM/hexanes as a white solid (255 mg, 71%); mp 222-225° C.; $^1$H NMR (400 MHz, DMSO-$d_6$) δ 8.93 (s, 1H), 8.27 (d, J=2.2 Hz, 1H), 8.13 (ddd, J=11.3, 7.7, 2.2 Hz, 1H), 8.00 (dd, J=8.7, 0.5 Hz, 1H), 7.98-7.89 (m, 1H), 7.64 (dt, J=10.5, 8.5 Hz, 1H), 7.57 (dd, J=8.8, 2.1 Hz, 1H), 3.62 (t, J=5.8 Hz, 4H), 2.03 (td, J=14.0, 6.9 Hz, 4H); EIMS m/z 410.0 (M+1)$^+$; HPLC 98.9 area % (254 nm). Anal. Calcd for $C_{19}H_{15}F_4N_3OS$: C, 55.74; H, 3.69; N, 10.26. Found: C, 55.60; H, 3.75; N, 10.20.

Synthesis and Characterization of Intermediates

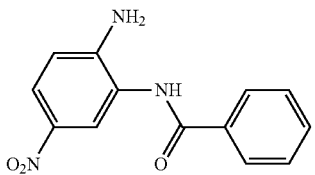 [SMILES: Nc1ccc([N+](=O)[O-])cc1NC(=O)c1ccccc1]

N-(2-Amino-5-nitrophenyl)benzamide (66) (Shalaby et al., *J. Org. Chem.* 64:1065 (1999)). Benzoyl chloride (1.44 g, 10.24 mmol) was added to a solution of 4-nitrobenzene-1,2-diamine (65, 1.54 g, 10.06 mmol) and Et$_3$N (1.5 mL, 10.76 mmol) in THF (100 mL) at –10° C. The mixture stirred overnight while slowly warming to room temperature. The mixture was diluted with water and extracted into EtOAc, and the product was recrystallized from acetonitrile as yellow crystals (1.85 g, 71%): mp 220-222° C.; $^1$H NMR (400 MHz, DMSO-$d_6$) δ 9.74 (s, 1H), 8.14 (d, J=2.7 Hz, 1H), 8.05-7.97 (m, 2H), 7.92 (dd, J=9.1, 2.7 Hz, 1H), 7.65-7.57 (m, 1H), 7.57-7.48 (m, 2H), 6.81 (d, J=9.1 Hz, 1H), 6.59 (s, 2H); HPLC 96.7 area % (254 nm). Anal. Calcd for $C_{13}H_{11}N_3O_3$: C, 60.69; H, 4.31; N, 16.33. Found: C, 60.94; H, 4.40; N, 16.35.

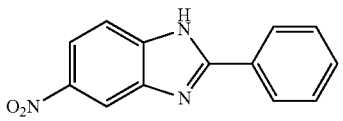 [SMILES: O=[N+]([O-])c1ccc2[nH]c(-c3ccccc3)nc2c1]

5-Nitro-2-phenylbenzimidazole (67)

A mixture of N-(2-amino-5-nitrophenyl)benzamide (66, 2.69 g, 10.50 mmol) and BF$_3$ etherate (1.5 mL, 12.92 mmol) in 1,4-dioxane (150 mL) was refluxed for 3 h. After cooling, the mixture was diluted with water and extracted into EtOAc. The product was purified on a column of silica gel eluting with hexanes/EtOAc (7:3) followed by recrystallization from EtOAc/hexanes as pale yellow crystals (1.07 g, 43%): mp 205-207° C. dec; $^1$H NMR (400 MHz, DMSO-$d_6$ δ 13.61 (s, 1H), 8.49 (s, 1H), 8.27-8.20 (m, 2H), 8.14 (dd, J=8.9, 2.3 Hz, 1H), 7.78 (s, 1H), 7.66-7.52 (m, 3H); HPLC 100 area % (265 nm). Anal. Calcd for $C_{13}H_9N_3O_2 \cdot 0.5H_2O$: C, 62.90; H, 4.06; N, 16.93. Found: C, 62.99; H, 4.08; N, 16.91.

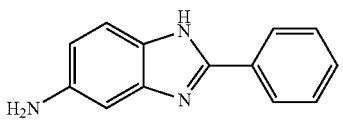

5-Amino-2-phenylbenzimidazole (68) (Shi et al., *Bioorg. Med. Chem.* 22:4735 (2014)). A mixture of 5-nitro-2-phenylbenzimidazole (67, 2.25 g, 9.43 mmol) and tin(II) dichloride dihydrate (8.18 g, 36.75) in concd HCl (30 mL) was refluxed for 2 h. The cooled reaction mixture was poured over ice-water. The mixture was basified to pH 10 and extracted into EtOAc. A solution of the crude product in hot EtOH was treated with Norit and filtered. The filtrate was diluted with water to give crystals (1.51 g, 77%): mp>285° C. dec; $^1$H NMR (400 MHz, DMSO-$d_6$) δ 12.29 (s, 1H), 8.06 (d, J=7.5 Hz, 2H), 7.54-7.45 (m, 2H), 7.45-7.36 (m, 1H), 7.28 (d, J=8.5 Hz, 1H), 6.68 (s, 1H), 6.53 (dd, J=8.5, 2.1 Hz, 1H), 4.94 (s, 2H); HPLC 98.2 area % (320 nm). Anal. Calcd for $C_{13}H_{11}N_3 \cdot 0.1H_2O$: C, 73.98; H, 5.35; N, 19.91. Found: C, 74.13; H, 5.33; N, 19.71.

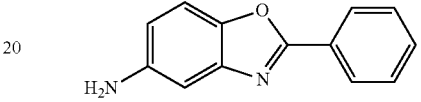

5-Amino-2-phenylbenzoxazole (70) (Chancellor et al., *J. Med. Chem.* 54:3241 (2011)). 2,4-Diaminophenol dihydrochloride (69, 2.96 g, 15.03 mmol) and benzoic acid (1.84 g, 15.07 mmol) were added simultaneously to PPA (11.16 g) at 110° C. The temperature was increased to 180° C. and the mixture was stirred for 4 h. The cooled, solidified reaction mixture was dissolved incrementally by partitioning between saturated sodium bicarbonate solution and EtOAc (total of four extractions). The product was purified on a column of silica gel eluting with 2% MeOH in DCM, followed by recrystallization from EtOH/H$_2$O to give light brown crystals (2.01 g, 63%): mp 154° C.; $^1$H NMR (400 MHz, DMSO-$d_6$) δ 8.19-8.09 (m, 2H), 7.65-7.52 (m, 3H), 7.42 (dd, J=8.6, 0.5 Hz, 1H), 6.88 (dd, J=2.2, 0.6 Hz, 1H), 6.68 (dd, J=8.7, 2.2 Hz, 1H), 5.11 (s, 2H); HPLC 99.2 area % (290 nm). Anal. Calcd for $C_{13}H_{10}N_2O$: C, 74.27; H, 4.79; N, 13.33. Found: C, 74.36; H, 4.90; N, 13.23.

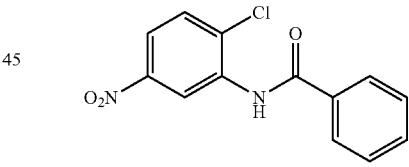

N-(2-Chloro-5-nitrophenyl)benzamide (72a) (Schmidt et al., *Chem. Ber.* 114:1099 (1981); Chakravarty et al., *J. Bangladesh Chem. Soc.* 9:173 (1996); Goldsmith et al., WO 2007/059157). Benzoyl chloride (2.63 g, 18.71 mmol) was added dropwise by syringe to a solution of 2-chloro-5-nitroaniline (71a, 3.06 g, 17.72 mmol) in dry pyridine (7.5 mL) under argon, resulting in the formation of a precipitate. More pyridine (7.5 mL) was added, and the mixture was stirred overnight. The reaction mixture was poured into water. The precipitated product was recrystallized from EtOH as white crystals (4.62 g, 95%): mp 171-172° C.; $^1$H NMR (400 MHz, DMSO-$d_6$) δ 10.35 (s, 1H), 8.58 (d, J=2.8 Hz, 1H), 8.13 (dd, J=8.9, 2.8 Hz, 1H), 8.08-7.97 (m, 2H), 7.88 (d, J=8.8 Hz, 1H), 7.69-7.61 (m, 1H), 7.61-7.52 (m, 2H); HPLC 100 area % (265 nm). Anal. Calcd for $C_{13}H_9ClN_2O_3$: C, 56.44; H, 3.28; N, 10.13. Found: C, 56.43; H, 3.19; N, 10.15.

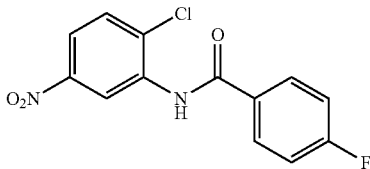 [SMILES: O=C(Nc1cc([N+](=O)[O-])ccc1Cl)c1ccc(F)cc1]

N-(2-Chloro-5-nitrophenyl)-4-fluorobenzamide (72b) (Goldsmith et al., WO 2007059157; Cardullo et al., *Synlett* 47 (2009)) was prepared analogously to 72a from 4-fluorobenzoyl chloride (1.94 g, 12.24 mmol) and 2-chloro-5-nitroaniline (71a, 1.73 g, 10.00 mmol) in pyridine (20 mL). The product was purified on a column of silica gel eluting with 20-33% EtOAc in hexanes, followed by recrystallization from EtOAc/hexanes to give a solid (2.36 g, 80%): mp 169-170° C.; $^1$H NMR (400 MHz, DMSO-$d_6$) δ 10.40 (s, 1H), 8.55 (d, J=2.7 Hz, 1H), 8.13 (dd, J=8.9, 2.8 Hz, 1H), 8.11-8.02 (m, 2H), 7.88 (d, J=8.9 Hz, 1H), 7.47-7.36 (m, 2H); HPLC 100 area % (254 nm). Anal. Calcd for $C_{13}H_8ClFN_2O_3$: C, 52.99; H, 2.74; N, 9.51. Found: C, 53.09; H, 2.80; N, 9.44.

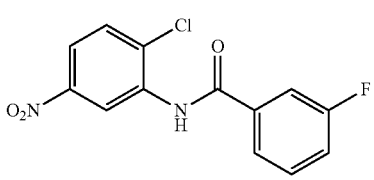 [SMILES: O=C(Nc1cc([N+](=O)[O-])ccc1Cl)c1cccc(F)c1]

N-(2-Chloro-5-nitrophenyl)-3-fluorobenzamide (72c) was prepared analogously to 72a from 3-fluorobenzoyl chloride (1.75 g, 11.04 mmol) and 2-chloro-5-nitroaniline (71a, 1.75 g, 10.13 mmol) in pyridine (total of 10 mL). The product was recrystallized from EtOH as white crystals (2.79 g, 90%): mp 175-176° C.; $^1$H NMR (400 MHz, DMSO-$d_6$) δ 10.49 (s, 1H), 8.54 (d, J=2.8 Hz, 1H), 8.15 (dd, J=8.9, 2.8 Hz, 1H), 7.94-7.84 (m, 2H), 7.81 (ddd, J=9.8, 2.7, 1.5 Hz, 1H), 7.64 (td, J=8.0, 5.8 Hz, 1H), 7.51 (tdd, J=8.5, 2.7, 1.0 Hz, 1H); HPLC 100 area % (265 nm). Anal. Calcd for $C_{13}H_8ClFN_2O_3$: C, 52.99; H, 2.74; N, 9.51. Found: C, 52.76; H, 2.86; N, 9.36.

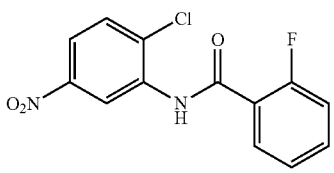 [SMILES: O=C(Nc1cc([N+](=O)[O-])ccc1Cl)c1ccccc1F]

N-(2-Chloro-5-nitrophenyl)-2-fluorobenzamide (72d) was prepared analogously to 72a from 2-fluorobenzoyl chloride (1.78 g, 11.22 mmol) and 2-chloro-5-nitroaniline (71a, 1.75 g, 10.14 mmol) in pyridine (total of 10 mL). The product was recrystallized from EtOH as white crystals (2.32 g, 77%): mp 184-185° C.; $^1$H NMR (400 MHz, DMSO-$d_6$) δ 10.29 (s, 1H), 8.80 (d, J=2.8 Hz, 1H), 8.10 (dd, J=8.8, 2.8 Hz, 1H), 7.88 (d, J=8.9 Hz, 1H), 7.84 (ddd, J=7.7, 1.8 Hz, 1H), 7.65 (dddd, J=8.4, 7.3, 5.3, 1.9 Hz, 1H), 7.45-7.34 (m, 2H); HPLC 100 area % (265 nm). Anal. Calcd for $C_{13}H_8ClFN_2O_3$: C, 52.99; H, 2.74; N, 9.51. Found: C, 52.74; H, 2.79; N, 9.36.

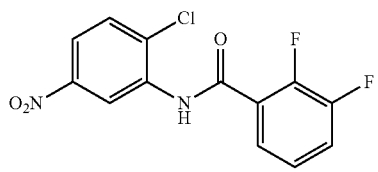 [SMILES: O=C(Nc1cc([N+](=O)[O-])ccc1Cl)c1cccc(F)c1F]

N-(2-Chloro-5-nitrophenyl)-2,3-difluorobenzamide (72e) was prepared analogously to 72a from 2,3-difluorobenzoyl chloride (2.72 g, 15.40 mmol) and 2-chloro-5-nitroaniline (71a, 2.60 g, 15.04 mmol). The product was recrystallized from EtOH as white needles (2.88 g, 61%): mp 177-178° C.; $^1$H NMR (400 MHz, DMSO-$d_6$) δ 10.50 (s, 1H), 8.75 (d, J=2.8 Hz, 1H), 8.12 (dd, J=8.9, 2.8 Hz, 1H), 7.89 (d, J=8.8 Hz, 1H), 7.74-7.66 (m, 1H), 7.63 (ddt, J=11.1, 5.9, 1.6 Hz, 1H), 7.39 (tdd, J=8.1, 4.8, 1.5 Hz, 1H); HPLC 100 area % (265 nm). Anal. Calcd for $C_{13}H_7ClF_2N_2O_3$: C, 49.94; H, 2.26; N, 8.96. Found: C, 49.93; H, 2.26; N, 8.98.

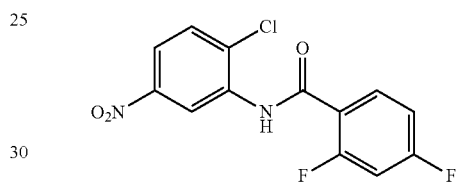

N-(2-Chloro-5-nitrophenyl)-2,4-difluorobenzamide (72f) was prepared analogously to 72a from 2,4-difluorobenzoyl chloride (2.75 g, 15.58 mmol) and 2-chloro-5-nitroaniline (71a, 2.60 g, 15.07 mmol). The product was recrystallized from EtOH as a white solid (2.98 g, 63%): mp 193-194° C.; $^1$H NMR (400 MHz, DMSO-$d_6$) δ 10.28 (s, 1H), 8.79 (d, J=2.7 Hz, 1H), 8.10 (dd, J=8.9, 2.8 Hz, 1H), 7.92 (td, J=8.6, 6.6 Hz, 1H), 7.88 (d, J=8.9 Hz, 1H), 7.53-7.42 (m, 1H), 7.34-7.24 (m, 1H); HPLC 98.6 area % (265 nm). Anal. Calcd for $C_{13}H_7ClF_2N_2O_3$: C, 49.94; H, 2.26; N, 8.96. Found: C, 49.95; H, 2.39; N, 8.86.

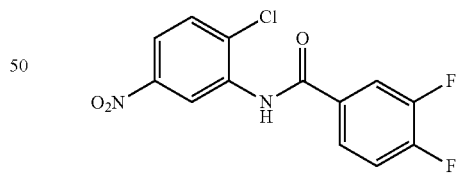

N-(2-Chloro-5-nitrophenyl)-3,4-difluorobenzamide (72g) was prepared analogously to 72a from 3,4-difluorobenzoyl chloride (2.77 g, 15.69 mmol) and 2-chloro-5-nitroaniline (71a, 2.60 g, 15.07 mmol). The product was recrystallized from EtOH as white crystals (3.84 g, 82%): mp 149-51° C.; $^1$H NMR (400 MHz, DMSO-$d_6$) δ 10.50 (s, 1H), 8.53 (d, J=2.7 Hz, 1H), 8.15 (dd, J=8.9, 2.8 Hz, 1H), 8.06 (ddd, J=11.4, 7.8, 2.2 Hz, 1H), 7.95-7.89 (m, 1H), 7.89 (d, J=8.9 Hz, 1H), 7.67 (dt, J=10.5, 8.3 Hz, 1H); HPLC 99.1 area % (265 nm). Anal. Calcd for $C_{13}H_7ClF_2N_2O_3$: C, 49.94; H, 2.26; N, 8.96. Found: C, 49.87; H, 2.29; N, 8.98.

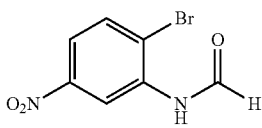 [SMILES: O=CNc1cc([N+](=O)[O-])ccc1Br]

N-(2-Bromo-5-nitrophenyl)formamide (72h) (Spieler et al., *Helv. Chim. Acta* 33:1429 (1950)). A mixture of 2-bromo-5-nitroanline (71b, 3.38 g, 15.57 mmol) in formic acid (96%, 25 mL) was refluxed for 2 h. The cooled reaction mixture was poured in cold water (350 mL) to an off-white granular solid (3.69 g, 97%): $^1$H NMR (400 MHz, DMSO-$d_6$) δ 10.13 (s, 1H), 9.01 (d, J=2.7 Hz, 1H), 8.46 (s, 1H), 7.98 (d, J=8.8 Hz, 1H), 7.91 (dd, J=8.9, 2.7 Hz, 1H); HPLC 98.2 area % (254 nm).

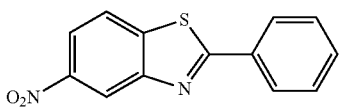

5-Nitro-2-phenylbenzothiazole (73a). A mixture of N-(2-chloro-5-nitrophenyl)benzamide (72a, 3.00 g, 10.85 mmol), sodium sulfide nonahydrate (2.96 g, 12.34 mmol) and sulfur (397 mg, 12.37 mmol) in EtOH (100 mL) was refluxed for 2.5 h. The cooled reaction mixture was evaporated under reduced pressure, diluted with 1 M HCl (100 mL) and extracted into EtOAc. The product was purified on a column of silica gel eluting in DCM, followed by recrystallization from EtOH to give white needles (1.57 g, 57%): mp 195-196° C.; $^1$H NMR (400 MHz, DMSO-$d_6$) δ 8.82 (d, J=2.3 Hz, 1H), 8.45 (d, J=8.8 Hz, 1H), 8.30 (dd, J=8.8, 2.3 Hz, 1H), 8.15 (ddt, J=8.4, 3.1, 1.9 Hz, 2H), 7.74-7.57 (m, 3H); HPLC 100 area % (290 nm). Anal. Calcd for $C_{13}H_8N_2O_2S$: C, 60.93; H, 3.15; N, 10.93. Found: C, 90.95; H, 2.98; N, 11.03.

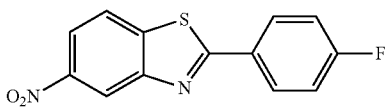

5-Nitro-2-(4-fluorophenyl)benzothiazole (73b) was prepared analogously to 73a from N-(2-chloro-5-nitrophenyl)-4-fluorobenzamide (72b, 1.50 g, 5.09 mmol) as a white solid (810 mg, 58%): mp 219° C.; $^1$H NMR (400 MHz, DMSO-$d_6$) δ 8.82 (dd, J=2.3, 0.5 Hz, 1H), 8.46 (dd, J=8.9, 0.5 Hz, 1H), 8.30 (dd, J=8.8, 2.3 Hz, 1H), 8.27-8.16 (m, 2H), 7.52-7.39 (m, 2H); HPLC 100 area % (290 nm). Anal. Calcd for $C_{13}1_7FN_2O_2S$: C, 56.93; H, 2.57; N, 10.21. Found: C, 56.84; H, 2.62; N, 10.14.

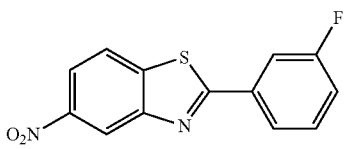

5-Nitro-2-(3-fluorophenyl)benzothiazole (73c) was prepared analogously to 73a from N-(2-chloro-5-nitrophenyl)-3-fluorobenzamide (72c, 2.58 g, 8.74 mmol) as a white solid (1.42 g, 59%): mp 153-154° C.; $^1$H NMR (400 MHz, DMSO-$d_6$) δ 8.84 (d, J=2.2 Hz, 1H), 8.48 (d, J=8.9 Hz, 1H), 8.32 (dd, J=8.9, 2.3 Hz, 1H), 7.99 (dt, J=7.7, 1.3 Hz, 1H), 7.95 (ddd, J=9.7, 2.6, 1.6 Hz, 1H), 7.67 (td, J=8.0, 5.9 Hz, 1H), 7.51 (tdd, J=8.5, 2.6, 0.9 Hz, 1H); HPLC 100 area % (290 nm). Anal. Calcd for $C_{13}H_7FN_2O_2S$: C, 56.93; H, 2.57; N, 10.21. Found: C, 56.96; H, 2.69; N, 10.25.

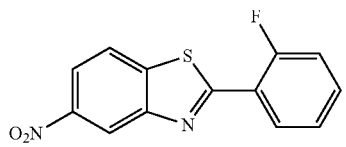 [SMILES: O=[N+]([O-])c1ccc2sc(-c3ccccc3F)nc2c1]

5-Nitro-2-(2-fluorophenyl)benzothiazole (73d) was prepared analogously to 73a from N-(2-chloro-5-nitrophenyl)-2-fluorobenzamide (72d, 2.35 g, 7.99 mmol) as a white solid (1.35 g, 62%): mp 202° C.; $^1$H NMR (400 MHz, DMSO-$d_6$) δ 8.88 (d, J=2.2 Hz, 1H), 8.49 (d, J=8.8 Hz, 1H), 8.41 (td, J=7.7, 1.7 Hz, 1H), 8.33 (dd, J=8.9, 2.2 Hz, 1H), 7.72 (tdd, J=7.6, 5.3, 1.7 Hz, 1H), 7.59-7.45 (m, 2H); HPLC 100 area % (290 nm). Anal. Calcd for $C_{13}H_7FN_2O_2S$: C, 56.93; H, 2.57; N, 10.21. Found: C, 56.89; H, 2.61; N, 10.14.

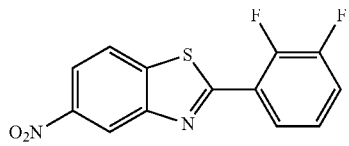 [SMILES: O=[N+]([O-])c1ccc2sc(-c3cccc(F)c3F)nc2c1]

5-Nitro-2-(2,3-difluorophenyl)benzothiazole (73e) was prepared analogously to 73a from N-(2-chloro-5-nitrophenyl)-2,3-difluorobenzamide (72e, 2.77 g, 8.86 mmol), but with column chromatography eluting with 33-50% DCM is hexanes, as a white solid (1.67 g, 67%): mp 157-158° C.; $^1$H NMR (400 MHz, DMSO-$d_6$) δ 8.89 (dd, J=2.2, 0.5 Hz, 1H), 8.51 (dd, J=8.9, 0.5 Hz, 1H), 8.35 (dd, J=8.9, 2.2 Hz, 1H), 8.16 (ddt, J=7.9, 6.3, 1.6 Hz, 1H), 7.74 (dtd, J=10.4, 8.1, 1.6 Hz, 1H), 7.48 (tdd, J=8.2, 5.0, 1.6 Hz, 1H); HPLC 99.4 area % (290 nm). Anal. Calcd for $C_{13}H_6F_2N_2O_2S$: C, 53.43; H, 2.07; N, 9.59. Found: C, 53.43; H, 2.00; N, 9.68.

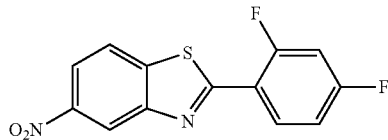 [SMILES: O=[N+]([O-])c1ccc2sc(-c3ccc(F)cc3F)nc2c1]

5-Nitro-2-(2,4-difluorophenyl)benzothiazole (73○ was prepared analogously to 73a from N-(2-chloro-5-nitrophenyl)-2,4-difluorobenzamide (72f, 2.95 g, 9.45 mmol), but with column chromatography eluting with hexanes/DCM (1:1), as a white solid (1.71 g, 62%): mp 207-208° C.; $^1$H NMR (400 MHz, DMSO-$d_6$) δ 8.85 (dd, J=2.2, 0.5 Hz, 1H), 8.47 (d, J=8.9 Hz, 1H), 8.44 (td, J=8.8, 6.5 Hz, 1H), 8.32 (dd, J=8.9, 2.2 Hz, 1H), 7.62 (ddd, J=11.8, 9.1, 2.5 Hz, 1H), 7.39 (dddd, J=8.9, 8.0, 2.6, 0.9 Hz, 1H); HPLC 98.2 area % (254 nm). Anal. Calcd for $C_{13}H_6F_2N_2O_2S$: C, 53.43; H, 2.07; N, 9.59. Found: C, 53.36; H, 2.06; N, 9.74.

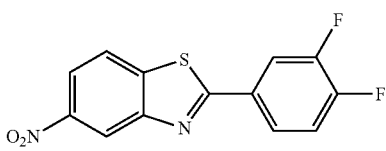 [SMILES: O=[N+]([O-])c1ccc2sc(-c3ccc(F)c(F)c3)nc2c1]

5-Nitro-2-(3,4-difluorophenyl)benzothiazole (73g) was prepared analogously to 73a from N-(2-chloro-5-nitrophenyl)-3,4-difluorobenzamide (72g, 3.78 g, 12.09 mmol), but the crude product was directly recrystallized from EtOH as a white solid (3.00 g, 85%): mp 175-196° C.; $^1$H NMR (400 MHz, DMSO-$d_6$) δ 8.84-8.79 (m, 1H), 8.48 (dt, J=8.8, 0.4 Hz, 1H), 8.31 (dd, J=8.8, 2.2 Hz, 1H), 8.20 (ddd, J=11.3, 7.6, 2.3 Hz, 1H), 8.02 (dddd, J=8.7, 4.3, 2.3, 1.4 Hz, 1H), 7.69 (dt, J=10.5, 8.4 Hz, 1H); HPLC 97.6 area % (290 nm). Anal. Calcd for $C_{13}H_6F_2N_2O_2S$: C, 53.43; H, 2.07; N, 9.59. Found: C, 53.18; H, 2.09; N, 9.59.

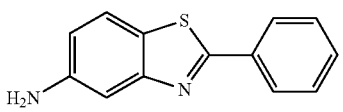

5-Amino-2-(phenyl)benzothiazole (74a)

5-nitro-2-phenylbenzothiazole (73a, 1.87 g, 7.30 mmol), iron powder (2.21 g, 39.57 mmol), and ammonium chloride (818 mg, 15.30 mmol) in EtOH (100 mL) and water (50 mL) was stirred at reflux for 2 h, until the reaction was complete by HPLC. The hot mixture was filtered through Celite, and the filtrate was evaporated to near dryness under reduced pressure. The residue was diluted with water and extracted into DCM. The product was recrystallized from EtOH as yellow crystals (1.47 g, 89%): mp 205-206° C.; $^1$H NMR (400 MHz, DMSO-$d_6$) δ 8.08-7.97 (m, 2H), 7.71 (dd, J=8.6, 0.5 Hz, 1H), 7.61-7.49 (m, 3H), 7.17 (dd, J=2.2, 0.5 Hz, 1H), 6.79 (dd, J=8.6, 2.2 Hz, 1H), 5.33 (s, 2H); HPLC 100 area % (254 nm). Anal. Calcd for $C_{13}H_{10}N_2S$: C, 69.00; H, 4.45; N, 12.38. Found: C, 69.07; H, 4.59; N, 12.19.

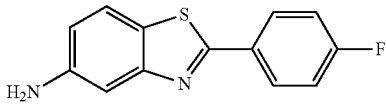

5-Amino-2-(4-fluorophenyl)benzothiazole (74b) was prepared analogously to 74a from 5-nitro-2-(4-fluorophenyl)benzothiazole (73b, 1.57 g, 5.73 mmol) and was recrystallized from EtOH/water as yellow crystals (1.10 g, 79%): mp 168-169° C.; $^1$H NMR (400 MHz, DMSO-$d_6$) δ 8.13-8.02 (m, 2H), 7.69 (dd, J=8.6, 0.5 Hz, 1H), 7.44-7.30 (m, 2H), 7.16 (dd, J=2.2, 0.6 Hz, 1H), 6.79 (ddd, J=8.6, 2.2, 0.6 Hz, 1H), 5.34 (s, 2H); HPLC 100 area % (254 nm). Anal. Calcd for $C_{13}H_9FN_2S \cdot 0.5H_2O$: C, 61.64; H, 3.98; N, 11.06. Found: C, 61.62; H, 4.06; N, 10.97.

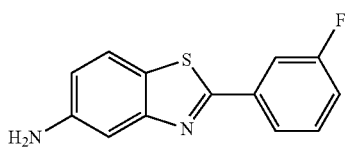

5-Amino-2-(3-fluorophenyl)benzothiazole (74c) was prepared analogously to 74a from 5-nitro-2-(3-fluorophenyl)benzothiazole (73c, 1.41 g, 5.15 mmol) as yellow crystals (1.07 g, 85%): mp 194-195° C.; $^1$H NMR (400 MHz, DMSO-$d_6$) δ 7.88-7.77 (m, 2H), 7.73 (d, J=8.6 Hz, 1H), 7.59 (td, J=8.0, 5.9 Hz, 1H), 7.39 (td, J=8.6, 2.6 Hz, 1H), 7.18 (d, J=2.1 Hz, 1H), 6.81 (dd, J=8.6, 2.2 Hz, 1H), 5.38 (s, 2H); HPLC 100 area % (254 nm). Anal. Calcd for $C_{13}H_9FN_2S$: C, 63.92; H, 3.71; N, 11.47. Found: C, 64.21; H, 3.76; N, 11.54.

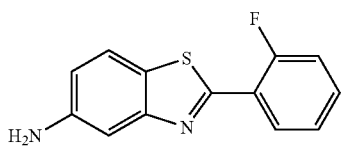

5-Amino-2-(2-fluorophenyl)benzothiazole (74d) was prepared analogously to 74a from 5-nitro-2-(2-fluorophenyl)benzothiazole (73d, 1.33 g, 4.85 mmol) as yellow crystals (1.02 g, 86%): mp 202-203° C.; $^1$H NMR (400 MHz, DMSO-$d_6$) δ 8.33 (td, J=7.8, 1.8 Hz, 1H), 7.76 (d, J=8.6 Hz, 1H), 7.60 (dddd, J=8.6, 7.2, 5.3, 1.8 Hz, 1H), 7.51-7.36 (m, 2H), 7.22 (d, J=2.1 Hz, 1H), 6.84 (dd, J=8.6, 2.2 Hz, 1H), 5.42 (s, 2H); HPLC 100 area % (254 nm). Anal. Calcd for $C_{13}H_9FN_2S$: C, 63.92; H, 3.71; N, 11.47. Found: C, 64.00; H, 3.68; N, 11.48.

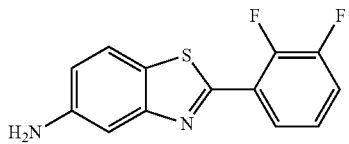

5-Amino-2-(2,3-difluorophenyl)benzothiazole (74e) was prepared analogously to 74a from 5-nitro-2-(2,3-difluorophenyl)benzothiazole (73e, 1.65 g, 5.64 mmol) as yellow crystals (1.37 g, 92%): mp 194° C.; $^1$H NMR (400 MHz, DMSO-$d_6$) δ 8.09 (ddt, J=8.0, 6.3, 1.6 Hz, 1H), 7.78 (dd, J=8.6, 0.5 Hz, 1H), 7.69-7.57 (m, 1H), 7.41 (tdd, J=8.2, 5.1, 1.6 Hz, 1H), 7.22 (dd, J=2.2, 0.5 Hz, 1H), 6.86 (dd, J=8.6, 2.2 Hz, 1H), 5.40 (s, 2H); HPLC 100 area % (254 nm). Anal. Calcd for $C_{13}H_8F_2N_2S$: C, 59.53; H, 3.07; N, 10.68. Found: C, 59.33; H, 3.21; N, 10.69.

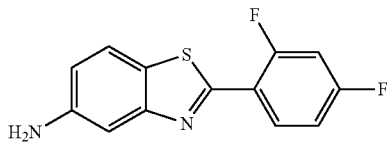

5-Amino-2-(2,4-difluorophenyl)benzothiazole (74f) was prepared analogously to 74a from 5-nitro-2-(2,4-difluorophenyl)benzothiazole (73f, 1.69 g, 5.77 mmol) as a yellow solid (1.38 g, 92%): mp 192-193° C.; $^1$H NMR (400 MHz, DMSO-d$_6$) δ 8.37 (td, J=8.8, 6.6 Hz, 1H), 7.75 (d, J=8.6 Hz, 1H), 7.53 (ddd, J=11.8, 9.2, 2.6 Hz, 1H), 7.31 (dddd, J=9.0, 8.1, 2.6, 0.9 Hz, 1H), 7.20 (dd, J=2.1, 0.5 Hz, 1H), 6.83 (dd, J=8.6, 2.2 Hz, 1H), 5.37 (s, 2H); HPLC 100 area % (254 nm). Anal. Calcd for C$_{13}$H$_8$F$_2$N$_2$S: C, 59.53; H, 3.07; N, 10.68. Found: C, 59.33; H, 3.21; N, 10.69.

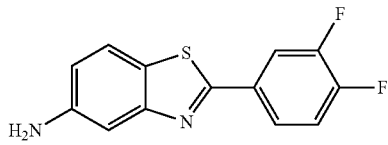

5-Amino-2-(3,4-difluorophenyl)benzothiazole (74g) was prepared analogously to 74a from 5-nitro-2-(3,4-difluorophenyl)benzothiazole (73g, 2.96 g, 10.14 mmol) as a yellow solid (1.60 g, 60%): mp>174° C. dec; $^1$H NMR (400 MHz, DMSO-d$_6$) δ 8.06 (ddd, J=11.4, 7.7, 2.2 Hz, 1H), 7.87 (dddd, J=8.6, 4.3, 2.2, 1.4 Hz, 1H), 7.73 (dd, J=8.6, 0.4 Hz, 1H), 7.61 (dt, J=10.5, 8.4 Hz, 1H), 7.18 (dd, J=2.2, 0.5 Hz, 1H), 6.81 (dd, J=8.6, 2.2 Hz, 1H), 5.37 (s, 2H); HPLC 100 area % (254 nm). Anal. Calcd for C$_{13}$H$_8$F$_2$N$_2$S: C, 59.53; H, 3.07; N, 10.68. Found: C, 59.29; H, 2.94; N, 10.62.

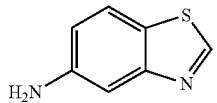

5-Aminobenzothiazole (74h) (Spieler et al., Helv. Chim. Acta 33:1429 (1950); Suzuki et al., *Chem. Pharm. Bull.* 27:1 (1979)). The material above reacted with iron powder and ammonium chloride in aqueous EtOH analogously to the preparation of 74a to give the title compound as beige crystals (1.20 g, 82%): mp 74-75° C.; $^1$H NMR (400 MHz, DMSO-d$_6$) δ 9.16 (s, 1H), 7.72 (dd, J=8.5, 0.5 Hz, 1H), 7.19 (dd, J=2.2, 0.5 Hz, 1H), 6.81 (ddd, J=8.6, 2.2, 0.5 Hz, 1H), 5.28 (s, 2H); HPLC 97.4 area % (254 nm). Anal. Calcd for C$_7$H$_6$N$_2$S: C, 55.98; H, 4.03; N, 18.65. Found: C, 55.99; H, 4.19; N, 18.63.

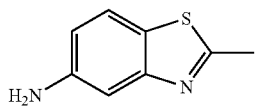

5-Amino-2-methylbenzothiazole (74i) (Hrobarik et al., *J. Phys. Chem. C* 114:22289 (2010)) was prepared analogously to 74a from 2-methyl-5-nitrobenzothiazole (73i, 2.51 g, 12.92 mmol), but the reaction mixture was extracted into ethyl acetate and the product was recrystallized from ethyl acetate/hexanes as light brown needles (1.48 g, 69%): mp 100-101° C.; $^1$H NMR (400 MHz, DMSO-d$_6$) δ 7.57 (dd, J=8:5, 0.5 Hz, 1H), 7.04 (dd, J=2.2, 0.5 Hz, 1H), 6.69 (dd, J=8.5, 2.2 Hz, 1H), 5.22 (s, 2H), 2.69 (s, 3H); HPLC 96.0 area % (254 nm). Anal. Calcd for C$_8$H$_8$N$_2$S: C, 58.51; H, 4.91; N, 17.06. Found: C, 58.21; H, 4.94; N, 17.01.

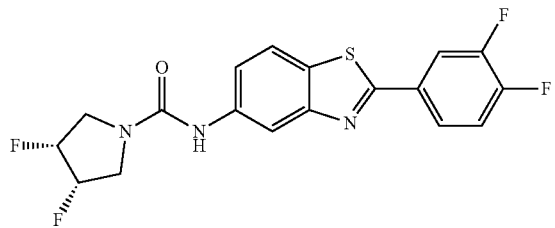 [SMILES: O=C(Nc1ccc2sc(-c3ccc(F)c(F)c3)nc2c1)N1C[C@@H](F)[C@@H](F)C1]

cis-2-(3,4-Difluorophenyl)-5-(3,4-difluoro-N-pyrrolidylamido)benzothiazole (59) was prepared analogously to 1 from 74a (152 mg, 0.578 mmol) and cis-3,4-difluoropyrrolidine HCl (91.7 mg, 0.639 mmol). The crude product was recrystallized from EtOH as a white solid (158 mg, 69%): mp 241-243° C.; $^1$H NMR (400 MHz, DMSO-d$_6$) δ 8.61 (s, 1H), 8.31 (d, J=2.0 Hz, 1H), 8.13 (ddd, J=11.2, 7.6, 2.2 Hz, 1H), 8.01 (d, J=8.8 Hz, 1H), 7.94 (dt, J=7.6, 2.6 Hz, 1H), 7.71-7.56 (m, 2H), 5.50-5.26 (m, 2H), 3.93-3.80 (m, 3H), 3.71-3.56 (m, 2H); EIMS m/z 396.1 (M+1)$^+$; HPLC 99.1 area % (254 nm). Anal. Calcd for C$_{18}$H$_{13}$F$_4$N$_3$OS.0.25H$_2$O: C, 54.06; H, 3.40; N, 10.51. Found: C, 53.87; H, 3.33; N, 10.53.

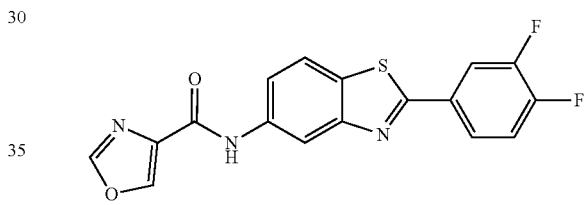

N-(2-(3,4-Difluorophenyl)benzo[d]thiazol-5-yl)oxazole-4-carboxamide (57). A suspension of oxazole-4-carboxylic acid (115 mg, 1.02 mmol) in DCM (10 mL) under Ar was treated with DMF (5 drops) followed by oxalyl chloride (2 M in DCM, 0.75 mL, 1.5 mmol). The mixture was stirred for 3 h and evaporated. The residue dissolved in fresh DCM (10 mL) at 0° C. Amine 74g (135 mg, 0.516 mmoL) was added followed by Et$_3$N, 250 μL, 1.79 mmol). After 30 minutes the cold bath was removed, and the mixture stirred overnight at rt. The mixture was diluted with water and extracted with DCM (4×50 mL). Combined extracts were washed sequentially with 1 M HCl solution, saturated NaHCO$_3$ solution, and saturated NaCl solution. The product was purified on a column of silica gel eluting with hexanes/EtOAc (3:2), followed by recrystallization from EtOH to give a white solid (114 mg, 62%): mp 226-227° C.; $^1$H NMR (400 MHz, DMSO-d$_6$) δ 10.47 (s, 1H), 8.86 (dd, J=1.0, 0.3 Hz, 1H), 8.67 (dd, J=1.0, 0.3 Hz, 1H), 8.64 (dd, J=2.1, 0.5 Hz, 1H), 8.17 (ddd, J=11.3, 7.7, 2.2 Hz, 1H), 8.12 (dd, J=8.7, 0.5 Hz, 1H), 7.96 (dddd, J=8.7, 3.9, 2.2, 1.3 Hz, 1H), 7.92 (dd, J=8.8, 2.0 Hz, 1H), 7.66 (dt, J=10.5, 8.4 Hz, 1H); EIMS m/z 358.0 (M+1)$^+$; HPLC 100 area % (290 nm). Anal. Calcd for C$_{17}$H$_9$F$_2$N$_3$OS: C, 57.14; H, 2.54; N, 11.76. Found: C, 56.87; H, 2.61; N, 11.56.

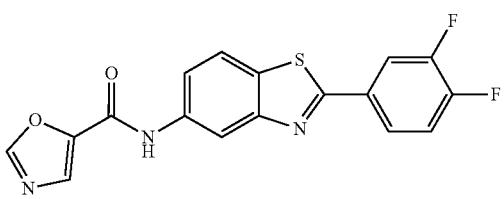

N-(2-(3,4-Difluorophenyl)benzo[d]thiazol-5-yl)oxazole-5-carboxamide (58)

A solution of 74g (151 mg, 0.577 mmol), oxazole-5-carboxylic acid (81.3 mg, 0.719 mmol), and DIEA (350 µL, 2.01 mmol) in DMF (3 mL) under Ar was stirred for 15 min before the addition of HATU (0.276 mg, 0.724=5 mmol). The reaction mixture was stirred for 3 hour before being diluted with water. The precipitate was filtered off, dried, and recrystallized from EtOH to give a solid (156 mg, 76%): mp 245-047° C.; $^1$H NMR (400 MHz, DMSO-$d_6$) δ 10.70 (s, 1H), 8.70 (s, 1H), 8.56 (d, J=2.0 Hz, 1H), 8.17 (ddd, J=11.3, 7.7, 2.2 Hz, 1H), 8.14 (d, J=8.7 Hz, 1H), 8.04 (s, 1H), 7.96 (dt, J=7.8, 2.9 Hz, 1H), 7.80 (dd, J=8.7, 2.1 Hz, 1H), 7.66 (dt, J=10.4, 8.4 Hz, 1H); EIMS m/z 358.0 (M+1)$^+$; HPLC 100 area % (290 nm). Anal. Calcd for $C_{17}H_9F_2N_3OS \cdot 0.1H_2O$: C, 56.85; H, 2.58; N, 11.70. Found: C, 56.61; H, 274; N, 11.55.

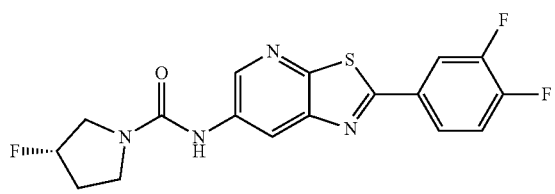 [SMILES: O=C(Nc1cnc2sc(-c3ccc(F)c(F)c3)nc2c1)N1CC[C@H](F)C1]

(S)-2-(3,4-Difluorophenyl)-5-(3-fluoro-N-pyrrolidylamido)-7-azabenzothiazole (56)

was prepared analogously to 1 from 2-(3,4-difluorophenyl)thiazolo[5,4-b]pyridin-6-amine (79, 141 mg, 0.537 mmol). The crude product was purified on a column of silica gel eluting with 5% MeOH in dichloromethane followed by recrystallization from EtOH to give white crystals (99.0 mg, 49%): mp 240-241° C.; $^1$H NMR (400 MHz, DMSO-$d_6$) δ 8.81-8.73 (m, 2H), 8.63 (d, J=2.3 Hz, 1H), 8.17 (ddd, J=11.3, 7.7, 2.2 Hz, 1H), 7.97 (dddd, J=8.5, 4.2, 2.2, 1.3 Hz, 1H), 7.67 (dt, J=10.4, 8.4 Hz, 1H), 5.40 (d, J=53.1 Hz, 1H), 3.82-3.55 (m, 3H), 3.49 (td, J=10.4, 6.9 Hz, 1H), 2.29-2.03 (m, 2H); EIMS m/z 379.1 (M+1)$^+$; HPLC 97.8 area % (254 nm). Anal. Calcd for $C_{17}H_{13}F_3N_4OS \cdot H_2O$: C, 51.51; H, 3.81; N, 14.13. Found: C, 51.65; H, 3.72; N, 14.04.

Synthesis of Intermediates of 56

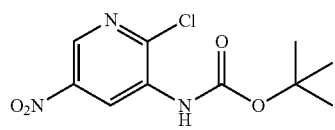 [SMILES: CC(C)(C)OC(=O)Nc1cc([N+](=O)[O-])cnc1Cl]

3-Boc-amino-2-chloro-5-nitropyridine (76)

Diphenylphosphoryl azide (6.09 g, 22.1 mmol) was added to a solution of 2-chloro-5-nitronicotinic acid (3.12 g, 15.4 mmol), triethylamine (3 ml, 21.5 mmol), and tert-butanol (15 mL, 147 mmol) in toluene (75 mL). The mixture was refluxed for 2 hours. After cooling, the mixture was quenched with saturated NaHCO$_3$ solution and extracted with EtOAc. Combined extracts were washed with saturated NaCl solution, dried (MgSO$_4$), and adsorbed onto silica. Purification by silica gel column chromatography (hexanes/EtOAc) to give the title compound which was recrystallized from hexanes to give a solid (1.98 g, 47%): mp>115° C. dec; $^1$H NMR (400 MHz, DMSO-$d_6$) δ 9.39 (s, 1H), 8.94 (d, J=2.6 Hz, 1H), 8.90 (d, J=2.6 Hz, 1H), 1.51 (s, 9H); HPLC 98.9 area % (230 nm). Anal. Calcd for $C_{10}H_{12}ClN_3O_4$: C, 43.89; H, 4.42; N, 15.35. Found: C, 43.86; H, 4.36; N, 15.48.

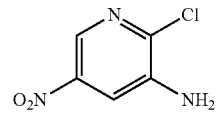 [SMILES: Nc1cc([N+](=O)[O-])cnc1Cl]

3-Amino-2-chloro-5-nitropyridine was also obtained from the reaction above and crystallized from EtOH (337 mg, 13%): mp 195-196° C.; $^1$H NMR (400 MHz, DMSO-$d_6$) δ 8.35 (d, J=2.6 Hz, 1H), 7.84 (d, J=2.5 Hz, 1H), 6.32 (s, 2H); HPLC 100 area % (254 nm). Anal. Calcd for $C_5H_4ClN_3O_2$: C, 34.60; H, 2.32; N, 24.21. Found: C, 34.57; H, 2.38; N, 2194.

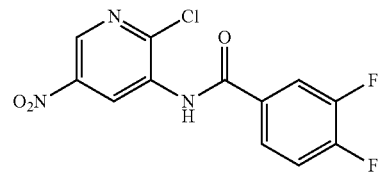 [SMILES: O=C(Nc1cc([N+](=O)[O-])cnc1Cl)c1ccc(F)c(F)c1]

N-(2-Chloro-5-nitropyridin-3-yl)-3,4-difluorobenzamide (77)

A solution of tert-butyl (2-chloro-5-nitropyridin-3-yl)carbamate (76) in dichloromethane (10 mL) was treated with trifluoroacetic acid (10 mL). After stirring for 2 hours, the mixture was evaporated. The crude 2-chloro-5-nitropyridin-3-amine was dissolved in pyridine (10 mL). 3,4-Difluorobenzoyl chloride (1.62 g, 9.18 mmol) was added dropwise. After the addition of more pyridine (2 mL) the mixture was stirred overnight. The mixture was poured over ice. The resulting precipitate was filtered off and recrystallized from EtOH to give the title compound as a solid (1.63 g, 62%): mp 174-176° C.; $^1$H NMR (400 MHz, DMSO-$d_6$) δ 10.64 (s, 1H), 9.13 (d, J=2.6 Hz, 1H), 8.94 (d, J=2.7 Hz, 1H), 8.07 (ddd, J=11.4, 7.7, 2.2 Hz, 1H), 7.92 (dddd, J=8.7, 4.4, 2.2, 1.3 Hz, 1H), 7.68 (ddd, J=10.5, 8.7, 8.0 Hz, 1H); HPLC 100 area % (254 nm). Anal. Calcd for $C_{12}H_6ClF_2N_3O_3$: C, 45.95; H, 1.93; N, 13.40. Found: C, 45.96; H, 2.03; N, 13.30.

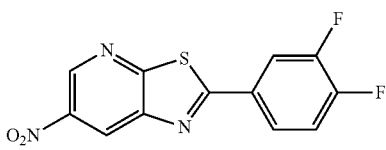

2-(3,4-Difluorophenyl)-5-nitro-7-azabenzothiazole
(78)

A mixture of N-(2-chloro-5-nitropyridin-3-yl)-3,4-difluorobenzamide (77, 1.31 g, 4.17 mmol) and Lawesson's reagent, 1.02 g, 2.52 mmol) in (1,3-dimethyl-3,4,5,6-tetrahydro-2(1H)-pyrimidinone (DMPU, 8 mL) was heated for 15 minutes at 160° C. in a pre-heated oil bath. After cooling, the mixture was poured over ice, and the precipitate was filtered off. After being dried, the product was purified on a column of silica gel eluting with dichloromethane/hexanes. The product was recrystallized from EtOH (674 mg, 55%): mp 217-218° C.; $^1$H NMR (400 MHz, DMSO-$d_6$) δ 9.45 (dd, J=2.4, 0.8 Hz, 1H), 9.21 (dd, J=2.4, 0.9 Hz, 1H), 8.26 (ddd, J=11.1, 7.6, 2.2 Hz, 1H), 8.08 (dddd, J=8.6, 4.2, 2.3, 1.4 Hz, 1H), 7.74 (dt, J=10.3, 8.4 Hz, 1H); HPLC 100 area % (230 nm). Anal. Calcd for $C_{12}H_5F_2N_3O_2S$: C, 49.15; H, 1.72; N, 14.33. Found: C, 48.97; H, 1.76; N, 14.17.

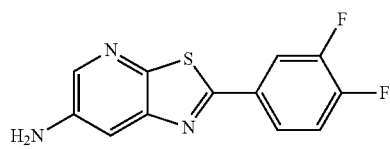

5-Amino-2-(3,4-Difluorophenyl)-7-azabenzothiazole (79) was prepared analogously to 74a from 2-(3,4-difluorophenyl)-6-nitrothiazolo[5,4-b]pyridine (78, 652 mg, 2.22 mmol). The product was recrystallized from EtOH (479 mg, 82%): mp 218-220° C.; $^1$H NMR (400 MHz, DMSO-$d_6$) δ 8.15-8.05 (m, 2H), 7.95-7.86 (m, 1H), 7.64 (dt, J=10.4, 8.4 Hz, 1H), 7.48 (d, J=2.5 Hz, 1H), 5.64 (s, 2H); HPLC 100 area % (254 nm). Anal. Calcd for $C_{12}H_7F_2N_3S$: C, 54.75; H, 2.68; N, 15.96. Found: C, 54.83; H, 2.79; N, 15.99.

Synthesis of 41-54

General Procedure 1

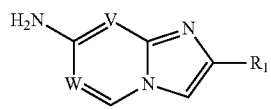

A dried round-bottom flask was charged with appropriate diaminopyridine/pyrimidine (1 eq.), sodium bicarbonate (1.05 eq.) and methanol under an atmosphere of dry argon. Appropriate bromoacetophenone (1.05 eq.) was added slowly at room temperature. Then, the reaction mixture was stirred at reflux for 12 h. The reaction mixture was cooled to room temperature, diluted with water, organic solvent evaporated and remaining water extracted with ethyl acetate. After drying over sodium sulfate and solvent evaporation, the product was purified on a column of silica gel eluting with 0-100% EtOAc in hexanes.

General Procedure 2

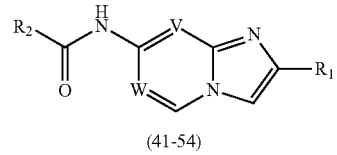

A starting material solution (81a-f, 1 eq., typically 250 mg) and anhydrous $CH_2Cl_2$ (30 mL) was placed under argon and cooled to 5° C. To this solution was carefully added triphosgene (1 eq.), then triethylamine (2 eq.). After 30 min, the reaction was allowed to warm to room temperature and stirred for 1 h. Then, appropriate 2° amine (2 eq.) was added dropwise (if needed, more triethylamine (2 eq.) was added to neutralize 2° amine salt) and the reaction was stirred overnight. The reaction mixture was then diluted with $H_2O$ and the aqueous layer was separated and extracted with $CH_2Cl_2$. After drying over sodium sulfate and solvent evaporation, the product was purified on a column of silica gel eluting with 0-5% MeOH in dichloromethane, followed by recrystallization from MeOH to give a solid.

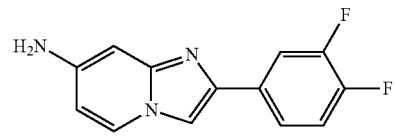 [SMILES: Nc1ccn2cc(-c3ccc(F)c(F)c3)nc2c1]

2-(3,4-difluorophenyl)imidazo[1,2-a]pyridin-7-amine (81a) was prepared from pyridine-2,4-diamine and 2-bromo-1-(3,4-difluorophenyl)ethan-1-one, according to general procedure 1. (250 mg, 65%); $^1$H NMR (300 MHz, MeOD) δ 8.01 (d, J=7.0 Hz, 1H), 7.78 (s, 1H), 7.74-7.62 (m, 1H), 7.61-7.52 (m, 1H), 7.33-7.18 (m, J=8.7, 5.9 Hz, 1H), 6.50 (s, 1H), 6.46 (d, J=7.2 Hz, 1H). ESI MS m/z 245.9 (M+1)$^+$.

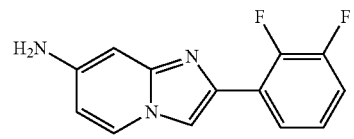 [SMILES: Nc1ccn2cc(-c3cccc(F)c3F)nc2c1]

2-(2,3-difluorophenyl)imidazo[1,2-a]pyridin-7-amine (81b) was prepared from pyridine-2,4-diamine and 2-bromo-1-(2,3-difluorophenyl)ethan-1-one, according to general procedure 1. (168 mg, 40%); $^1$H NMR (300 MHz, MeOD) δ 8.07 (d, J=7.3 Hz, 1H), 7.89 (d, J=3.9 Hz, 1H), 7.87-7.80 (m, 1H), 7.24-7.10 (m, 2H), 6.52 (s, 1H), 6.47 (dd, J=7.3, 2.1 Hz, 1H). ESI MS m/z 245.9 (M+1)$^+$.

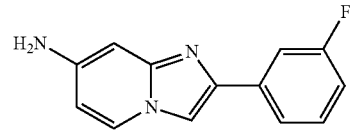 [SMILES: Nc1ccn2cc(-c3cccc(F)c3)nc2c1]

2-(3-fluorophenyl)imidazo[1,2-a]pyridin-7-amine (81c) was prepared from pyridine-2,4-diamine and 2-bromo-1-(3-fluorophenyl)ethan-1-one, according to general procedure 1. (469 mg, 47%); ¹H NMR (500 MHz, MeOD) δ 7.72 (d, J=7.0 Hz, 1H), 7.51 (s, 1H), 7.43-7.31 (m, J=11.1 Hz, 2H), 7.15 (dd, J=13.8, 6.8 Hz, 1H), 6.79 (t, J=8.2 Hz, 1H), 6.34 (s, 1H), 6.22 (d, J=6.9 Hz, 1H). ESI MS m/z 227.9 (M+1)⁺.

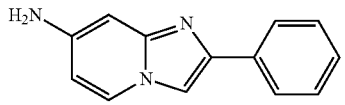

2-phenylimidazo[1,2-a]pyridin-7-amine (81d) was prepared from pyridine-2,4-diamine and 2-bromo-1-phenylethan-1-one, according to general procedure 1. (250 mg, 52%); ¹H NMR (300 MHz, MeOD) δ 7.94 (d, J=7.2 Hz, 1H), 7.77 (d, J=7.7 Hz, 2H), 7.70 (s, 1H), 7.33 (t, J=7.6 Hz, 2H), 7.27-7.17 (m, J=7.2 Hz, 1H), 6.49 (s, 1H), 6.38 (dd, J=7.2, 1.6 Hz, 1H). ESI MS m/z 209.9 (M+1)⁺.

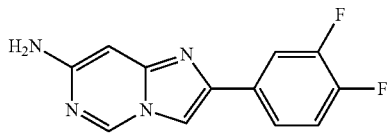 [SMILES: Nc1cc2nc(-c3ccc(F)c(F)c3)cn2cn1]

2-(3,4-difluorophenyl)imidazo[1,2-c]pyrimidin-7-amine (81e) was prepared from pyrimidine-4,6-diamine and 2-bromo-1-(3,4-difluorophenyl)ethan-1-one, according to general procedure 2. (426 mg, 58%); ¹H NMR (500 MHz, MeOD) δ 8.85 (s, 1H), 7.93 (s, 1H), 7.79-7.71 (m, 1H), 7.69-7.62 (m, J=5.2, 3.1 Hz, 1H), 7.31 (dd, J=17.9, 9.3 Hz, 1H), 6.34 (s, 1H). ESI MS m/z 246.9 (M+1)⁺.

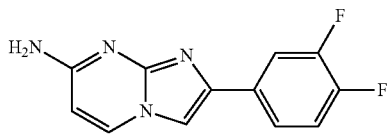 [SMILES: Nc1ccn2cc(-c3ccc(F)c(F)c3)nc2n1]

2-(3,4-difluorophenyl)imidazo[1,2-a]pyrimidin-7-amine (81f) was prepared from pyrimidine-2,4-diamine and 2-bromo-1-(3,4-difluorophenyl)ethan-1-one, according to general procedure 1. (287 mg, 45%); ¹H NMR (500 MHz, MeOD) δ 8.23 (d, J=7.3 Hz, 1H), 7.75-7.67 (m, 1H), 7.68-7.62 (m, 1H), 7.61-7.54 (m, 1H), 7.31-7.19 (m, J=17.1, 8.5 Hz, 1H), 6.34 (d, J=7.3 Hz, 1H). ESI MS m/z 246.9 (M+1)⁺.

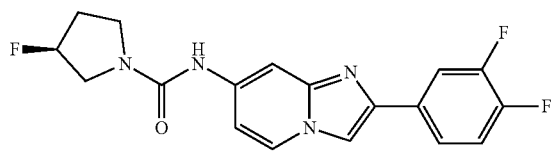 [SMILES: O=C(Nc1ccn2cc(-c3ccc(F)c(F)c3)nc2c1)N1CC[C@H](F)C1]

(3S)-N-[2-(3,4-difluorophenyl)imidazo[1,2-a]pyridin-7-yl]-3-fluoropyrrolidine-1-carboxamide (41) was prepared from 2-(3,4-difluorophenyl)imidazo[1,2-a]pyridin-7-amine (81a) previously synthesized and (S)-(+)-3-Fluoropyrrolidine/HCl, according to general procedure 2. The product was recrystallized from MeOH as brown crystals (45 mg, 73%); ¹H NMR (500 MHz, MeOD) δ 8.16 (d, J=7.3 Hz, 1H), 7.94 (s, 1H), 7.70 (s, 1H), 7.68 (d, J=17.4 Hz, 2H), 7.58 (d, J=6.6 Hz, 1H), 7.22 (q, J=9.1 Hz, 1H), 7.07 (d, J=7.3 Hz, 1H), 5.42 (s, 1H), 5.26 (d, J=52.7 Hz, 1H), 3.77-3.46 (m, 4H), 2.30-1.99 (m, 2H). ESI MS m/z 361.1 (M+1)⁺.

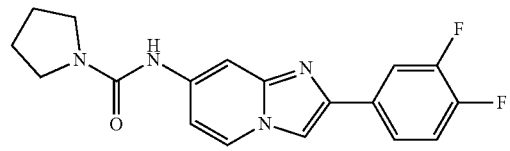 [SMILES: O=C(Nc1ccn2cc(-c3ccc(F)c(F)c3)nc2c1)N1CCCC1]

N-[2-(3,4-difluorophenyl)imidazo[1,2-a]pyridin-7-yl]pyrrolidine-1-carboxamide (42) was prepared from 2-(3,4-difluorophenyl)imidazo[1,2-a]pyridin-7-amine (81a) previously synthesized and pyrrolidine, according to general procedure 2. The product was recrystallized from MeOH as brown crystals (56 mg, 69%); ¹H NMR (500 MHz, MeOD) δ 8.20 (d, J=7.4 Hz, 1H), 7.97 (s, 1H), 7.80-7.71 (m, 2H), 7.68-7.61 (m, 1H), 7.34-7.24 (m, J=17.9, 9.4 Hz, 1H), 7.14 (d, J=7.4 Hz, 1H), 3.56-3.42 (m, 4H), 2.05-1.91 (m, 4H). ESI MS m/z 343.1 (M+1)⁺.

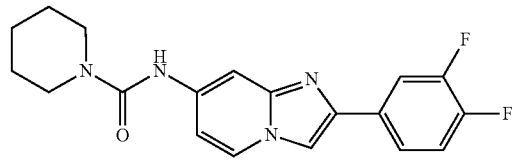 [SMILES: O=C(Nc1ccn2cc(-c3ccc(F)c(F)c3)nc2c1)N1CCCCC1]

N-[2-(3,4-difluorophenyl)imidazo[1,2-a]pyridin-7-yl]piperidine-1-carboxamide (43) was prepared from 2-(3,4-difluorophenyl)imidazo[1,2-a]pyridin-7-amine (81a) previously synthesized and piperidine, according to general procedure 2. The product was recrystallized from MeOH as brown crystals (98 mg, 57%); ¹H NMR (500 MHz, MeOD) 8.13 (d, J=7.3 Hz, 1H), 7.92 (s, 1H), 7.71-7.63 (m, 1H), 7.56 (s, 2H), 7.22 (q, J=9.2 Hz, 1H), 7.00 (d, J=7.4 Hz, 1H), 3.47-3.42 (m, 4H), 1.66-1.58 (m, J=4.5 Hz, 2H), 1.59-1.51 (m, 4H). ESI MS m/z 357.1 (M+1)⁺.

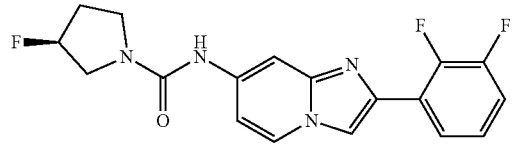

(3S)-N-[2-(2,3-difluorophenyl)imidazo[1,2-a]pyridin-7-yl]-3-fluoropyrrolidine-1-carboxamide (44) was prepared from 2-(2,3-difluorophenyl)imidazo[1,2-a]pyridin-7-amine (81b) previously synthesized and (S)-(+)-3-Fluoropyrrolidine/HCl, according to general procedure 2. The product was recrystallized from MeOH as brown crystals (67 mg, 55%); ¹H NMR (500 MHz, MeOD) δ 8.23 (d, J=7.2 Hz, 1H), 8.04 (s, 1H), 7.84 (t, J=16.4 Hz, 1H), 7.76 (s, 1H), 7.20-7.12 (m, 2H), 7.10 (d, J=7.4 Hz, 1H), 5.27 (d, J=52.6 Hz, 1H), 3.79-3.47 (m, J=27.7, 17.3, 11.4 Hz, 4H), 2.31-2.01 (m, 2H). ESI MS m/z 361.3 (M+1)⁺.

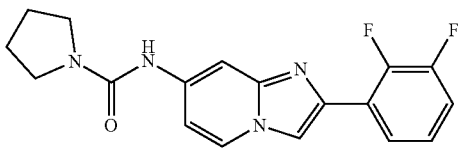 [SMILES: O=C(Nc1ccn2cc(-c3cccc(F)c3F)nc2c1)N1CCCC1]

N-[2-(2,3-difluorophenyl)imidazo[1,2-a]pyridin-7-yl]pyrrolidine-1-carboxamide (45) was prepared from 2-(2,3-difluorophenyl)imidazo[1,2-a]pyridin-7-amine (81b) previously synthesized and pyrrolidine, according to general procedure 2. The product was recrystallized from MeOH as brown crystals (81 mg, 58%); $^1$H NMR (500 MHz, MeOD) δ 8.21 (d, J=7.4 Hz, 1H), 8.02 (s, 1H), 7.83 (t, J=6.8 Hz, 1H), 7.74 (s, 1H), 7.19-7.10 (m, 2H), 7.09 (d, J=5.7 Hz, 1H), 3.41 (s, 4H), 1.91 (s, 4H). ESI MS m/z 343.0 (M+1)$^+$.

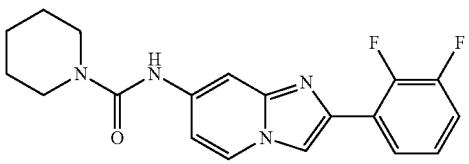

N-[2-(2,3-difluorophenyl)imidazo[1,2-a]pyridin-7-yl]piperidine-1-carboxamide (46) was prepared from 2-(2,3-difluorophenyl)imidazo[1,2-a]pyridin-7-amine (81b) previously synthesized and piperidine, according to general procedure 2. The product was recrystallized from MeOH as brown crystals (83 mg, 58%); $^1$H NMR (500 MHz, MeOD) δ 8.24 (s, 1H), 8.05 (d, J=3.8 Hz, 1H), 7.89 (t, J=7.0 Hz, 1H), 7.68 (s, 1H), 7.27-7.16 (m, 2H), 7.08 (d, J=7.4, 2.1 Hz, 1H), 3.56-3.51 (m, 4H), 1.74-1.67 (m, 2H), 1.67-1.60 (m, J=11.1, 5.6 Hz, 4H). ESI MS m/z 357.1 (M+1)$^+$.

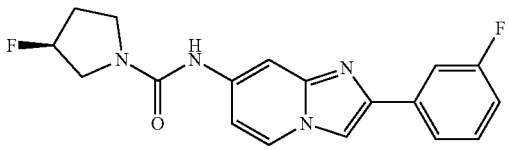 [SMILES: O=C(Nc1ccn2cc(-c3cccc(F)c3)nc2c1)N1CC[C@H](F)C1]

(3S)-3-fluoro-N-[2-(3-fluorophenyl)imidazo[1,2-a]pyridin-7-yl]pyrrolidine-1-carboxamide (47) was prepared from 2-(3-fluorophenyl)imidazo[1,2-a]pyridin-7-amine (81c) previously synthesized and (S)-(+)-3-Fluoropyrrolidine/HCl, according to general procedure 2. The product was recrystallized from MeOH as brown crystals (75 mg, 49%); $^1$H NMR (500 MHz, MeOD) δ 8.18 (d, J=7.2 Hz, 1H), 7.99 (s, 1H), 7.71 (s, 1H), 7.61 (d, J=7.7 Hz, 1H), 7.55 (d, J=10.3 Hz, 1H), 7.35 (dd, J=14.3, 7.1 Hz, 1H), 7.09 (d, J=7.3 Hz, 1H), 6.97 (t, J=8.3 Hz, 1H), 5.26 (d, J=52.7 Hz, 1H), 3.78-3.47 (m, J=27.6, 17.3, 11.4 Hz, 4H), 2.30-2.04 (m, 2H). ESI MS m/z 343.1 (M+1)$^+$.

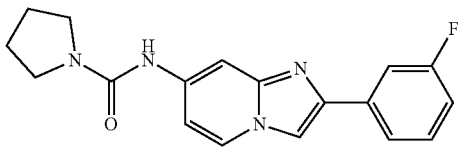

N-[2-(3-fluorophenyl)imidazo[1,2-a]pyridin-7-yl]pyrrolidine-1-carboxamide (48) was prepared from 2-(3-fluorophenyl)imidazo[1,2-a]pyridin-7-amine (81c) previously synthesized and pyrrolidine, according to general procedure 2. The product was recrystallized from MeOH as brown crystals (71 mg, 48%); $^1$H NMR (500 MHz, MeOD) δ 8.02 (d, J=7.2 Hz, 1H), 7.84 (s, 1H), 7.63 (s, 1H), 7.53 (d, J=7.7 Hz, 1H), 7.47 (d, J=10.4 Hz, 1H), 7.28 (q, J=6.8 Hz, 1H), 6.96 (d, J=7.3 Hz, 1H), 6.91 (t, J=8.4 Hz, 1H), 3.32 (s, 4H), 1.82 (s, 4H). ESI MS m/z 325.1 (M+1)$^+$.

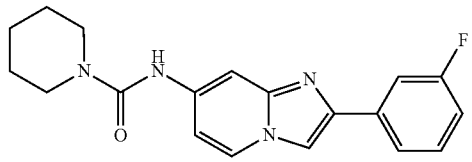 [SMILES: O=C(Nc1ccn2cc(-c3cccc(F)c3)nc2c1)N1CCCCC1]

N-[2-(3-fluorophenyl)imidazo[1,2-a]pyridin-7-yl]piperidine-1-carboxamide (49) was prepared from 2-(3-fluorophenyl)imidazo[1,2-a]pyridin-7-amine (81c) previously synthesized and piperidine, according to general procedure 2. The product was recrystallized from MeOH as brown crystals (65 mg, 55%); $^1$H NMR (500 MHz, MeOD) δ 8.20 (d, J=7.4 Hz, 1H), 8.01 (s, 1H), 7.71 (s, 1H), 7.57 (d, J=7.8 Hz, 1H), 7.51 (d, J=10.2 Hz, 1H), 7.36 (dd, J=14.0, 8.0 Hz, 1H), 7.09 (dd, J=7.4, 2.0 Hz, 1H), 7.00 (td, J=8.5, 2.4 Hz, 1H), 3.50-3.46 (m, 4H), 1.67-1.61 (m, 2H), 1.60-1.54 (m, J=7.6 Hz, 4H). ESI MS m/z 339.1 (M+1)$^+$.

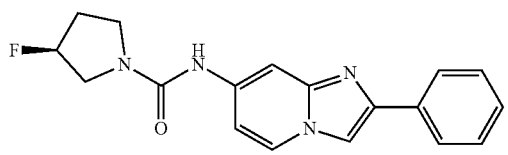 [SMILES: O=C(Nc1ccn2cc(-c3ccccc3)nc2c1)N1CC[C@H](F)C1]

(3S)-3-fluoro-N-{2-phenylimidazo[1,2-a]pyridin-7-yl}pyrrolidine-1-carboxamide (50) was prepared from 2-phenylimidazo[1,2-a]pyridin-7-amine (81d) previous synthesized and (S)-(+)-3-Fluoropyrrolidine/HCl, according to general procedure 2. The product was recrystallized from MeOH as brown crystals (78 mg, 76%); $^1$H NMR (300 MHz, MeOD) δ 8.23 (d, J=7.4 Hz, 1H), 7.98 (s, 1H), 7.84 (s, 1H), 7.83-7.77 (m, 2H), 7.40 (t, J=7.4 Hz, 2H), 7.32 (d, J=7.2 Hz, 1H), 7.15 (dd, J=7.4, 2.0 Hz, 1H), 5.30 (d, J=52.7 Hz, 1H), 3.86-3.49 (m, 4H), 2.37-1.98 (m, 2H). ESI MS m/z 325.1 (M+1)$^+$.

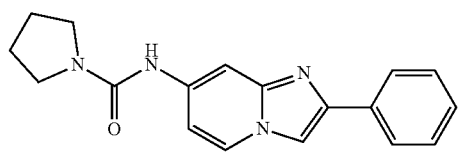 [SMILES: O=C(Nc1ccn2cc(-c3ccccc3)nc2c1)N1CCCC1]

N-{2-phenylimidazo[1,2-a]pyridin-7-yl}pyrrolidine-1-carboxamide (51) was prepared from 2-phenylimidazo[1,2-a]pyridin-7-amine (81d) previously synthesized and pyrrolidine, according to general procedure 2. The product was recrystallized from MeOH as brown crystals (90 mg, 78%); $^1$H NMR (500 MHz, MeOD) δ 8.49 (d, J=7.4 Hz, 1H), 8.25 (s, 2H), 7.74 (d, J=7.7 Hz, 2H), 7.49 (t, J=7.4 Hz, 3H), 7.46-7.41 (m, J=7.1 Hz, 1H), 3.50-3.40 (m, 4H), 1.99-1.88 (m, 4H). ESI MS m/z 307.3 (M+

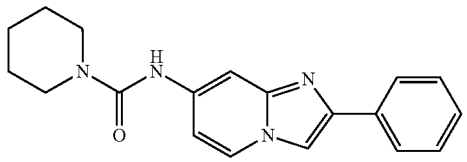 [SMILES: O=C(Nc1ccn2cc(-c3ccccc3)nc2c1)N1CCCCC1]

N-{2-phenylimidazo[1,2-a]pyridin-7-yl}piperidine-1-carboxamide (52) was prepared from 2-phenylimidazo[1,2-a]pyridin-7-amine (81d) previously synthesized and piperidine, according to general procedure 2. The product was recrystallized from MeOH as brown crystals (72 mg, 75%); $^1$H NMR (500 MHz, MeOD) δ 8.16 (d, J=7.3 Hz, 1H), 7.91 (s, 1H), 7.73 (d, J=7.6 Hz, 2H), 7.69 (s, 1H), 7.33 (t, J=7.5 Hz, 2H), 7.25 (t, J=7.3 Hz, 1H), 7.06 (d, J=8.9 Hz, 1H), 3.58-3.27 (m, 4H), 1.60 (d, J=4.2 Hz, 2H), 1.54 (d, J=3.5 Hz, 4H). ESI MS m/z 321.1 (M+1)$^+$.

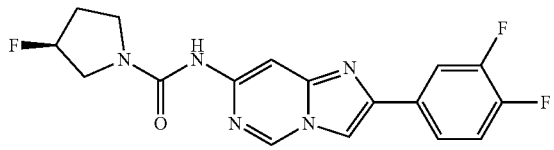

(3S)-N-[2-(3,4-difluorophenyl)imidazo[1,2-c]pyrimidin-7-yl]-3-fluoropyrrolidine-1-carboxamide (53) was prepared from 2-(3,4-difluorophenyl)imidazo[1,2-c]pyrimidin-7-amine (81e) previously synthesized and (S)-(+)-3-Fluoropyrrolidine/HCl, according to general procedure 2. The product was recrystallized from MeOH as brown crystals (65 mg, 68%); $^1$H NMR (500 MHz, DMSO) δ 9.22 (d, J=1.3 Hz, 1H), 8.80 (s, 1H), 8.31 (s, 1H), 7.96 (ddd, J=11.9, 7.9, 2.0 Hz, 1H), 7.87 (s, 1H), 7.85-7.79 (m, 1H), 7.48 (dt, J=10.5, 8.6 Hz, 1H), 5.43-5.28 (m, J=53.2 Hz, 1H), 3.85-3.46 (m, J=52.1, 27.7, 21.1, 11.4 Hz, 4H), 2.25-2.03 (m, 2H). ESI MS m/z 362.1 (M+1)$^f$.

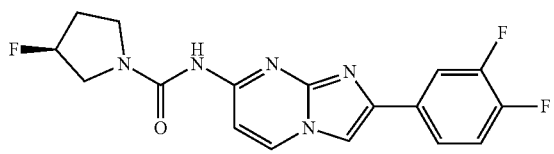 [SMILES: O=C(Nc1cc2nc(-c3ccc(F)c(F)c3)cn2cn1)N1CC[C@H](F)C1]

(3S)-N-[2-(3,4-difluorophenyl)imidazo[1,2-a]pyrimidin-7-yl]-3-fluoropyrrolidine-1-carboxamide (54) was prepared from 2-(3,4-difluorophenyl)imidazo[1,2-a]pyrimidin-7-amine (81f) previously synthesized and (S)-(+)-3-Fluoropyrrolidine/HCl, according to general procedure 2. The product was recrystallized from MeOH as brown crystals (50 mg, 55%); $^1$H NMR (500 MHz, MeOD) δ 8.58 (d, J=7.5 Hz, 1H), 7.94 (s, 1H), 7.80-7.76 (m, J==7.5 Hz, 1H), 7.76-7.73 (m, J=7.8, 2.0 Hz, 1H), 7.68-7.64 (m, 1H), 7.30 (dd, J=18.8, 8.5 Hz, 1H), 5.58-5.15 (m, 1H), 3.86-3.56 (m, 4H), 2.37-2.07 (m, 2H). ESI MS m/z 362.1 (M+1)$^+$.

Abbreviations

Boc, tert-butoxycarbonyl
DCM, dichloromethane
DIEA, diisopropylethylamine
DMF, N,N-dimethylformamide
DPPA, diphosphorylphenyl azide
EtOH, ethanol
EtOAc, ethyl acetate
Et$_3$N, triethylamine
h, hour(s)
HATU, 1-[bis(dimethylamino)methylene]-1H-1,2,3-triazolo[4,5-b]pyridinium 3-oxide hexafluorophosphate
min, minute(s)
Py, pyridine
t-BuOH, tert-butanol
THF, tetrahydrofuran
TFA, trifluoracetic acid
rt, room temperature DGS would like to thank FAPESP (São Paulo research foundation) [grant number 2013/01128-0], [grant number 2016/10362-5] for the financial support.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

What is claimed is:

1. A compound of formula IV:

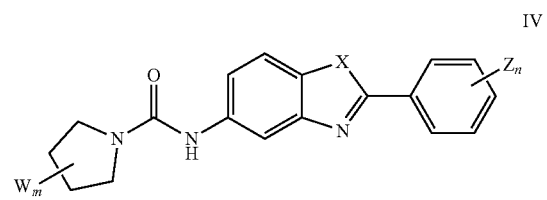

IV wherein:
X is S, O, or NH;
W is $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group;
m is an integer from 0-4;
Z is $C_{1-6}$ alkyl, $C_{1-6}$ alkoxy, halo, trifluoromethyl, cyano, amino, N—$C_{1-6}$ alkylamino, or N,N—$C_{1-6}$ dialkylamino group; and
n is an integer from 0-4;
or a pharmaceutically acceptable salt, prodrug, or optical isomer thereof.

2. The compound of claim 1, wherein X is S.
3. The compound of claim 1, wherein m is 1 or 2.
4. The compound of claim 1, wherein n is 1, 2, or 3.
5. The compound of claim 1, wherein W and/or Z is halo.
6. The compound of claim 1, wherein W and/or Z is F.
7. The compound of claim 1, selected from the group consisting of:

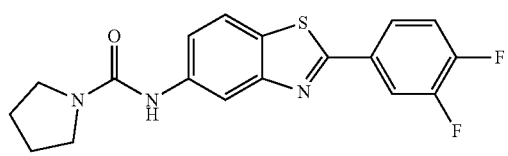

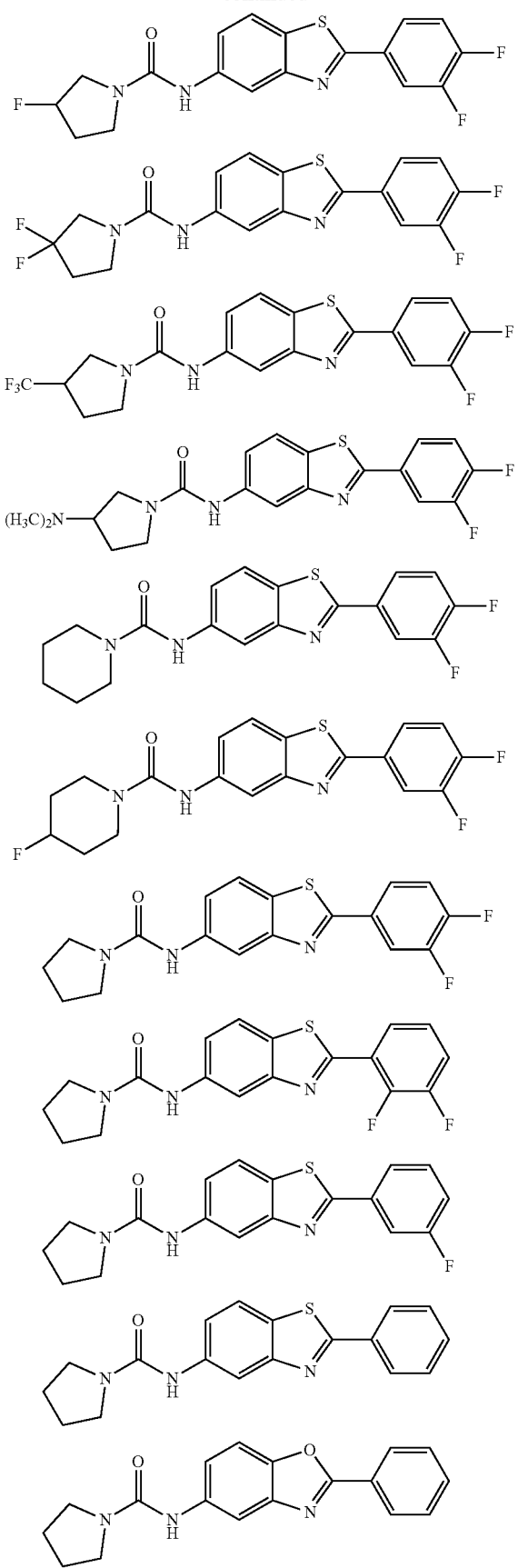
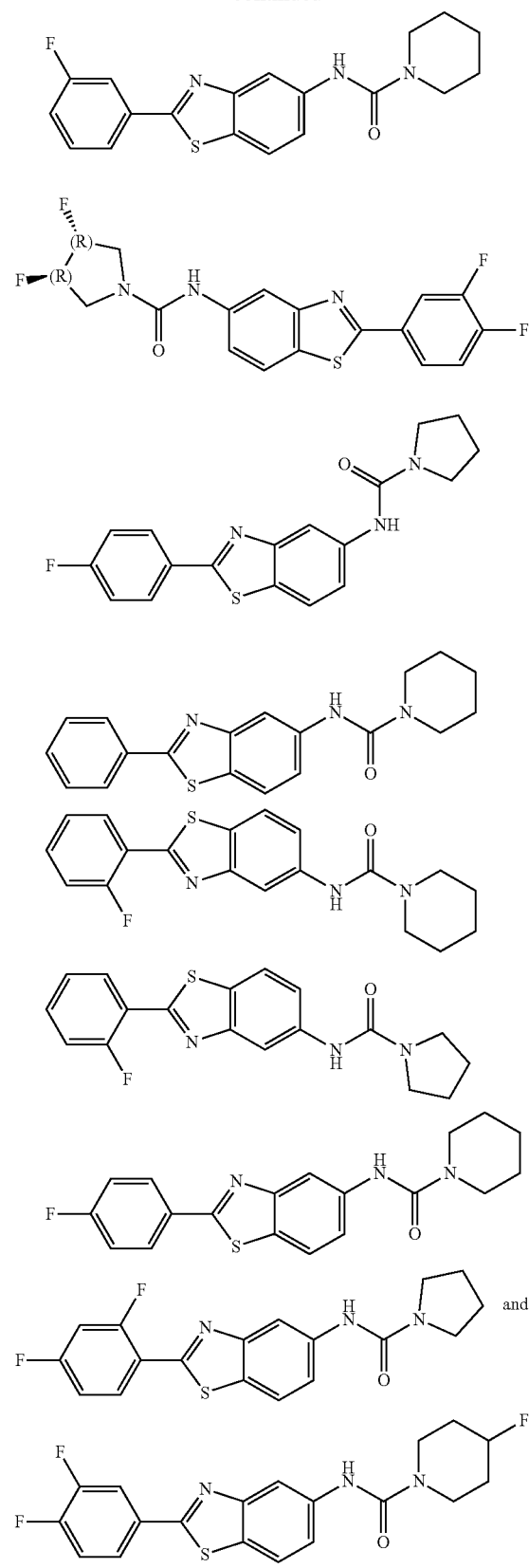
or a pharmaceutically acceptable salt, prodrug, or optical isomer thereof.

8. The compound of claim 1, which is:

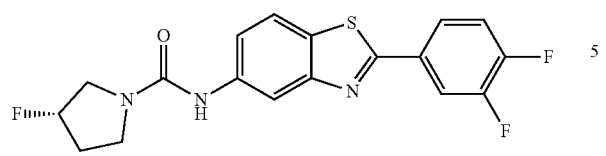

or a pharmaceutically acceptable salt or prodrug thereof.

9. A pharmaceutical composition comprising the compound of claim 1, or a pharmaceutically acceptable salt, prodrug, or optical isomer thereof, and a pharmaceutically acceptable carrier.

10. A kit comprising the compound of claim 1, or a pharmaceutically acceptable salt, prodrug, or optical isomer thereof.

* * * * *